(12) United States Patent
Sale et al.

(10) Patent No.: US 7,368,259 B2
(45) Date of Patent: *May 6, 2008

(54) METHOD FOR GENERATING DIVERSITY

(75) Inventors: Julian Edward Sale, Cambridge (GB); Michael Samuel Neuberger, Cambridge (GB); Sarah Jane Cumbers, Coulsdon (GB); Shunichi Takeda, Kyoto (JP)

(73) Assignee: Medical Research Council, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/733,532

(22) Filed: Dec. 11, 2003

(65) Prior Publication Data

US 2005/0026246 A1 Feb. 3, 2005

Related U.S. Application Data

(63) Continuation of application No. PCT/GB02/02688, filed on Jun. 11, 2002, which is a continuation of application No. 10/146,505, filed on May 15, 2002, which is a continuation of application No. 09/879,813, filed on Jun. 11, 2001, now abandoned.

(51) Int. Cl.
*C12Q 1/04* (2006.01)
*C12N 15/01* (2006.01)
*C12N 15/63* (2006.01)
*C12N 5/08* (2006.01)

(52) U.S. Cl. .................. 435/34; 435/326; 435/377; 435/441; 435/455; 435/29

(58) Field of Classification Search .............. None
See application file for complete search history.

(56) References Cited

U.S. PATENT DOCUMENTS

| 5,750,335 A | 5/1998 | Gifford |
| 6,146,894 A | 11/2000 | Nicolaides et al. ......... 435/440 |
| 7,122,339 B2 * | 10/2006 | Sale et al. .................... 435/34 |

FOREIGN PATENT DOCUMENTS

| WO | WO-93-12228 A1 | 6/1993 |
| WO | WO-95-12689 A1 | 5/1995 |
| WO | WO 00/22111 | 4/2000 |

OTHER PUBLICATIONS

Monteiro et al. Molecular methods for the detection of mutations. Teratog Carcinog Mutagen. 2000;20(6):357-86.*
Phung et al. Hypermutation in Ig V genes from mice deficient in the MLH1 mismatch repair protein.J Immunol. Mar. 15, 1999;162(6):3121-4.*
Sale et al. Ablation of XRCC2/3 transforms immunoglobulin V gene conversion into somatic hypermutation. Nature. Aug. 30, 2001;412(6850):921-6.*
Papavasiliou et al. Somatic hypermutation of immunoglobulin genes: merging mechanisms for genetic diversity. Cell. Apr. 2002;109 Suppl:S35-44.*
Cui et al. The XRCC2 and XRCC3 repair genes are required for chromosome stability in mammalian cells. Mutat Res. Jun. 23, 1999;434(2):75-88.*
Griffin et al. Mammalian recombination-repair genes XRCC2 and XRCC3 promote correct chromosome segregation. Nat Cell Biol. Oct. 2000;2(10):757-61.*
Adetugbo, K. et al., "Molecular analysis of spontaneous somatic mutants," Nature 265:299-304 (1977).
Bahler, D. W. and Levy, R., "Clonal evolution of a follicular lymphomas: Evidence for antigen selections," PNAS USA 89:6770-6774 (1992).
Bass, S. et al., "Hormone Phage: An Enrichment Method for Variant Proteins With Altered Binding Properties," Proteins 8:309-314 (1990).
Berek, C. and Milstein, C., "The dynamic nature of the antibody repertorie," Immunol. Rev. 105:5-26 (1988).
Betz, A.G., et al., "Elements Regulating Somatic Hypermutation of an Immunoglobulin K Gene: Critical Role for the Intron Enhancer/ Matrix Attachment Region," Cell 77:239-248 (1994).
Betz, A.G. et al., "Discriminating intrinsic and antigen-selected mutational hotspots in immunoglobulin V genes," Immunol. Today 14:405-411 (1993).
Bezzubova, O. et al., "Reduced X-ray resistance and homologous recombination frequencies in a RAD54-/-mutant of the chicken DT40 cell line," Cell 89:185-193 (1997).
Bonfield, J.K. et al., "A new DNA-sequence assembly program," Nucleic Acids Res. 23:4992-4999 (1995).
Bouvet, J.P. and Dighiero, G., "From natural polyreactive autoantibodies to a la carte monoreactive antibodies to infectious agents: is it a small world after all?" Infect. Immun. 66:1-4 (1998).
Braeuninger, A. et al., "Hodgkin and Reed-Sternberg cells in lymphocyte predominant disease represent clonal populations of germinal center-derived tumor B cells," PNAS USA 94:9337-9342 (1997).
Brenneman, M.A. et al., "XRCC3 is required for efficient repair of chromosome breaks by homologous recombination," Mutat. Res. 459:89-97 (2000).
Bross, L. et al., "DNA double-strand breaks in immunoglobulin genes undergoing somatic hypermutation," Immunity 13:589-597 (2000).
Bruggemann, M. et al., "Immunoglobulin V region variants in hybridoma cells. I. Isolation of a variant with altered idiotypic and antigen binding specificity," EMBO J. 1:629-634 (1982).
Buerstedde, J. et al., Light chain gene conversion continues at high rate in an ALV-induced cell line, Embo J. 9:921-927 (1990).

(Continued)

*Primary Examiner*—Daniel M. Sullivan
(74) *Attorney, Agent, or Firm*—Wilson Sonsini Goodrich & Rosati

(57) ABSTRACT

The invention relates to a method for preparing an antibody-producing cell line capable of directed constitutive hypermutation of a specific nucleic acid region, comprising the steps of: a) screening a clonal cell population for V gene diversity; b) isolating one or more cells which display V gene diversity and comparing the rate of accumulation of mutations in the V genes and other genes of the selected cells; and c) selecting a cell in which the rate of V gene mutation exceeds that of other gene mutation.

14 Claims, 34 Drawing Sheets

OTHER PUBLICATIONS

Capizzi and Jameson, "A table for the estimation of the spontaneous mutation rate of cells in culture," Mutat. Res. 17:147-148 (1973).
Casali, P. and Schettino, E.W., "Structure and function of natural antibodies," Curr. Top. Microbiol. Immunol. 10:167-179 (1996).
Chapman, C.J. et al. "Analysis of VH genes used by neoplastic B cells in endemic Burkitt's lymphoma shows somatic hypermutation and intraclonal heterogeneity," Blood 85:2176-2181 (1995).
Chapman, K.B. and Szostak, J.W., "In vitro selection of catalytic RNAs," Curr. Op. Struct. Biol. 4:618-622 (1994).
Chui, Y.L. et al., "A reporter gene to analyse the hypermutation of immunoglobulin genes," J. Mol. Biol. 249:555-563 (1995).
Clackson, T. and Wells, J.A., "In vitro selection from protein and peptide libraries,"Trends Biotechnol. 12:173-184 (1994).
Coffino, P. and Scharff, M.D., "Rate of somatic mutation in immunoglobulin production by mouse myeloma cells," Mutat. Res. 434:75-88 (1999).
Cui, X. et al., "The XRCC2 and XRCC3 repair genes are required for chromosome stability in mammalian cells," PNAS USA 68:219-223 (1971).
Cull, M.G. et al., "Screening for receptor ligands using large libraries of peptides linked to the C terminus of the lac repressor," PNAS USA 89:1865-1869 (1992).
Deans, B. et al., XRCC2 is required for genetic stability, embryonic neurogenesis and viability in mice, Embo J. 19:6675-6685 (2000).
Denepoux, S. et al., "Induction of somatic mutation in a human B cell line in vitro," Immunity 6:35-46 (1997).
Diaz, M. et al., "Evolution and the molecular basis of somatic hypermutation of antigen receptor genes," Philos. Trans. R. Soc. Lond. B Biol. Sci. 356:67-72 (2001).
Drake, J.W., "Rates of spontaneous mutation," Genetics 148:1667-1686 (1998).
Ellington, A.D. and Szostak, J.W., "In vitro selection of RNA molecules that bind specific ligands,"Nature 346:81822 (1990).
Gold, L., et al., "Diversity of Oligonucleotide Functions,"Annual Rev. Biochem. 65:763-797 (1995).
Gonzalez-Fernandez and Milstein, "Analysis of somatic hypermutation in mouse Peyer's patches using immunoglobulin κ light-chain transgenes,"PNAS USA 90:9862-9866 (1993).
Goossens, T. et al., "Frequent occurrence of deletions and duplications during somatic hypermutation: Implications for oncogenic translocations and heavy chain disease," PNAS USA 95:2463-2468 (1998).
Goyenechea, B. et al., "Cells strongly expressing Igk transgenes show clonal recruitment of hypermutation: a role for both MAR and the enhancers," Embo. J. 16:3987-3994 (1997).
Green, N.S. et al., "Immunoglobulin hypermutation in cultured cells," Immunol. Rev. 162:77-87 (1998).
Green, N.S. et al., "IG V Region Hypermutation in B Cell Hybrids Mimics In Vivo Mutation and Allows for Isolation of Clonal Variants,"Mol. Immunol. 34(15):1095-1103 (1997).
Green, R. and Szostak, J.W., "Selection of a Ribozyme That Functions as a Superior Template in a Self-Copying Reaction," Science 258:1910-1915 (1992).
Griffin, C.S. et al., "Mammalian recombination-repair genes XRCC2 and XRCC3 promote correct chromosome segregation," Nat. Cell Biol. 2:757-761 (2000).
Jain, R. et al., "A potential role for antigen selection in the clonal evolution of Burkitt's lymphoma," J. Immunol. 153:45-52 (1994).
Johnson, R.D. et al., "Mammalian XRCC2 promotes the repair of DNA double-strand breaks by homologous recombination," Nature 401:397-399 (1999).
Jolly, C.J. et al., "Rapid methods for the analysis of immunoglobulin gene hypermutation: application to transgenic and gene targeted mice," Nuceic Acids Research 25(10):1913-1919 (1997).
Jolly, C.. et al., "The targeting of somatic hypermutation," Semin. Immunol. 8:159-168 (1996).
Joyce, G.F., "In vitro evolution of nucleic acids,"Curr. Op. Struct. Biol. 4:331-336 (1994).
Kallberg, E. et al., "Somatic mutation of immunoglobulin V genes in vitro," Science 271:1285-1289 (1996).

Kim, S. et al., "Ongoing diversification of the rearranged immunoglobulin light-chain gene in a bursal lymphoma cell line," Mol. Cell Biol. 10:3224-3231 (1990).
Klein, G. et al., "An EBV negative cell line established from a American Burkitt lymphoma; receptor characteristics, EBV infectability and permanent conversion into EBV-positive sublines by in vitro infection," Intervirology 5:319-334 (1975).
Klix et al., "Multiple sequences from downstream of the Jx cluster can combine to recruit somatic hypermutation to a heterologous, upstream mutation domain," Eur. J. Immunol. 28:317-326 (1998).
Liu, N. et al., "XRCC2 and XRCC3, new human Rad51-family members, promote chromosome stability and protect against DNA cross-links and other damages," Mol. Cell 1:783-793 (1998).
Lundberg, K.S. et al., "High-fidelity amplification using a thermostable DNA polymerase isolated from Pyrococcus furiosus,"Gene 108:1-6 (1991).
Luria and Delbreck, "Mutations of bacteris from virus sensitivity to virus resistance," Genetics 28:491-511 (1943).
Maizels, N., "Somatic hypermutation: how many mechanisms diversity V region sequences?" Cell 83:9-12 (1995).
Mattheakis, L.C. et al., "An in vitro polysome display system for identifying ligands from very large peptide libraries,"PNAS USA 91:9022-9026 (1994).
Matthias et al., "Eukaryotic expression vectors for the analysis of mutant proteins," NAR 17:6418 (1989).
Max, EE. et al., "The Nucleotide Sequence of a 5.5-kilobase DNA Segment Containing the Mouse k Immunoglobulin J and C Region Genes," J. Biol. Chem. 256:5116-5120 (1981).
McCafferty, J. et al., "Phage antibodies: filamentous phage displaying antibody variable domains," Nature 348:552-554 (1990).
McCormack, W.T. et al., "Germ line maintenance of the pseudogene donor pool for somatic immunoglobulin gene conversion in chickens," Mol. Cell Biol. 13:821-830.
McKean, D. et al., "Generation of antibody diversity in the immune response of BALB/c mice to influenza virus haemagglutinin," PNAS USA 81:3180-3184 (1984).
Moore, M.J., "Exploration by lamp light," Nature 374:766-767 (1995).
Mu-Quan, M. et al., "Sequence dependent hypermutation of the immunoglobulin heavy chain in cultured B cells,"PNAS USA 94:5284-5289 (1997).
Neuberger, M.S. and Milstein, C., "Somatic hypermutation," Curr. Op. Immunol. 7:248-254 (1995).
Papavasiliou, F.N. and Schatz, D.G., "Cell-cycle-regulated DNA double-stranded breaks in somatic hypermutation of immunoglobulin genes," Nature 408:216-221 (2000).
Parham, P. ed., Immunol. Reviews. Somatic hypermutation of immunoglobulin genes, vol. 162, Apr. 1998 (Copenhagen, Denmark: Munksgaard).
Pierce, A.J., et al., "XRCC3 promotes omology-directed repair of DNA damage in mammalian cells," Genes Dev. 13:2633-2638 (1999).
Rada, C. et al., "Hot spot focusing of somatic hypermutation in MSH2-deficient mice suggests two stages of mutational targeting," Immunity 9:135-141 (1998).
Ratech, H., "Rapid cloning of rearranged immunoglobulin heavy chain genes from human-B-cell lines using anchored polymerase chain reaction," Biochem. Biophys. Res. Commun. 182:1260-1263 (1992).
Reynaud, C.A., et al., "A hyperconversion mechanism generates the chicken light chain preimmune repertoire," Cell 48:379-388 (1987).
Reynaud, C.A. et al., "Somatic hyperconversion diversifies the single $V_H$ gene of the chicken with a high incidence in the D region," Cell 59:171-183 (1989).
Rogozin, I.B. and Kolchanov, N.A., "Somatic hypermutation of immunoglobulin genes. II. Influence of neighbouring base sequences on mutagenesis," Biochem. Biophys. Acta 1171:11-18 (1992).
Rooney, C.M., "Paired Epstein-Barr virus-carrying lymphoma and lymphoblastoid cell lines from Burkitt's lymphoma patients: comparative sensitivity to non-specific and to allo-specific cytotoxic responses in vitro," Int. J. Cancer 34:339-348 (1984).

Rowe, M. et al., "Differences in B cell growth phenotype reflect novel patterns of Epstein-Barr virus latent gene expression in Burkitt's lymphoma cells," Embo J. 6:2743-2751 (1987).

Sale, J.E. and Neuberger, M.S., "TdT-accessible breaks are scattered over the immunoglobulin V domain in a constituitively hypermutating B cell line," Immunity 9:859-869 (1998).

Sharpe et al., "Somatic hypermutation of immunoglobulin κ may depend on sequences 3' of Cκ and occurs on passenger transgenes," Embo J. 10:2139-2145 (1991).

Smith, G.P., "Filamentous Fusion Phage: Novel Expression Vectors that Display Cloned Antigens on the Virion Surface," Science 228:1315-1317 (1985).

Takata, M. et al., "The Rad51 paralog Rad51B promotes homologous recombinational repair," Mol. Cell Biol. 20:6476-6482 (2000).

Takata, M. et al., "Homologous recombination and non-homologous end-joining pathways of DNA double-strand break repair have overlapping roles in the maintenance of chromosomal integrity in vertebrate cells," Embo J. 17:5497-5508 (1998).

Takata, M. et al., "Chromosome Instability and Defective Recombinational Repair in Knockout Mutants of the Five Rad51 Paralogs," Mol. Cell Biol. 21:2858-2866 (2001).

Tomlinson, I.M. (1997). V Base database of human antibody genes. Medical Research Council, Centre for Protein Engineering, UK Confirmation No. 149990 http://www.mrc-cpe.cam.ac.uk/.

Tuerk, C. and Gold, L., "Systematic Evolution of Ligands by Exponential Enrichment: RNA Ligands to Bacteriophage T4 DNA Polymerase," Science 249:505-510 (1990).

Wabl, M. et al., "Hypermutation at the immunoglobulin heavy chain locus in a pre-B-cell line," PNAS USA 82:479-482 (1985).

Wagner, S.D. et al., "Codon bias targets mutation," Nature 376:732 (1995).

Weill, J.C. and Reynaud, C.A., "Rearrangement/hypermutaiton/gene conversion: when, where and why?" Immunol. Today 17:92-97 (1996).

Wilson, P.C. et al., "Somatic hypermutation introduces insertions and deletions into immunoglobulin V genes," J. Exp. Med. 187:59-70 (1998).

Wu, H. and Kaartinen, M., "The Somatic Hypermutation Activity of Follicular Lymphoma Links to Large Insertions and Deletions of Immunoglobulin Genes," Scand. J. Immunol. 42:52-59 (1995).

Wu, H. et al., "A human follicular lymphoma B cell line hypermutates its functional immunoglobulin genes in vitro," Eur. J. Immunol. 25:3263-3269 (1995).

Yamaguchi-Iwai, Y. et al., "Homologous recombination, but not DNA repair, is reduced in vertebrate cells deficient in RAD52," Mol. Cell Biol. 1:6430-6435 (1998).

Yelamos, J. et al., "Targeting of non-Ig sequences in place of the V segment by somatic hypermutation," Nature 376:225-229 (1995).

Zhang, L. et al., "The development of anti-CD79 monoclonal antibodies for treatment of B-cell neoplastic disease," Ther. Immunol. 2:191-202 (1995).

Zhu, M. et al., "A well-differentiated B cell line is permissive for somatic mutation of a transfected immunoglobuin heavy-chain gene," PNAS USA 92:2810-2814 (1995).

Zou, X, et al., "Subtle differences in antibody responses and hypermutation of λ light chains in mice with a disrupted χ constant region," Eur. J. Immunol. 25:2154-2162 (1995).

Andersson, K. et al., "Affinity selection and repertoire shift: paradoxes as a consequence of somatic mutation?" Immunological Reviews 162:173-182 (1998).

Azuma, T., "Somatic hypermutation in mouse λ chains," Immunological Reviews 162:97-105 (1998).

Blanden, R. et al., "The signature of somatic hypermutation appears to be written into the germline IgV segment repertoire," Immunological Reviews 162:117-132 (1998).

Diaz, M. and Ficjnik, M., "Evolution of somatic hypermutation and gene conversion in adaptive immunity," Immunological Reviews 162:13-24 (1998).

Dorner, T. et al., "Analysis of the targeting of the hypermutational chemistry and theimpact of subsequent selection on the distribution of nucleotide changes in human $V_H DJ_H$ rearrangements," Immunological Reviews 162:161-171 (1998).

Green, N. et al., "Immunoglobulin hypermutation in cultured cells," Immunological Reviews 162:77-87 (1998).

Hsu, E., "Mutation, selection, and memory in B lymphocytes of exothermic vertebrates," Immunological Reviews 162:25-36 (1998).

Klein, U. et al., "Somatic hypermutation in normal and transformed human B cells," Immunological Reviews 162:261-280 (1998).

Knight, K. and Barrington, R., "Somatic diversifictaion of IgH genes in rabbit," Immunological Reviews 162:37-47 (1998).

Kong, Q. et al., "Recombination-based mechanisms for somatic hypermutation," Immunological Reviews 162:67-76 (1998).

Kosmas, C. et al., "Somatic hypermutation of immunoglobulin variable region genes: focus on follicular lymphoma and multiple myeloma," Immunological Reviews 162:281-292 (1998).

Lopez, O. et al., "A single $V_H$ family and long CDR3s are the targets for hypermutation in bovine immunoglobulin heavy chains," Immunological Reviews 162:55-66 (1998).

Mage, R., "Diversification of rabbit $V_H$ genes by gene-conversion-like and hypermutation mechanisms," Immunological Reviews 162:49-54 (1998).

Manser, T. et al., "The roles of antibody variable region hypermutation and selection in the development of the memory B-cell compartment," Immunological Reviews 162:183-196 (1998).

McIntosh, R. et al., "Somatic hypermutation in autoimmune thyroid disease," Immunological Revies 162:219-231 (1998).

Neuberger, M. et al., "Monitoring and interpreting the intrinsic features of somatic hypermutation," Immunological Reviews 162:107-116 (1998).

Ng, V. and McGrath, M., "The immunology of AIDS-associated lymphomas," Immunological Reviews 162:293-298 (1998).

Song, H. et al., "Antibody feedback and somatic mutation in B cells: regulation of mutation by immune complexes with IgG antibody," Immunological Reviews 162:211-218 (1998).

Stevenson, F. et al., "Insight into the origin and clonal history of B-cell tumors as revealed by anaylsis of immunoglobulin variable region genes," Immunological Reviews 162:247-259 (1998).

Storb, U., "Progress in understanding the mechanism and consequences of somatic hypermutation," Immunological Reviews 162:5-11 (1998).

Slorb et al., "Cis-acting sequences that affect somatic hypermutation of Ig genes," Immunological Reviews 162:153-160 (1998).

Wiens, G. et al., "Harmful somatic mutations: lessons from the dark side," Immunological Reviews 162:197-209 (1998).

Wilson, P. et al., "Amino acid insertions and deletions contribute to diversify the human Ig repertoire," Immunological Reviews 162:143-151 (1998).

Winter, D. and Gearhart, P., "Dual enigma of somatic hypermutation of immunoglobulin variable genes: targeting and mechanism," Immunological Reviews 162:89-96 (1998).

Wysocki, L. et al., "Somatic origin of T-cell epitopes within antibody variable regions: significance to monoclonal therapy and genesis of systemic autoimmune disease," Immunological Reviews 162:233-246 (1998).

Zheng, B. et al., "Immunoglobulin gene hypermutation in germinal centers is independent of the RAG-1 V(D)J recominase," Immunological Reviews 162:133-141 (1998).

Mage, Diversification of a Rabbit $V_H$ Genes by Gene-Conversion-Like and Hypermutation Mechanisms, *Immunogical Review*, vol. 162, Apr. 1998, pp. 49-54.

International Search Report PCT/GB02/02688, 2003.

* cited by examiner

C

In Frame Vλ  Out of Frame Vλ

A
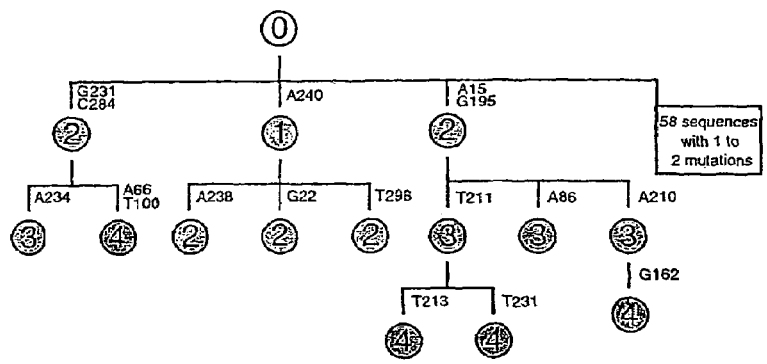
B
Clone Rc13
$0.24 \times 10^{-4}$ mutn.bp$^{-1}$.div$^{-1}$
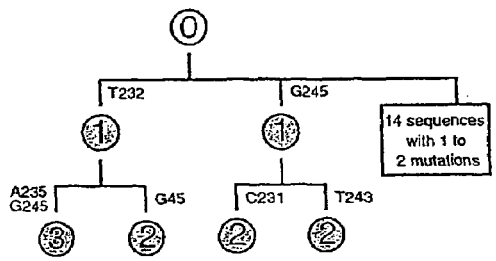
Clone Rc14
$0.22 \times 10^{-4}$ mutn.bp$^{-1}$.div$^{-1}$
Clone Rc1
$0.27 \times 10^{-4}$ mutn.bp$^{-1}$.div$^{-}$
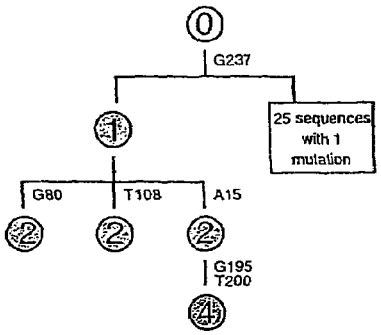
FIG. 2

FIG. 6

```
1/1
TGG GGC GCA GGA CTG TTG AAG CCT TCG GAG ACC CTG TCC CTC ACC TGC GGT GTT TAT GGT
 W   G   A   G   L   L   K   P   S   E   T   L   S   L   T   C   G   V   Y   G

61/21
GGG TCC TTC AGT GGT TAC TAC TGG AGC TGG ATC CGC CAG CCC CCA GGG AAG GGG CTG GAG
 G   S   F   S   G   Y   Y   W   S   W   I   R   Q   P   P   G   K   G   L   E
                         AGT
                          S

121/41
TGG ATT GGG GAA ATC AAT CAT AGT GGA AGC ACC AAC TAC AAC CCG TCC CTC AAG AGT CGA
 W   I   G   E   I   N   H   S   G   S   T   N   Y   N   P   S   L   K   S   R

151/51

181/61
GTC ACC ATA TCA GTA GAC ACG TCC AAG AAG CAG CTC TCC CTG AAG TTG AGC TCT GTG AAC
 V   T   I   S   V   D   T   S   K   K   Q   L   S   L   K   L   S   S   V   N
ATC                                      CAC
 M                                        H

211/71

241/81
GCC GCG GAC ACG GCT GTG TAT TAC TGT GCG AGA GTT ATT ACT AGG GCG AGT CCT GGA ACA
 A   A   D   T   A   V   Y   Y   C   A   R   V   I   T   R   A   S   P   G   T
    TCG                                                      ACG         CAT GGC
     S                                                        T           H   G

271/91

301/101
GAC GGG AGG TAC GGT ATG GAC GTC TGG GGC CAA GGG ACC ACG
 D   G   R   Y   G   M   D   V   W   G   Q   G   T   T
                         GTT
                          V

1/1                                                                                          31/11
TGG GGC GCA GGA CTG TTG AAG CCT TCG GAG ACC CTG TCC CTC ACC TGC GGT GTT TAT GGT
 W   G   A   G   L   L   K   P   S   E   T   L   S   L   T   C   G   V   Y   G

61/21                                                                                        91/31
GGG TCC TTC AGT GGT TAC TAC TGG AGC TGG ATC CGC CAG CCC CCA GGG AAG GGG CTG GAG
 G   S   F   S   G   Y   Y   W   S   W   I   R   Q   P   P   G   K   G   L   E
                             AGT
                              S
                             ATT
                              I

121/41                                                                                       151/51
TGG ATT GGG GAA ATC AAT CAT AGT GGA AGC ACC AAC TAC AAC CCG TCC CTC AAG AGT CGA
 W   I   G   E   I   N   H   S   G   S   T   N   Y   N   P   S   L   K   S   R

181/61                                                                                       211/71
GTC ACC ATA TCA GTA GAC ACG TCC AAG AAG CAG CTC TCC CTG AAG TTG AGC TCT GTG AAC
 V   T   I   S   V   D   T   S   K   K   Q   L   S   L   K   L   S   S   V   N
                                             CAC                     AAC
                                              H                       N

241/81                                                                                       271/91
GCC GCG GAC ACG GCT GTG TAT TAC TGT GCG AGA GTT ATT ACT AGG GCG AGT CCT GGA ACA
 A   A   D   T   A   V   Y   Y   C   A   R   V   I   T   R   A   S   P   G   T

301/101                                                                                      331/111
GAC,GGG,AGG TAC GGT ATG GAC GTC TGG GGC CAA GGG ACC ACG
 D   G   R   Y   G   M   D   V   W   G   Q   G   T   T
 AGC
  S

VL

1/1
CCT GCC TCC GTG TCT GGG TCT CCT GGA CAG TCG ATC ACC ATC TCC TGC ACT GGA ACC AGC
P    A    S    V    S    G    S    P    G    Q    S    I    T    I    S    C    T    G    T    S
                                                    TAT
                                                    Y

61/21
AGT GAC GTT GGT GGT TAT AAC TAT GTC TCC TGG TAC CAA CAA CCA GGC AAA GCC CCC
S    D    V    G    G    Y    N    Y    V    S    W    Y    Q    Q    P    G    K    A    P
TTT TGT
F    C

121/41
AAA CTC ATG ATT TAT GAT GTC AGT AAT CGG CCC TCA GGG ATT TCT AAT CGC TTC TCT GGC
K    L    M    I    Y    D    V    S    N    R    P    S    G    I    S    N    R    F    S    G
                              AAT                                                  CGA TTA
                              N                                                    R    L

181/61
TCC AAG TCT GGC AAC ACG GCC TCC CTG ACC ATC TCT GGG CTC CAG GCT GAC GAC GAG GCT
S    K    S    G    N    T    A    S    L    T    I    S    G    L    Q    A    D    D    E    A
                                                  ATC
                                                  I

241/81
GAT TAT TAC TGC ACC TCA TAT ACA AAC GAC AGC AAT TCT CAG GTA TTC GGC GGA GGG ACC
D    Y    Y    C    T    S    Y    T    N    D    S    N    S    Q    V    F    G    G    G    T
                              ACT
                              T

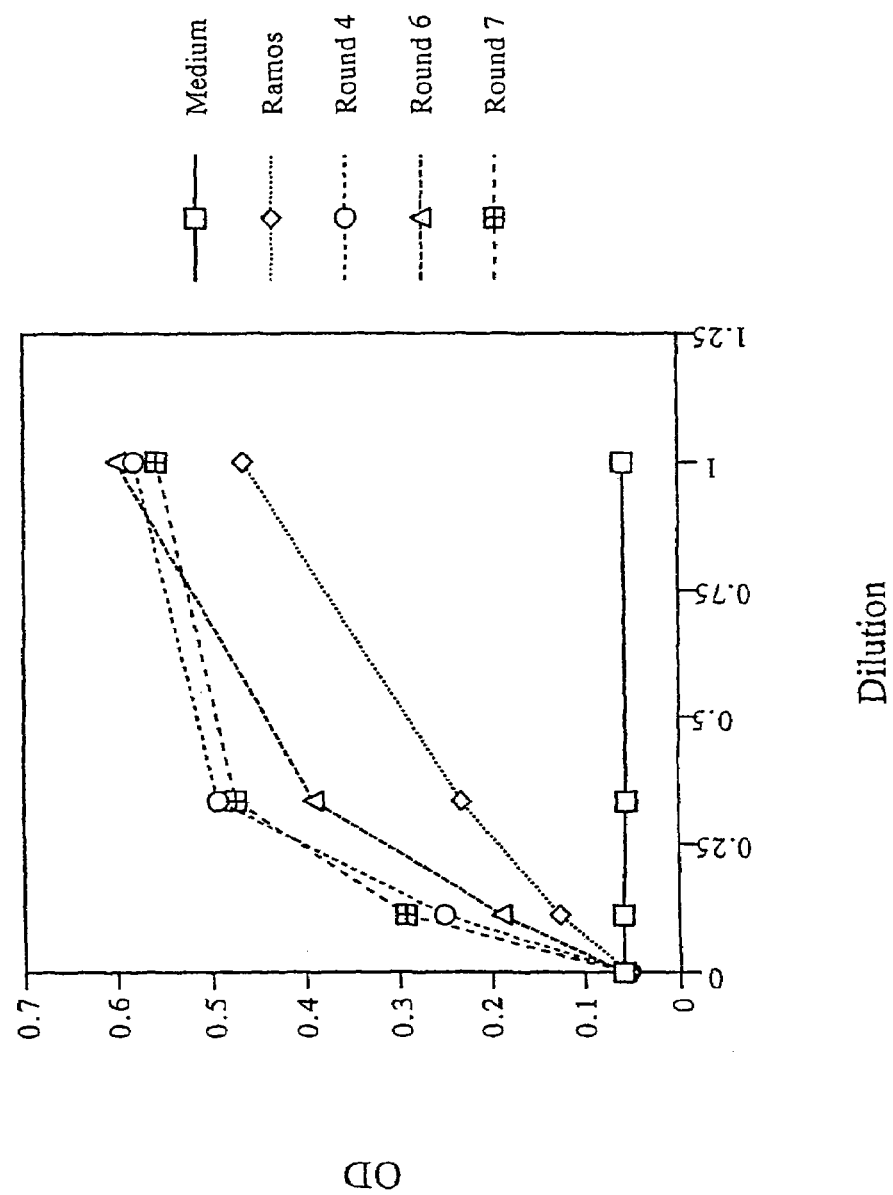

Streptavidin binding of Supernatants: ELISA

Streptavidin binding of Supernatants: Biacore

1/1
TGG GGC GCA GGA CTG TTG AAG CCT TCG GAG ACC CTG TCC CTC ACC TGC GGT GTT TAT GGT
 W   G   A   G   L   L   K   P   S   E   T   L   S   L   T   C   G   V   Y   G

31/11

61/21      CDR1                                               91/31
GGG TCC TTC AGT GGT TAC TAC TGG AGC TGG ATC CGC CAG CCC CCA GGG AAG GGG CTG GAG
 G   S   F   S   G   Y   Y   W   S   W   I   R   Q   P   P   G   K   G   L   E

121/41   CDR2                                                 151/51
TGG ATT GGG GAA ATC AAT CAT AGT GGA AGC AAC TAC AAC CCG TCC CTC AAG AGT CGA
 W   I   G   E   I   N   H   S   G   S   N   Y   N   P   S   L   K   S   R

181/61
GTC ACC ATA TCA GTA GAC ACG TCC AAG AAG CAG CTC TCC CTG AAG TTG AGC TCT GTG AAC
 V   T   I   S   V   D   T   S   K   K   Q   L   S   L   K   L   S   S   V   N

211/71

241/81                                                        271/91  DJ
GCC GCG GAC ACG GCT GTG TAT TAC TGT GCG AGA GTT ATT ACT AGG GCG AGT CCT GGA ACA
 A   A   D   T   A   V   Y   Y   C   A   R   V   I   T   R   A   S   P   G   T

301/101                                                       331/111
GAC GGG AGG TAC GGT ATG GAC GTC TGG GGC CAA GGG ACC ACG
 D   G   R   Y   G   M   D   V   W   G   Q   G   T   T
 AGC
  S

VL

1/1
CCT GCC TCC GTG TCT CCT GGG TCT CCT GGA CAG TCG ATC ACC ATC TCC TGC ACT GGA ACC AGC
 P   A   S   V   S   P   G   S   P   G   Q   S   I   T   I   S   C   T   G   T   S

31/11
                                                                       CDR1

61/21
AGT GAC GTT GGT GGT TAT AAC TAT GTC TCC TGG TAC CAA CAA AAC CCA GGC AAA GCC CCC
 S   D   V   G   G   Y   N   Y   V   S   W   Y   Q   Q   N   P   G   K   A   P
         TTT TGT
          F   C

91/31

121/41
AAA CTC ATG ATT TAT GAT GTC AGT AAT CGG CCC TCA GGG ATT TCT AAT CGC TTC TCT GGC
 K   L   M   I   Y   D   V   S   N   R   P   S   G   I   S   N   R   F   S   G
                 GCT
                  A
                     CDR2
                                     151/51

181/61
TCC AAG TCT GGC AAC ACG GCC TCC CTG ACC ATC TCT GGG CTC CAG GCT GAC GAC GAG GCT
 S   K   S   G   N   T   A   S   L   T   I   S   G   L   Q   A   D   D   E   A

211/71

241/81
GAT TAT TAC TGC ACC TCA TAT ACA AAC AGC AAT TCT CAG GTA TTC GGC GGA GGG ACC
 D   Y   Y   C   T   S   Y   T   N   S   N   S   Q   V   F   G   G   G   T
             CDR3
                             271/91

FIG. 16CONT'D

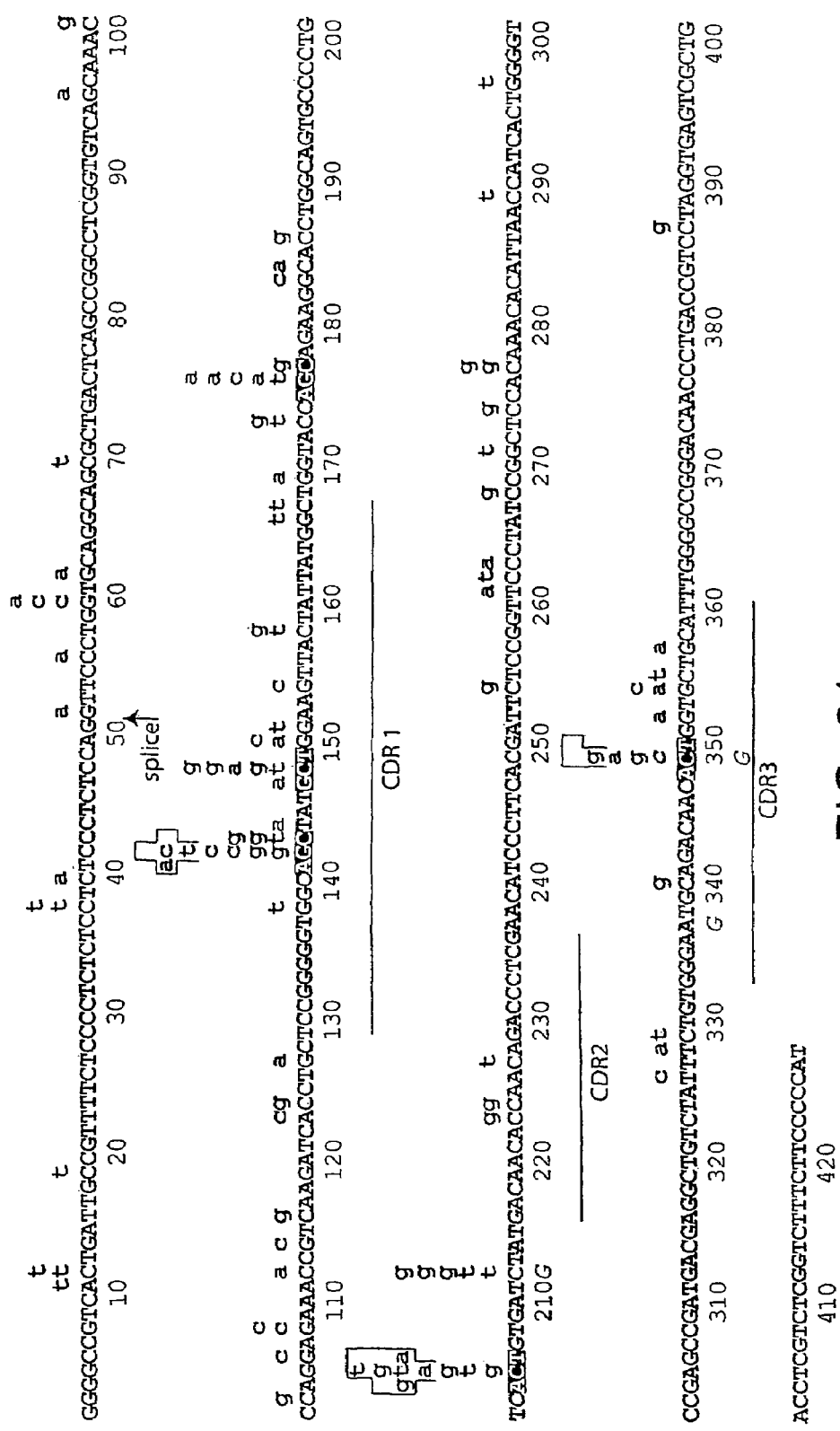
FIG. 21 CONT D

Heavy chain

```
              17 19          31              42        54 57  DNGSDTRYAPAVKGRATISRDNGQSTVRLQ    77 80          102 105
              |  |           |               |         |  |                                    |  |           |   |
P0         // PGGALSLV     // STNAMGWVRQAPDK //        DNGSDTRYAPAVKGRATISRDNGQSTVRLQ       // AYISGYDY //
P4         // ...P.R..     // ..............  //       .D............................       // ......C. //
P6         // ...P.R..     // .S............  //       .D............................ R..   // ......C. //
P8,9,10    // ...P.R..     // .S............G //       .D.G..........................R..S.  // ...S..C. //
P14        // ...P.R..     // .S.............  //      .D.G......................V...R..S.  // ...S..C. //
                            |—CDR1—|                   |————CDR2————|
```

Light chain

```
                          10              25 28 33                        46                              94
                          |               |  |  |                         |                               |
P0        // ASVSVNPGETVKITCSGGGSYGGSYYYGWYQQKAPGSAPVSVI  //  DDEAVYFCGNADNSGAAFGA //
P4,6      // ................................R.A.......  //  .........T.......... //
P8        // .........A......................R.A...V...  //  .........T.......... //
P9,10,14  // .........A......................R.A...V.T.  //  .........T.......... //
                          |————CDR1————|                                  |—CDR3—|
```

FIG. 26CONT'D

METHOD FOR GENERATING DIVERSITY

This application is a continuation of International application number PCT/GB02/02688, filed Jun. 11, 2002, which claims priority to U.S. application Ser. Nos. 10/146,505, filed May 15, 2002, now U.S. Pat. No. 7,122,339, and 09/879,813, filed Jun. 11, 2001, now abandoned, all of which are incorporated herein by reference in their entirety.

The present invention relates to a method for generating diversity in a gene or gene product by exploiting the natural somatic hypermutation capability of antibody-producing cells, as well as to cell lines capable of generating diversity in defined gene products.

Many in vitro approaches to the generation of diversity in gene products rely on the generation of a very large number of mutants which are then selected using powerful selection technologies. For example, phage display technology has been highly successful as providing a vehicle that allows for the selection of a displayed protein (Smith, 1985; Bass et al., 1990; McCafferty et al., 1990; for review see Clackson and Wells, 1994). Similarly, specific peptide ligands have been selected for binding to receptors by affinity selection using large libraries of peptides linked to the C terminus of the lac repressor LacI (Cull et al., 1992). When expressed in *E. coli* the repressor protein physically links the ligand to the encoding plasmid by binding to a lac operator sequence on the plasmid. Moreover, an entirely in vitro polysome display system has also been reported (Mattheakis et al., 1994) in which nascent peptides are physically attached via the ribosome to the RNA which encodes them.

In vivo the primary repertoire of antibody specificities is created by a process of DNA rearrangement involving the joining of immunoglobulin V, D and J gene segments. Following antigen encounter in mouse and man, the rearranged V genes in those B cells that have been triggered by the antigen are subjected to a second wave of diversification, this time by somatic hypermutation. This hypermutation generates the secondary repertoire from which good binding specificities can be selected thereby allowing affinity maturation of the humoral immune response.

Artificial selection systems to data rely heavily on initial mutation and selection, similar in concept to the initial phase of V-D-J rearrangement which occurs in natural antibody production, in that it results in the generation of a "fixed" repertoire of gene product mutants from which gene products having the desired activity may be selected.

In vitro RNA selection and evolution (Ellington and Szostak, 1990), sometimes referred to as SELEX (systematic evolution of ligands by exponential enrichment) (Tuerk and Gold, 1990) allows for selection for both binding and chemical activity, but only for nucleic acids. When selection is for binding, a pool of nucleic acids is incubated with immobilised substrate. Non-binders are washed away, then the binders are released, amplified and the whole process is repeated in iterative steps to enrich for better binding sequences. This method can also be adapted to allow isolation of catalytic RNA and DNA (Green and Szostak, 1992; for reviews see Chapman and Szostak, 1994; Joyce, 1994; Gold et al., 1995; Moore, 1995). SELEX, thus, permits cyclical steps of improvement of the desired activity, but is limited in its scope to the preparation of nucleic acids.

Unlike in the natural immune system, however, artificial selection systems are poorly suited to any facile form of "affinity maturation", or cyclical steps of repertoire generation and development. One of the reasons for this is that it is difficult to target mutations to regions of the molecule where they are required, so subsequent cycles of mutation and selection do not lead to the isolation of molecules with improved activity with sufficient efficiency.

Much of what is known about the somatic hypermutation process which occurs during affinity maturation in natural antibody production has been derived from an analysis of the mutations that have occurred during hypermutation in vivo (for reviews see Neuberger and Milstein, 1995; Weill and Reynaud, 1996; Parham, 1998). Most of these mutations are single nucleotide substitutions which are introduced in a stepwise manner. They are scattered over the rearranged V domain, though with characteristic hotspots, and the substitutions exhibit a bias for base transitions. The mutations largely accumulate during B cell expansion in germinal centres (rather than during other stages of B cell differentiation and proliferation) with the rate of incorporation of nucleotide substitutions into the V gene during the hypermutation phase estimated at between $10^{-4}$ and $10^{-3}$ $bp^{-1}$ generation$^{-1}$ (McKean et al., 1984; Berek & Milstein, 1988)

The possibility that lymphoid cell lines could provide a tractable system for investigating hypermutation was considered many years ago (Coffino and Scharf, 1971; Adetugbo et al., 1977; Brüggemann et al., 1982). Clearly, it is important that the rate of V gene mutation in the cell-line under study is sufficiently high not only to provide a workable assay but also to be confident that mutations are truly generated by the localised antibody hypermutation mechanism rather than reflecting a generally increased mutation rate as is characteristically associated with many tumours. Extensive studies on mutation have been performed monitoring the reversion of stop codons in $V_H$ in mouse pre-B and plasmacytoma cell lines (Wabl et al., 1985; Chui et al., 1995; Zhu et. al., 1995; reviewed by Green et al., 1998). The alternative strategy of direct sequencing of the expressed V gene has indicated that $V_H$ gene diversification in several follicular, Burkitt and Hodgkin lymphomas can continue following the initial transformation event (Bahler and Levy, 1992; Jain et al., 1994; Chapman et al., 1995 and 1996; Braeuninger et al., 1997). Direct sequencing has also revealed a low prevalence of mutations in a cloned follicular lymphoma line arguing that $V_H$ diversification can continue in vitro (Wu et al., 1995). None of the reports of constitutive mutation in cell lines cited above provides evidence that the mutations seen are the result of directed hypermutation, as observed in natural antibody diversification, which is concentrated in the V genes, as opposed to a general susceptibility to mutation as described in many tumour cell lines from different lineages.

Recently, hypermutation has been induced in a cell line by Denepoux et al. (1997), by culturing cells in the presence of anti-immunoglobulin antibody and activated T-cells. However, the hypermutation observed was stated to be induced, not constitutive.

SUMMARY OF THE INVENTION

In a first aspect of the invention there is provided a method for preparing a lymphoid cell line capable of directed constitutive hypermutation of a target nucleic acid region, comprising screening a cell population for ongoing target sequence diversification, and selecting a cell in which the rate of target nucleic acid mutation exceeds that of other nucleic acid mutation by a factor of 100 or more.

As used herein, "directed constitutive hypermutation" refers to the ability, observed for the first time in experiments reported herein, of certain cell lines to cause alteration of the nucleic acid sequence of one or more specific sections of endogenous or transgene DNA in a constitutive manner, that is without the requirement for external stimulation. In cells capable of directed constitutive hypermutation, sequences outside of the specific sections of endogenous or transgene DNA are not subjected to mutation rates above background mutation rates.

A "target nucleic acid region" is a nucleic acid sequence or region in the cell according to the invention which is subjected to directed constitutive hypermutation. The target nucleic acid may comprise one or more transcription units encoding gene products, which may be homologous or heterologous to the cell. Exemplary target nucleic acid regions are immunoglobulin V genes as found min immunoglobulin-producing cells These genes are under the influence of hypermutation-recruiting elements, as described further below, which direct the hypermutation to the locus in question. Other target nucleic acid sequences may be constructed, for example by replacing V gene transcription units in loci which contain hypermutation-recruiting elements with another desired transcription unit, or by constructing artificial genes comprising hypermutation-recruiting elements.

"Hypermutation" refers to the mutation of a nucleic acid in a cell at a rate above background. Preferably, hypermutation refers to a rate of mutation of between $10^{-5}$ and $10^{-3}$ $bp^{-1}$ $generation^{-1}$. This is greatly in excess of background mutation rates, which are of the order of $10^{-9}$ to $10^{-10}$ mutations $bp^{-1}$ $generation^{-1}$ (Drake et al., 1988) and of spontaneous mutations observed in PCR. 30 cycles of amplification with Pfu polymerase would produce $<0.05 \times 10^{-3}$ mutations $bp^{-1}$ in the product, which in the present case would account for less than 1 in 100 of the observed mutations (Lundberg et al., 1991).

Hypermutation is a part of the natural generation of immunoglobulin variable chain (V) genes. According to the present invention therefore, the cell line is preferably an immunoglobulin-producing cell line which is capable of producing at least one immunoglobulin V gene. A V gene may be a variable light chain ($V_L$) or variable heavy chain ($V_H$) gene, and may be produced as part of an entire immunoglobulin molecule; it may be a V gene from an antibody, a T-cell receptor or another member of the immunoglobulin superfamily. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor). Thus preferred cell lines according to the invention are derived from B-cells. According to the present invention, it has been determined that cell lines derived from antibody-producing B cells may be isolated which retain the ability to hypermutate V region genes, yet do not hypermutate other genes.

In a preferred embodiment, the cells according to the invention are derived from or related to cells which hypermutate in vivo. Cells which hypermutate in vivo are, for example, immunoglobulin-expressing cells, such as B-cells. Lymphoma cells, which are Ig-expressing cell tumours, are particularly good candidates for the isolation of constitutively hypermutating cell lines according to the present invention.

As used herein, "screening for ongoing target sequence diversification" refers to the determination of the presence of hypermutation in the target nucleic acid region of the cell lines being tested. This can be performed in a variety of ways, including direct sequencing or indirect methods such as the MutS assay (Jolly et al., 1997) or monitoring the generation of immunoglobulin loss variants. Cells selected according to this procedure are cells which display target sequence diversification.

The cell population which is subjected to selection by the method of the invention may be a polyclonal population, comprising a variety of cell types and/or a variety of target sequences, or a (mono-) clonal population of cells.

A clonal cell population is a population of cells derived from a single clone, such that the cells would be identical save for mutations occurring therein. Use of a clonal cell population preferably excludes co-culturing with other cell types, such as activated T-cells, with the aim of inducing V gene hypermutation.

Cells according to the invention do not rely on the use of induction steps in order to produce hypermutation.

Preferably, the clonal cell population screened in the present invention is derived from a B cell. Advantageously it is a lymphoma cell line, such as a Burkitt lymphoma cell line, a follicular lymphoma cell line or a diffuse large cell lymphoma cell line.

Preferably, the method according to the invention further comprises the steps of isolating one or more cells which display target sequence diversification, and comparing the rate of accumulation of mutations in the target sequences with that in non-target sequences in the isolated cells.

A feature of the present invention is that the hypermutation is directed only to specific (target) nucleic acid regions, and is not observed outside of these regions in a general manner. Specificity is thus assayed as part of the method of the invention by assaying the rate of mutation of sequences other than target sequences. C region genes, which are not naturally exposed to hypermutation, may advantageously be employed in such a technique, although any other nucleic acid region not subject to specific hypermutation may also be used. Since hypermutation is not sequence dependent, the actual sequence of the nucleic acid region selected for comparison purposes is not important. However, it must not be subject to control sequences which direct hypermutation, as described below. Conveniently, background mutation may be assessed by fluctuation analysis, for example at the HPRT locus [see Luria and Delbreck, (1943); Capizzi and Jameson, (1973)].

Cells in which target region mutation exceeds non-target region mutation are cells capable of directed constitutive hypermutation of a specific nucleic acid region in accordance with the present invention. The factor by which V region gene mutation exceeds other gene mutation is variable, but is in general of the order of at least $10^2$ advantageously $10^3$, and preferably $10^4$ or more.

Overall mutation rates and diversity may be increased, for example by the administration of mutagens or expression of sequence modifying genes, such as terminal deoxynucleotidyl transferase (TdT). However, the difference between hypermutation and background is not expected to be increased in such a manner.

Preferred cells according to the invention may be subject to gene manipulation, such as gene deletion, conversion or insertion, in order to increase the rate of somatic hypermutation observed therein. For example, the cells according to the invention may lack one or more copies of a RAD51 paralogue.

The cells may be any suitable vertebrate cells, including mammalian and avian cells.

In a second aspect of the present invention, there is provided a method for preparing a gene product having a desired activity, comprising the steps of:

a) expressing a nucleic acid encoding the gene product in a population of cells according to the first aspect of the present invention, operably linked to a nucleic acid which directs hypermutation;
b) identifying a cell or cells within the population of cells which expresses a mutant gene product having the desired activity; and
c) establishing one or more clonal populations of cells from the cell or cells identified in step (b), and selecting from said clonal populations a cell or cells which expresses a gene product having an improved desired activity.

The population of cells according to part a) above is derived from a clonal or polyclonal population of cells which comprises cells identified by a method according to the first aspect of the invention as being capable of constitutive hypermutation of V region genes. The gene product may thus be the endogenous immunoglobulin polypeptide, a gene product expressed by a manipulated endogenous gene or a gene product expressed by a heterologous transcription unit operatively linked to control sequences which direct somatic hypermutation, as described further below.

The nucleic acid which is expressed in the cells of the invention and subjected to hypermutation may be an endogenous region, such as the endogenous V region, or a heterologous region inserted into the cell line of the invention. This may take form, for example, of a replacement of the endogenous V region with heterologous transcription unit(s), such as a heterologous V region, retaining the endogenous control sequences which direct hypermutation; or of the insertion into the cell of a heterologous transcription unit under the control of its own control sequences to direct hypermutation, wherein the transcription unit may encode V region genes or any other desired gene product. The nucleic acid according to the invention is described in more detail below.

In step b) above, the cells are screened for the desired gene product activity. This may be, for example in the case of immunoglobulins, a binding activity. Other activities may also be assessed, such as enzymatic activities or the like, using appropriate assay procedures. Where the gene product is displayed on the surface of the cell, cells which produce the desired activity may be isolated by detection of the activity on the cell surface, for example by fluorescence, or by immobilising the cell to a substrate via the surface gene product. Where the activity is secreted into the growth medium, or otherwise assessable only for the entire cell culture as opposed to in each individual cell, it is advantageous to establish a plurality of clonal populations from step a) in order to increase the probability of identifying a cell which secretes a gene product having the desired activity. Advantageously, the selection system employed does not affect the cell's ability to proliferate and mutate.

Preferably, at this stage (and in step c) cells which express gene products having a better, improved or more desirable activity are selected. Such an activity is, for example, a higher affinity binding for a given ligand, or a more effective enzymatic activity. Thus, the method allows for selection of cells on the basis of a qualitative and/or quantitative assessment of the desired activity.

In a third aspect of the present invention, there is provided the use of a cell capable of directed constitutive hypermutation of a specific nucleic acid region in the preparation of a gene product having a desired activity.

In the use according to the invention, a nucleic acid encoding the gene product having the desired activity is operatively linked to control sequences which direct hypermutation within the cell. Successive generations of the cell thus produce mutants of the nucleic acid sequence, which are screened by the method of the invention to isolate mutants with advantageous properties.

In a further aspect, the invention relates to a cell capable of directed constitutive hypermutation in accordance with the invention. Preferably, the cell is a genetically manipulated chicken DT40 cell. As described above, one or more DNA-repair genes may be manipulated. Preferably, one or more Rad51 genes are manipulated. Advantageously, the genes are downregulated or deleted. Preferably, the genes are Rad51b or Rad51c genes.

In a highly preferred embodiment, the invention provides a cell selected from the group consisting of Δ xrcc2 DT40 and Δ xrcc3 DT40

BRIEF DESCRIPTION OF THE FIGURES

FIG. 2 Constitutive $V_H$ diversification in Ramos.
(A) Diversification assessed by a MutS assay: The mutation prevalence in each population as deduced by direct cloning and sequencing is indicated.
(B) Dynastic relationships deduced from the progeny of three independent. Ramos clones.
FIG. 6. Sequence table summarizing mutations in $V_H$ other than single nucleotide substitutions. The mutations are:

Figure 1:
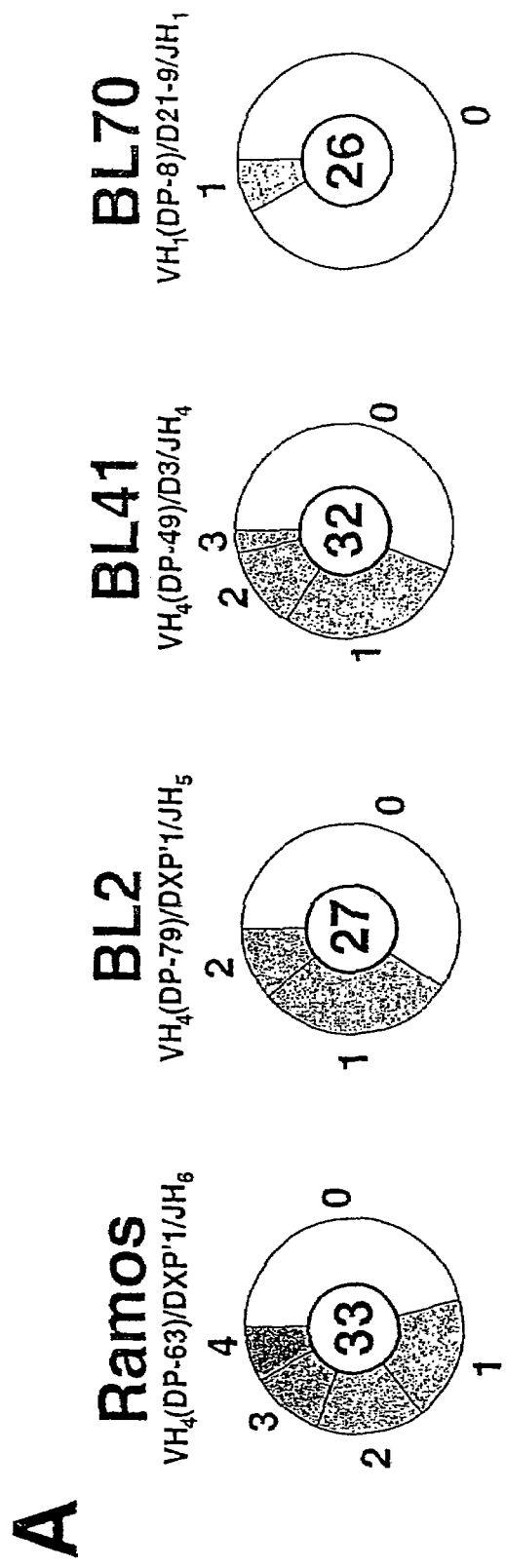
FIG. 1 $V_H$ diversity in Burkitt lines.
(A) Sequence diversity in the rearranged $V_H$ genes of four sporadic Burkitt lymphoma lines, shown as pie charts. The number of M13 clones sequenced for each cell line is denoted in the centre of the pie; the sizes of the various segments depict the proportion of sequences that are distinguished by 0, 1, 2 etc. mutations (as indicated) from the consensus.
(B) Presumed dynastic relationship of $V_H$ mutations identified in the initial Ramos culture. Each circle (with shading proportional to extent of mutation) represents a distinct sequence with the number of mutations accumulated indicated within the circle.
(C) Mutation prevalence in the rearranged $V_\lambda$ genes. Two $V_\lambda$ rearrangements are identified in Ramos. Diversity and assignment of germline origin is presented as in FIG. 1A.
(D) Comparison of mutation prevalence in the $V_H$ and Cμ regions of the initial Ramos culture. Pie charts are presented as in FIG. 1A.
Figure 1:
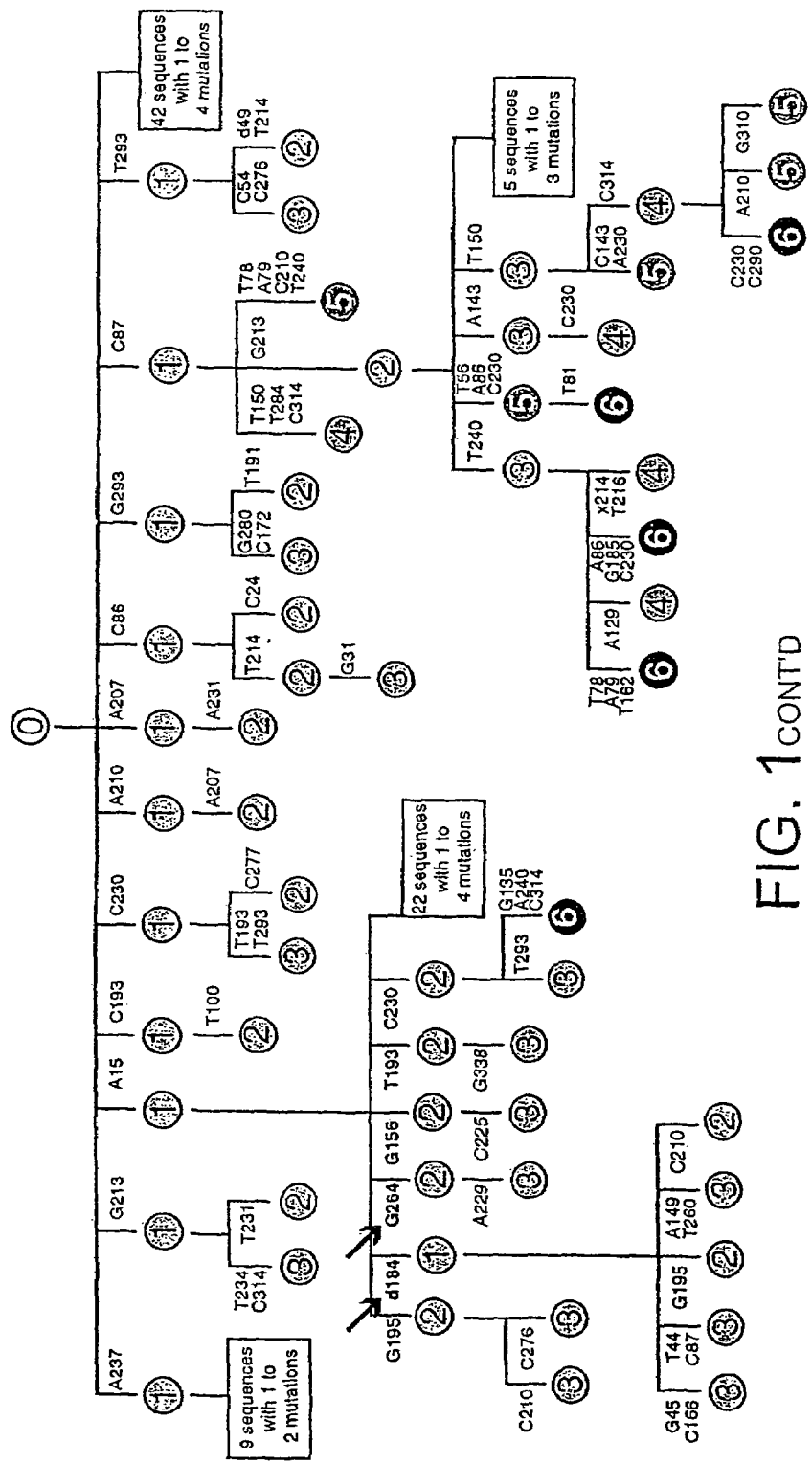

| | | |
|---|---|---|
| A62 | GGTCCT^(TCAGTGG)TTACTA | (SEQ ID NO:16) |
| A120 | GTGGAT^(T)GGGGAA | (SEQ ID NO:17) |
| A276 | TATTAC^(TGTG.18bp.TACT)AGGGGG | (SEQ ID NO:18) |
| A306 | GAGGTA^(C)GGTATG | (SEQ ID NO:19) |
| B93 | CCGCCA^(G)CCCCA | (SEQ ID NO:20) |
| B98 | AGCCC^(C)AGGGAA | (SEQ ID NO:21) |
| B227 | TGAGCT^(CTGTC)AACGCC | (SEQ ID NO:22) |
| C82 | TGGAGT^(TGGA.37bpGAGT)GGATTG | (SEQ ID NO:23) |
| C209 | AGCACC^(TCTTCCCTGAAGTT)GAGCTC | (SEQ ID NO:24) |
| C187 | ATATCA^(GTACACACGTCCAAGA)AGCACC | (SEQ ID NO:25) |
| U26 | CGGAGA^(CC)CTGCC | (SEQ ID NO:26) |
| U199 | ACGTCC^(AAG)AAGCAC | (SEQ ID NO:27) |
| U208 | AAGCAG^(C)TTTCTC | (SEQ ID NO:28) |
| U268 | GCGAGA^(GTTATTA)CTAGGG | (SEQ ID NO:29) |
| A255 | ^(TGTGCGAGAGTTATTA)CGAGAGTTATTA^(CTAGGG) | (SEQ ID NO:30) |
| A113 | ^(GGCTGGAGTGGATTGGG.62bp.TATC)AGTGGATTGGG.62bp.TATC^(AGTAGA) | (SEQ ID NO:31) |
| U43 | ^(ACCTGCGGTGTTTAT)GGTGTTTAT^(GGTGGG) | (SEQ ID NO:32) |
| U318 | ^(GGACGTCTGGGGCCA)ACGTCTGGGGCCA^(AGGGAC) | (SEQ ID NO:33) |
| D27 | GGAGAC^(CCTCA)CCTGCG | (SEQ ID NO:34) |
| D31 | ACCCTC^(A)CCTGCG | (SEQ ID NO:35) |
| D219 | CCTGAA^(G)TTGAGC | (SEQ ID NO:36) |
| D150 | CACCAA^(C)TACAAC | (SEQ ID NO:37) |
| D109 | AAGGGG^(C)TGGAGT | (SEQ ID NO:38) |
| E28 | CCCTCA^(CCTGC)GGTGTT | (SEQ ID NO:39) |
| E81 | CTGGAG^(TTGGA..37bp..TGGAG)TGGATT | (SEQ ID NO:40) |
| E88 | TGGATC^(CGCC)AGCCCC | (SEQ ID NO:41) |
| E92 | CGCCA^(G)CCCCCA | (SEQ ID NO:42) |
| E136 | AATCAT^(AGTGGAAGCACCAACTA)CAACCC | (SEQ ID NO:43) |
| F66 | CTTCAC^(TGGTTACTACT)GGAGTT | (SEQ ID NO:44) |
| F183 | TATCAT^(ATCAGTA)ACACGT | (SEQ ID NO:45) |
| F215 | TCTCCC^(TGAA.18bp.CGCC)GCGGAC | (SEQ ID NO:46) |
| F267 | TGCGAG^(AG)TTATTA | (SEQ ID NO:47) |
| D55 | ^(TATGGTGG.41bp.AGGG)GTGG.41bp.AGGG^(AAGG) | (SEQ ID NO:48) |
| D123 | ^(GATTGGGGAAATCAATCATAGTGGAAGC)GGAAATCAATCATAGGGAAGC^(ACCAAC) | (SEQ ID NO:49) |
| F85 | ^(AGTTGGAT.10bp.CCCA)GGAT.10bp.CCCA^(GGGA) | (SEQ ID NO:50) |
| D3 | GGTCGC^(AGGACTGT)TGAAGC<br>    GACCC | (SEQ ID NO:51) |
| D56 | ^(ATGGTGGG.50bp.CAGGG)GGTGGG.50bp.CAGGG^(AAGGGG) | (SEQ ID NO:52) |
| D71 | GTGGTT^(A)CTACTG<br>    GGG | (SEQ ID NO:53) |
| D75 | TTACTA^(C)TGGAGTT<br>    GG | (SEQ ID NO:54) |
| D126 | TGGGA^(AATCAATCAT)AGTGGA<br>    GGG | (SEQ ID NO:55) |
| D223 | AAGTTG ^(AG) CTCTGTG<br>    GACCCGGC | (SEQ ID NO:56) |
| D232 | ^(TCTGTGAACGCCGC)GCCCCCGTCCTGTGAACGCCGC^(GGACAC) | (SEQ ID NO:57) |
| D235 | ^(GTAAAC)GGAGG^(GCCGCG) | (SEQ ID NO:58) |
| D252 | GGCTGT^(GTATTACTGT)GCGAGA<br>       TAC | (SEQ ID NO:59) |
| D268 | GCGAGA^(GT)TATTATT<br>    AGG | (SEQ ID NO:60) |
| D275 | TTATTA^(C)TAGGGC<br>    GG | (SEQ ID NO:61) |
| D332 | AAGGGA^(C)CAC<br>    AG | (SEQ ID NO:62) |
| E3 | GGGCGC^(AGG.51bp.CTTC)AGTGGT<br>    GT | (SEQ ID NO:63) |
| E51 | TGTTA^(TGGT.15bp.TACT)ACTGGAG<br>    AGACC | (SEQ ID NO:64) |
| E80 | ACTGGA^(G)TTGGAT<br>    CCC | (SEQ ID NO:65) |
| E263 | ACTGTG^(CGAGAGTTATTACT)AGGGGG<br>    GGTG | (SEQ ID NO:66) |
| F89 | GGATCC^(GCCAGCCCCAGGG)AAGGGG<br>    AGG | (SEQ ID NO:67) |
| F168 | CCTCAA^(AGAGTCGAGT)CACCAT<br>    GGG | (SEQ ID NO:68) |

-continued

| | | |
|---|---|---|
| F195 | AGACAC$^{GTCCAAGAAG}_{AGGGC}$CACCTC | (SEQ ID NO:69) |
| F199 | ACGTCC$^{AAGAAG}_{CT}$ACCCTGA | (SEQ ID NO:70) |
| F242 | CCGCGG$^{ACACGGCTGTGTATTACTGT}_{GGA}$GCGAGA | (SEQ ID NO:71) |
| F260 | ATTACT$^{GTG}_{CGTGA}$CGAGAG | (SEQ ID NO:72) |
| F264 | CTGTGC$^{GAGAG.46bp.CGTC}_{ACA}$TGGGGC | (SEQ ID NO:73) |
| B123 | GATTGG$^G_A$AAATC | (SEQ ID NO:74) |
| C109 | AAGGGT$^C$TGGAGT | (SEQ ID NO:75) |
| A16 | $^{TTGAAGCCTTCGGACT}$GAAGCCTTCGGAGA$^{CCCTGT}$ | (SEQ ID NO:76) |
| U180 | $^{AGTCACCATATCAA}$ACCATATCAG$^{TAGACA}$ | (SEQ ID NO:77) |
| U45 | CTGCGCG$^{GTTTATGGTGGGT}$CCTTCA | (SEQ ID NO:78) |
| D164 | CGTCCCC$^{CAAG}$AGTCGA | (SEQ ID NO:79) |
| D216 | CTCCCTT$^{AAAG.22bp.CGGA}$CACGGC | (SEQ ID NO:80) |
| E11 | GACTGT$^T$AAAGCC | (SEQ ID NO:81) |
| E54 | TTATGGA$^{GGG.25bp.GTTG}$GATCCG | (SEQ ID NO:82) |
| F188 | TATCAGG$^{AGACACGTCCAGAA}$GCACCT | (SEQ ID NO:83) |
| F220 | CTGAAGC$^{TGAGCTCTGTG}$AACGCC | (SEQ ID NO:84). |

FIG. 7. Comparison of sequences isolated from VH genes of Ramos cells which have lost anti-idiotype (anti-Id1) binding specificity. Nucleotide substitutions which differ from the starting population consensus are shown in bold. Predicted amino acid changes are indicated, also in bold type. The nucleotide sequence and amino acid sequence of the VH Ramos gene depicted is SEQ ID NO: 15 and SEQ ID NO: 128.

Figure 8:
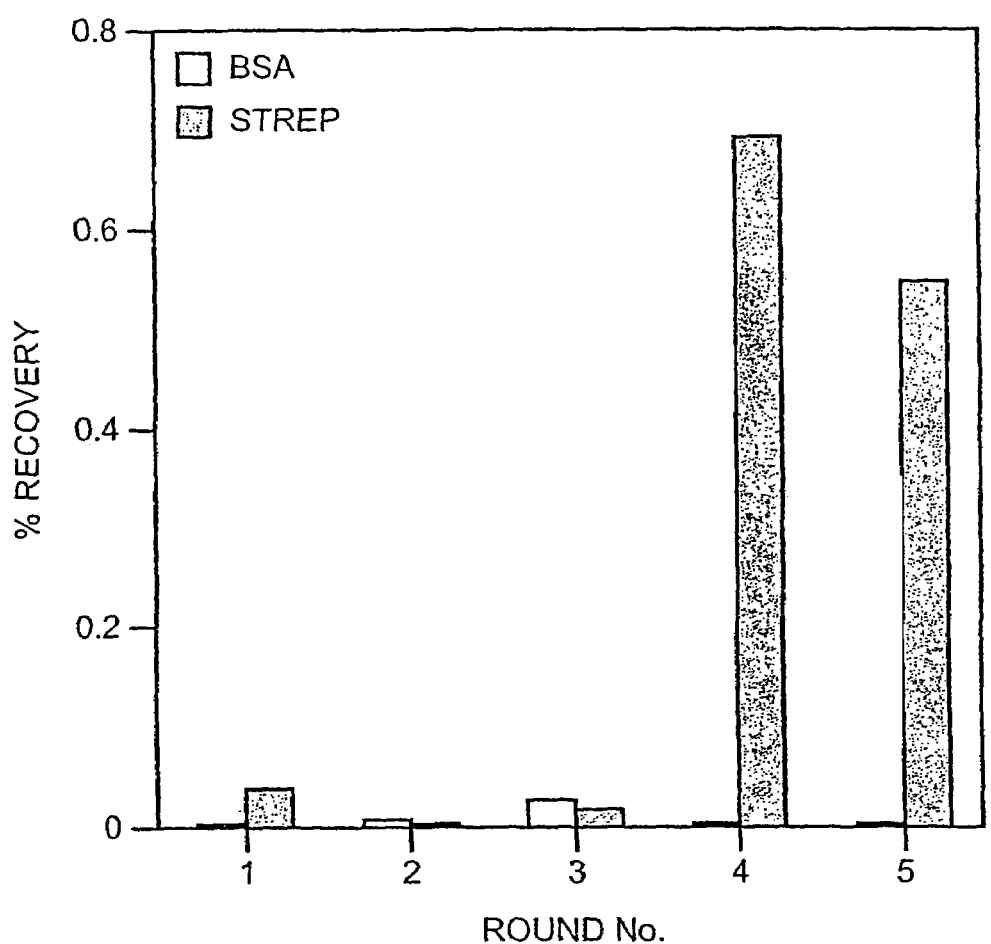

FIG. 8. Bar graph showing enrichment of Ramos cells for production of an immunoglobulin with a novel binding specificity, by iterative selection over five rounds.

Figure 9:
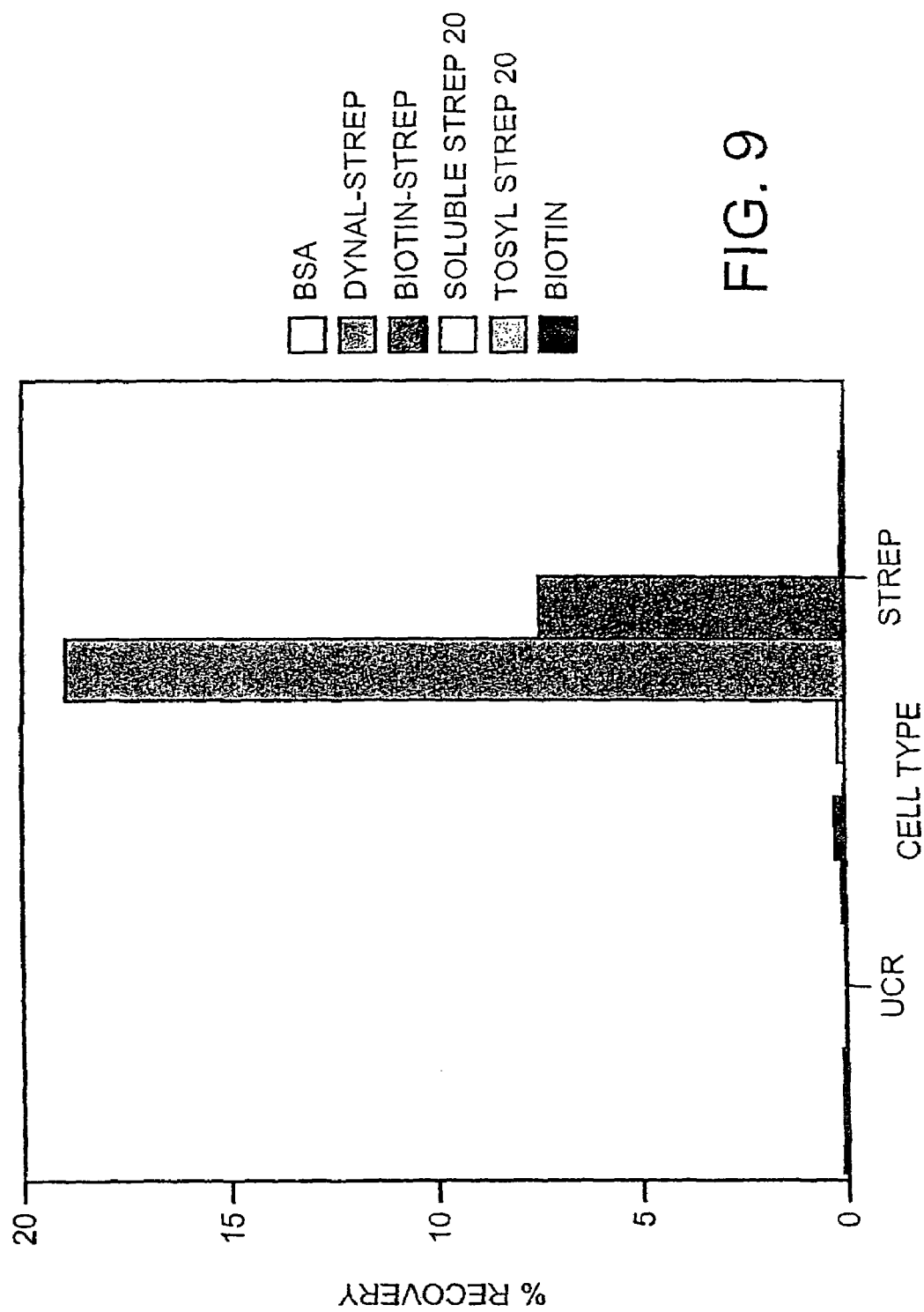

FIG. 9. Bar graph showing improved recovery of Ramos cells binding a novel specificity (streptavidin) by increasing the bead:cell ratio.

Figure 10:
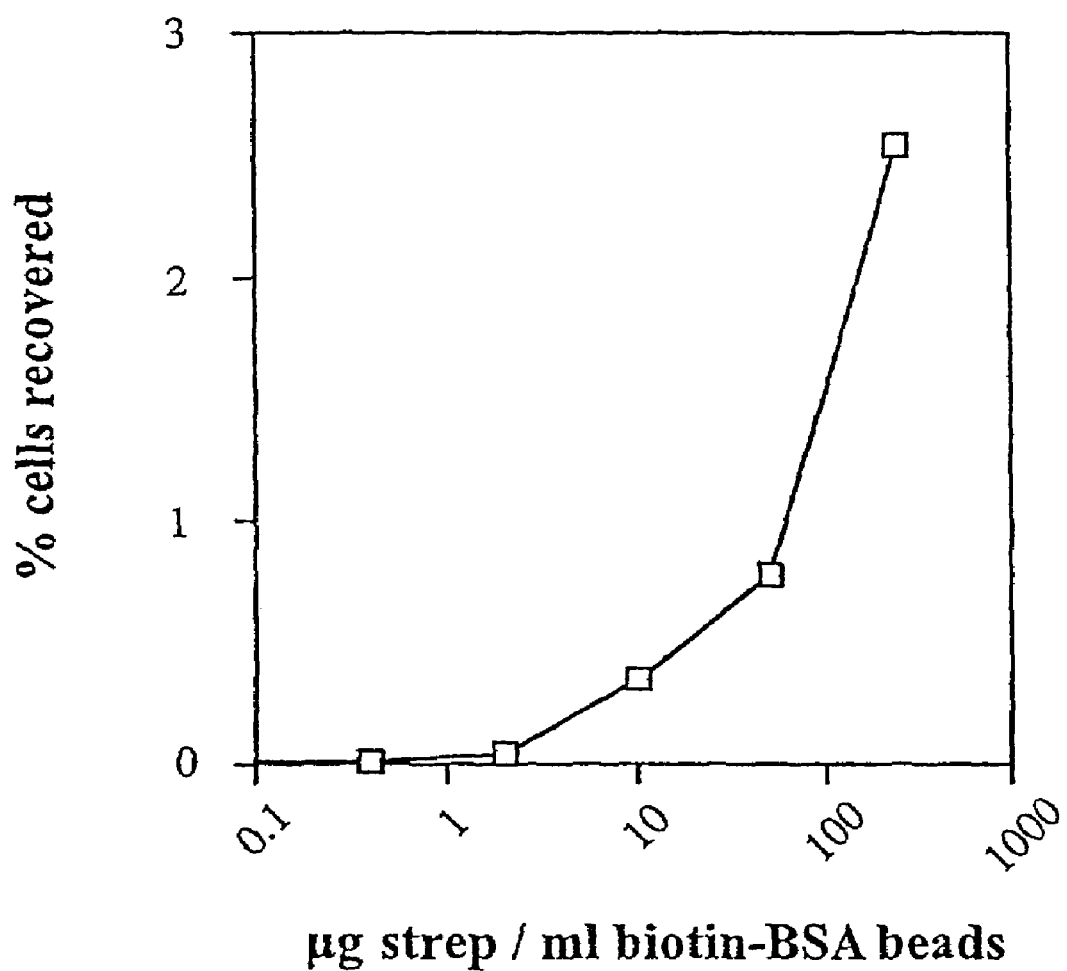

FIG. 10. Chart showing increase in recovery of novel binding specificity Ramos cells according to increasing target antigen concentration.

FIG. 11. $V_H$ sequence (SEQ ID NO: 15; SEQ ID NO: 128) derived from streptavidin-binding Ramos cells. FIG. 11 CONT'D shows the VL sequence of SEQ ID NO: 85' SEQ ID NO: 129. Nucleotide changes observed in comparison with the $V_H$ sequence of the starting population, and predicted amino acid changes, are shown in bold.

FIG. 12. Amount of IgM in supernatants of cells selected in rounds 4, 6 and 7 of a selection process for streptavidin binding, against control medium and unselected Ramos cell supernatant.

Figure 13:
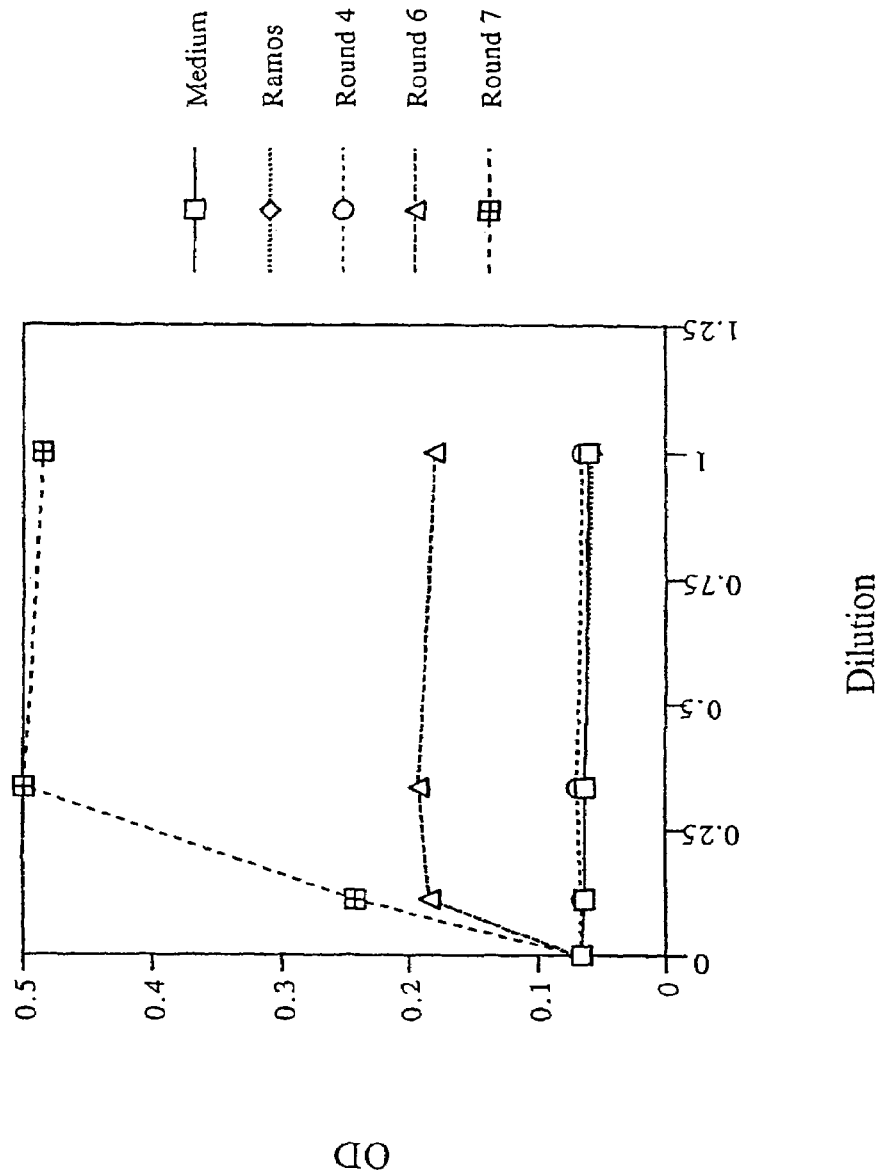

FIG. 13. Streptavidin binding of IgM from the supernatants of FIG. 12.

Figure 14:
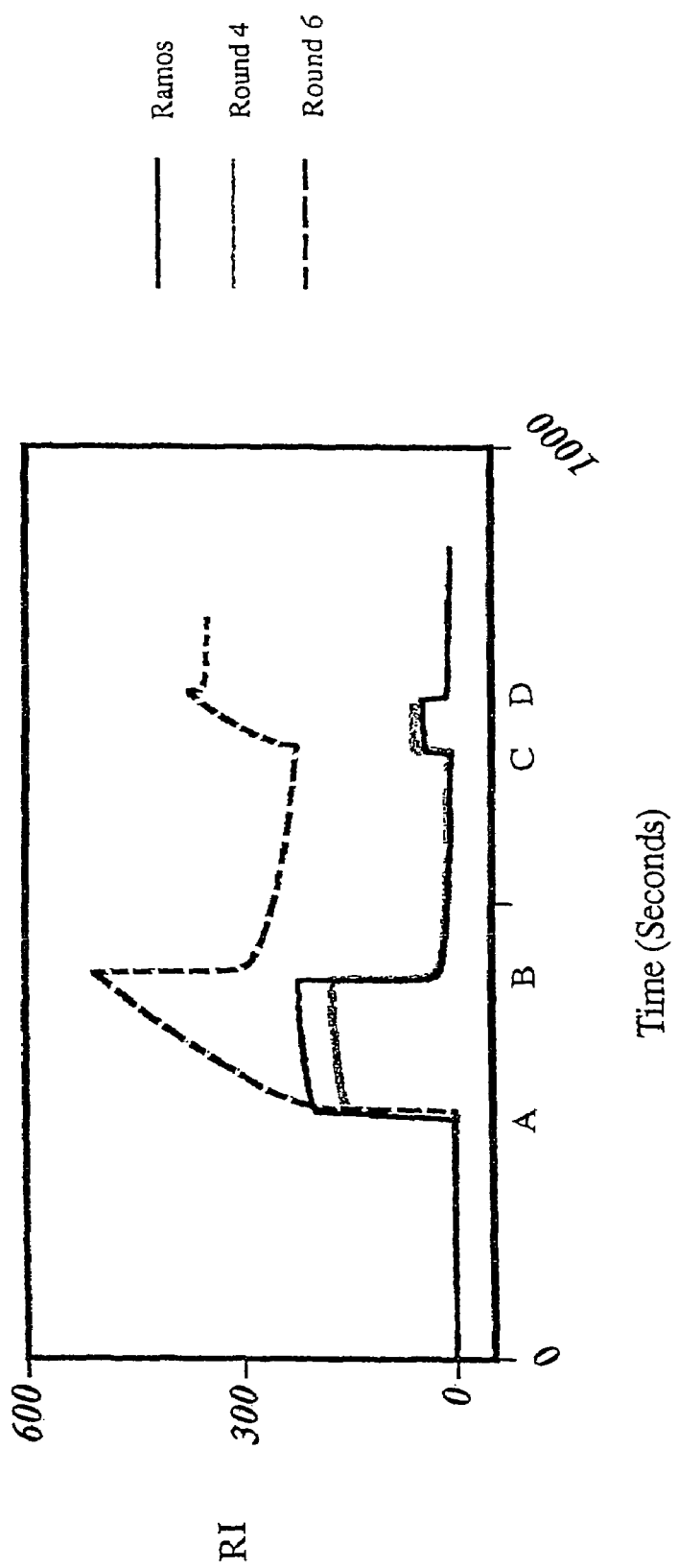

FIG. 14. Streptavidin binding of supernatants from round 4 and round 6 of a selection for streptavidin binding, analysed by surface plasmon resonance.

Figure 15:
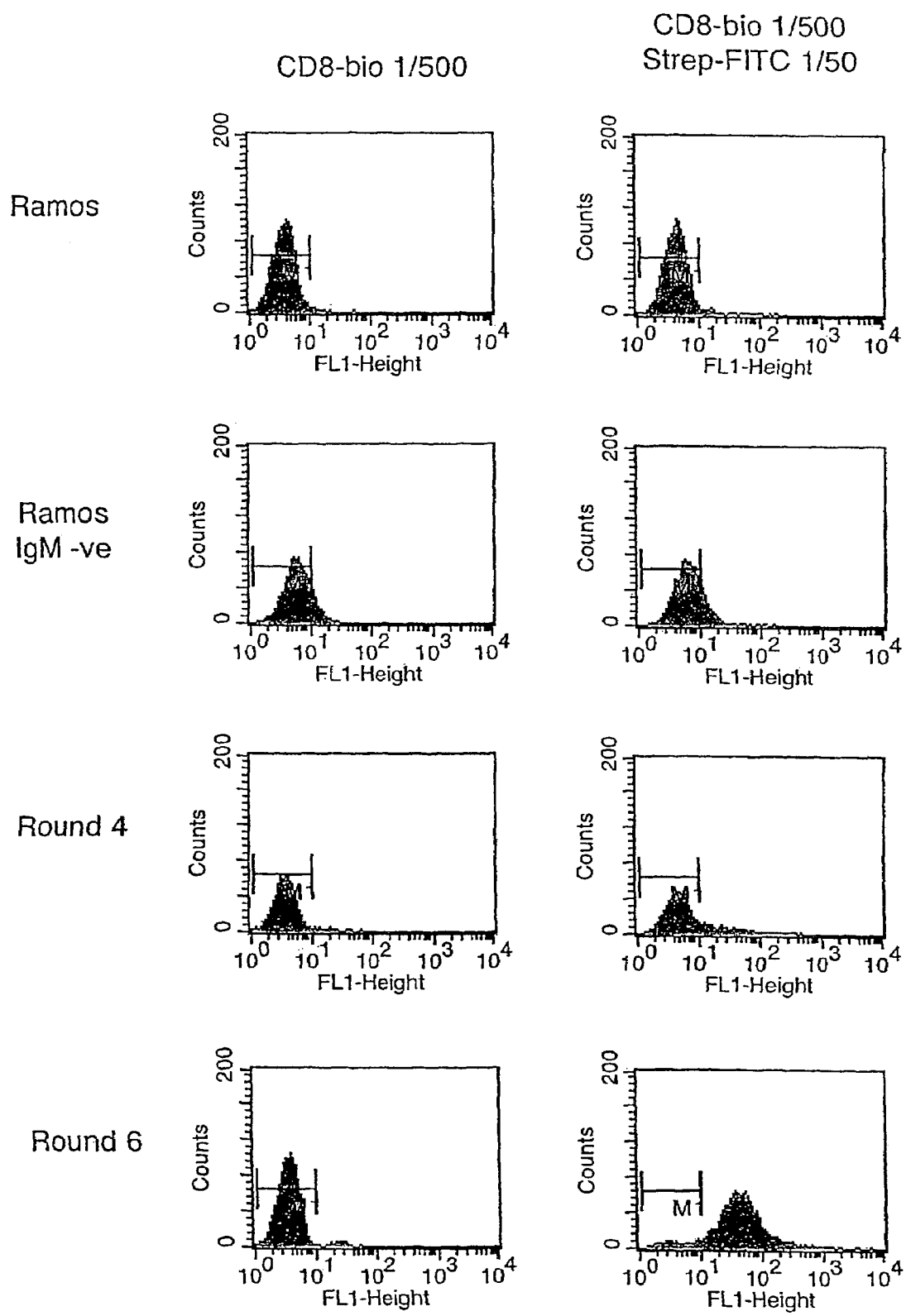

FIG. 15. FACS analysis of binding to streptavidin-FITC of cells selected in rounds 4 and 6.

FIG. 16. $V_H$ (SEQ ID NO: 15; SEQ ID NO: 128) and $V_L$ (SEQ ID NO: 85; SEQ ID NO: 129) sequences of round 6 selected IgM.

Figure 17:
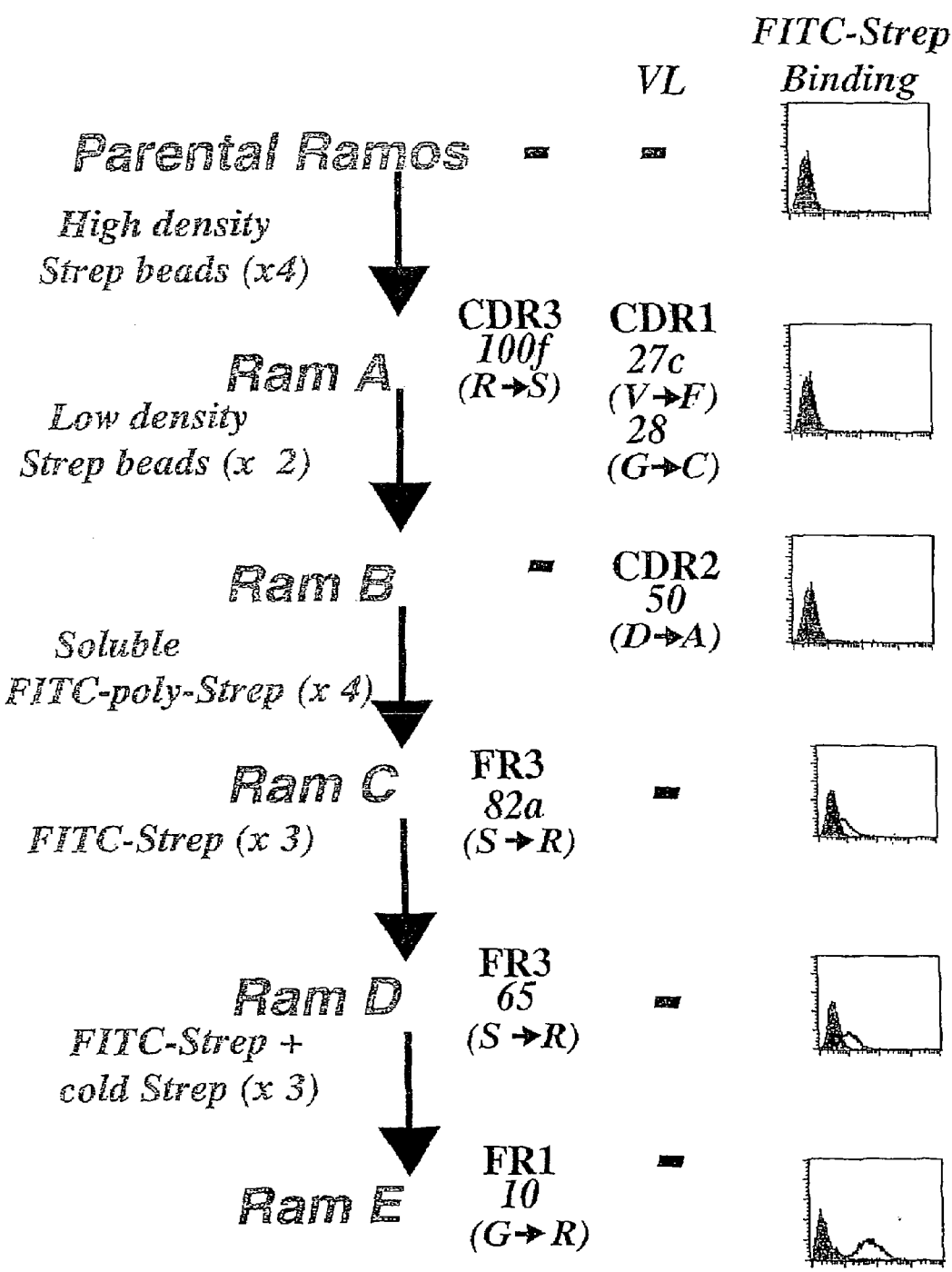

FIG. 17. FACS analysis of affinity matured Ramos cells selected against streptavidin.

Figure 18:
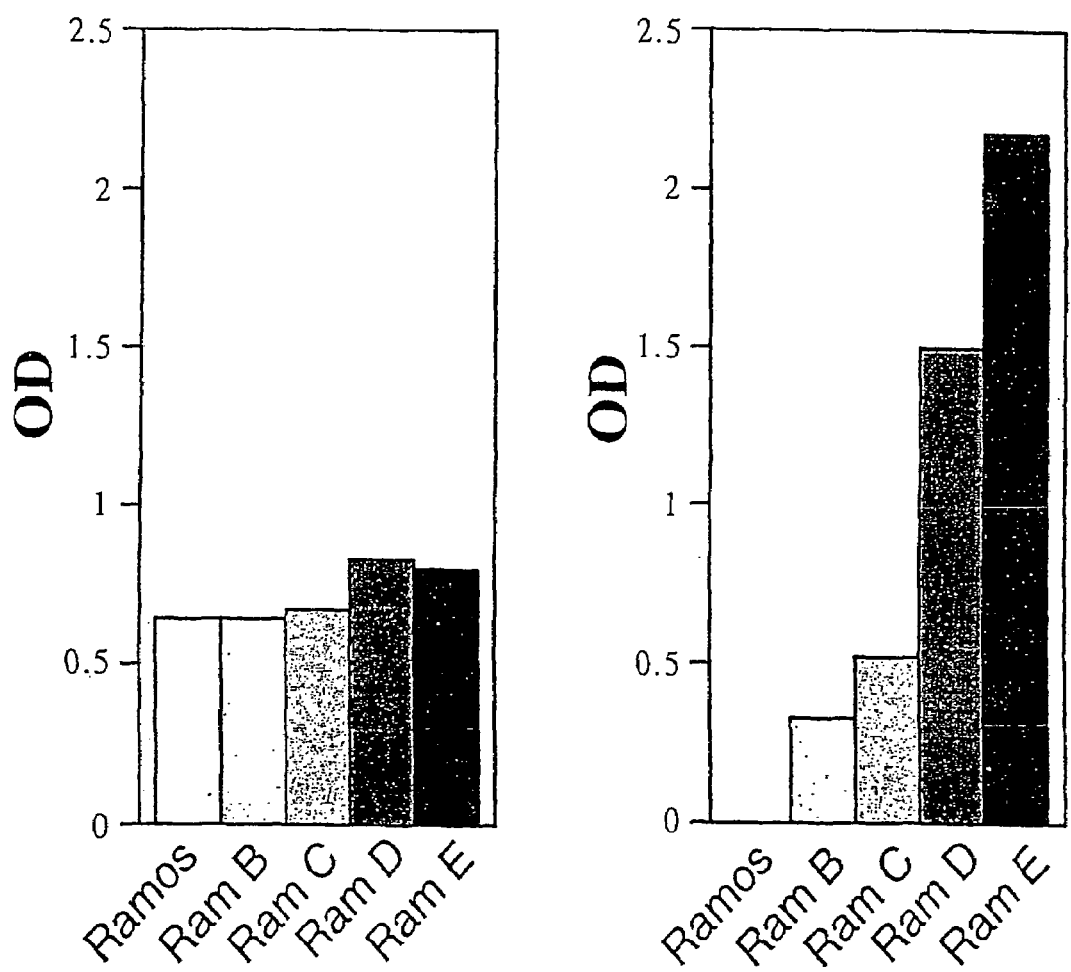

FIG. 18. ELISA of affinity matured Ramos cells.

Figure 19:
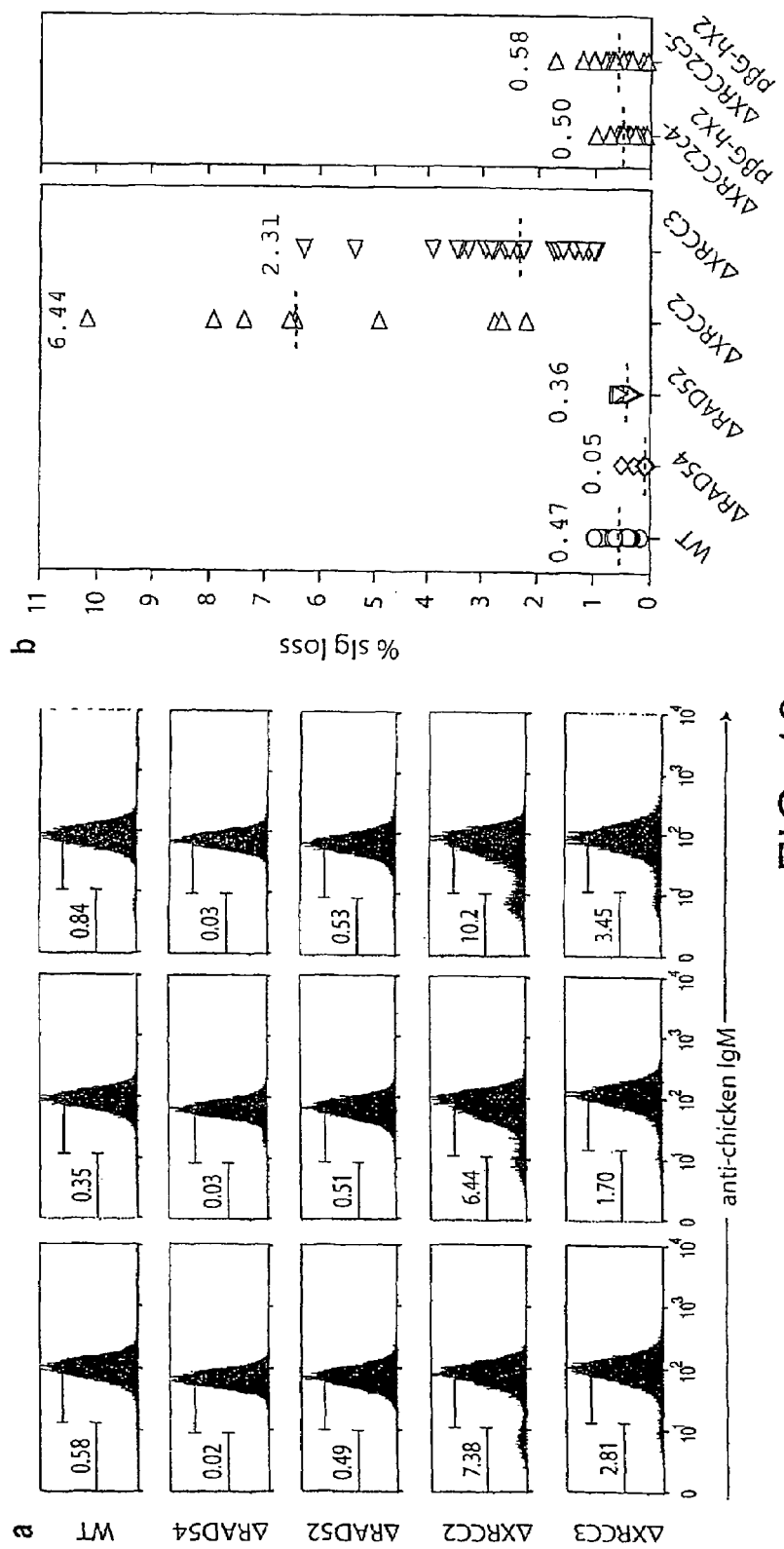

FIG. 19. sIgM-loss variants in wild-type and repair deficient DT40.

(A) flow cytometric analysis of sIgM heterogeneity in wild type and repair deficient cells.

(B) fluctuation analysis of the frequency of generation of sIgM-loss variants.

Figure 20:
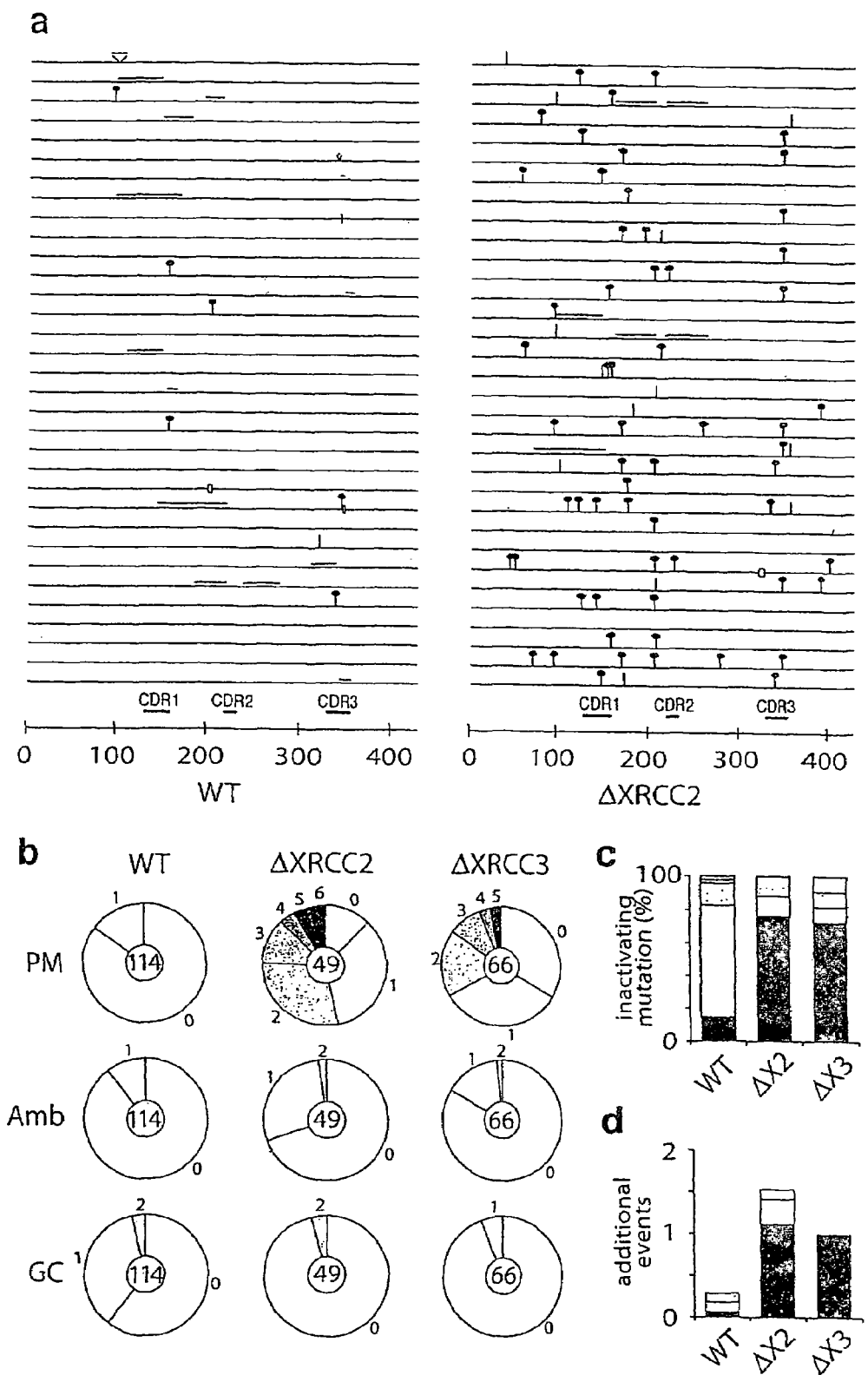

FIG. 20. Analysis of $V_\lambda$ sequences cloned from sIgM variants of DT40.

Figure 21:
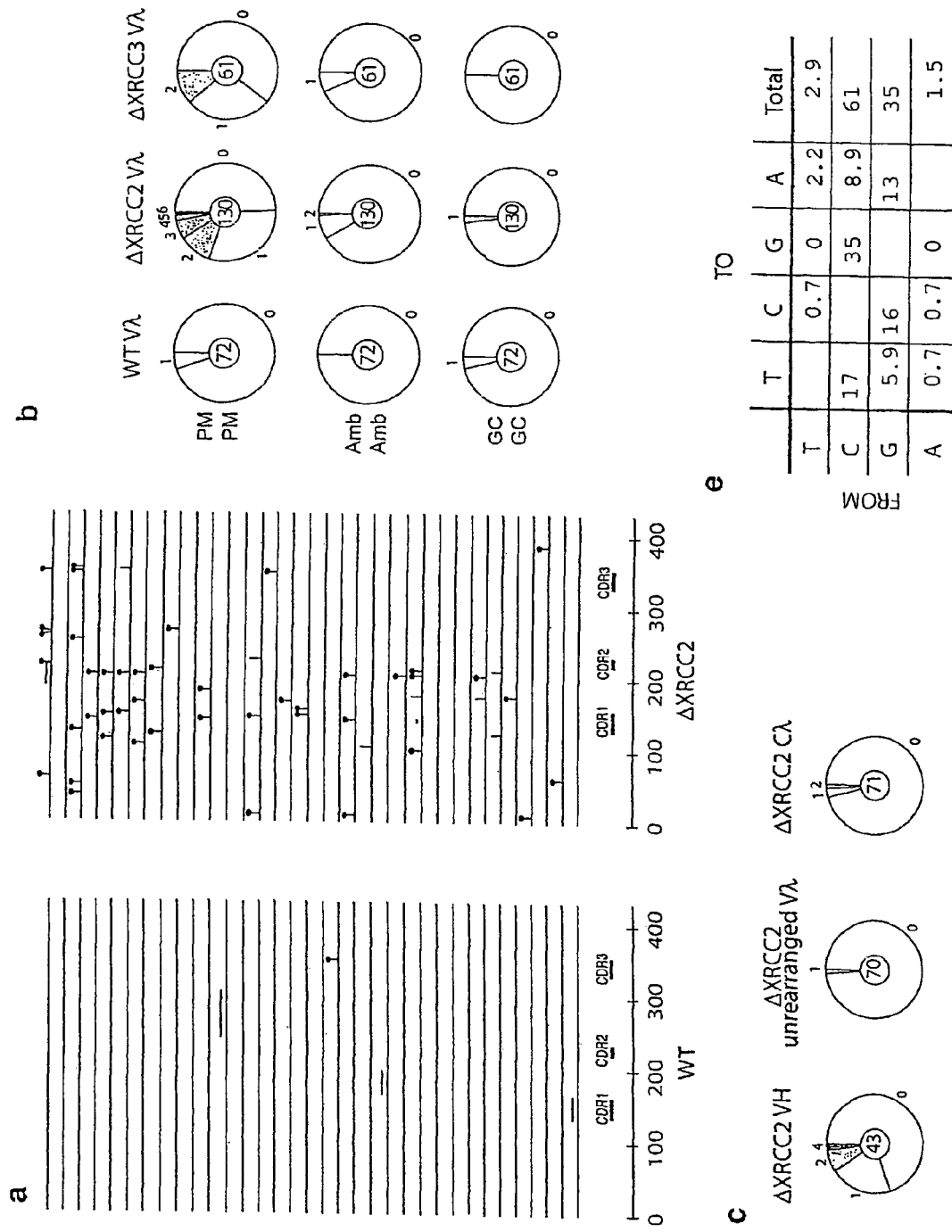

FIG. 21. Analysis of Ig sequences of unsorted DT40 populations after one month of clonal expansion. The sequence of FIG. 21d is SEQ ID NO: 86.

Figure 22:
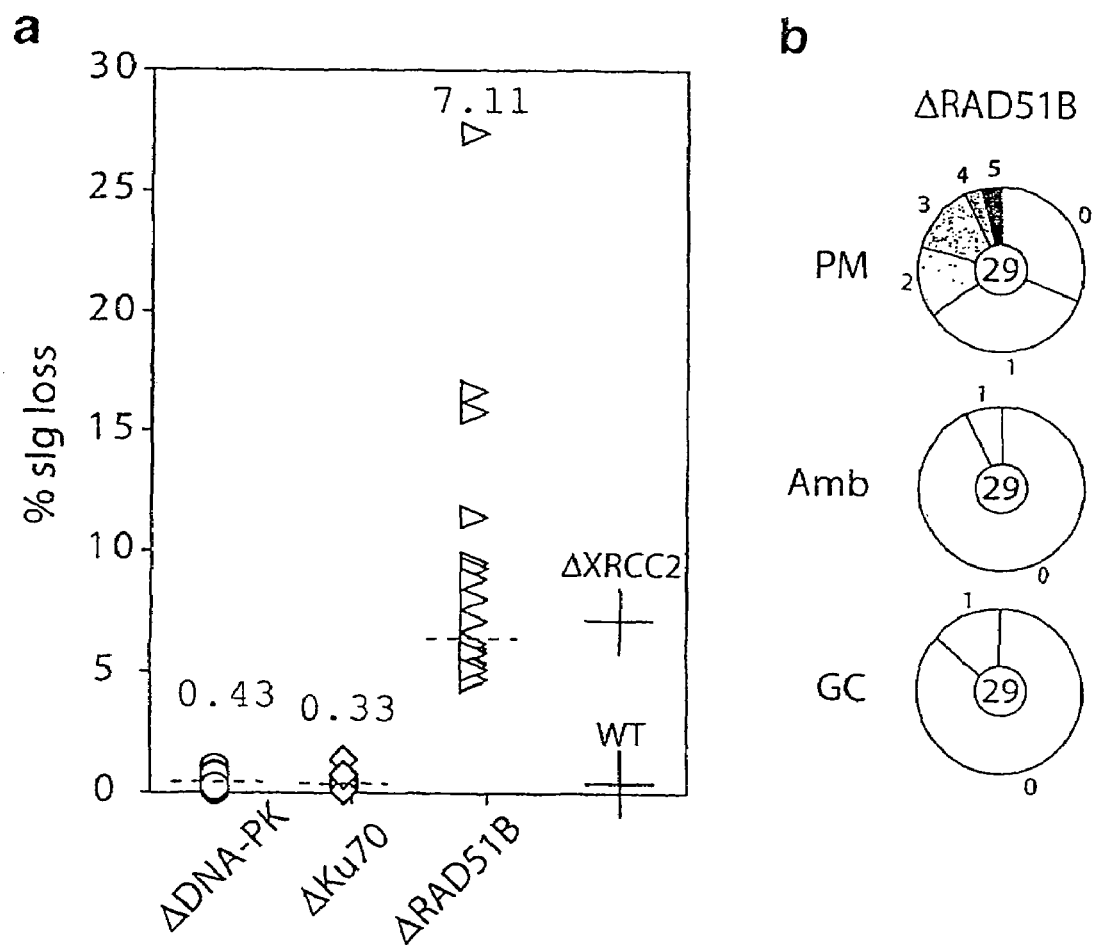

FIG. 22. Analysis of sIgM loss variants of DT40 cells deficient in DNA-PK, Ku70 and Rad51B.

Figure 23:
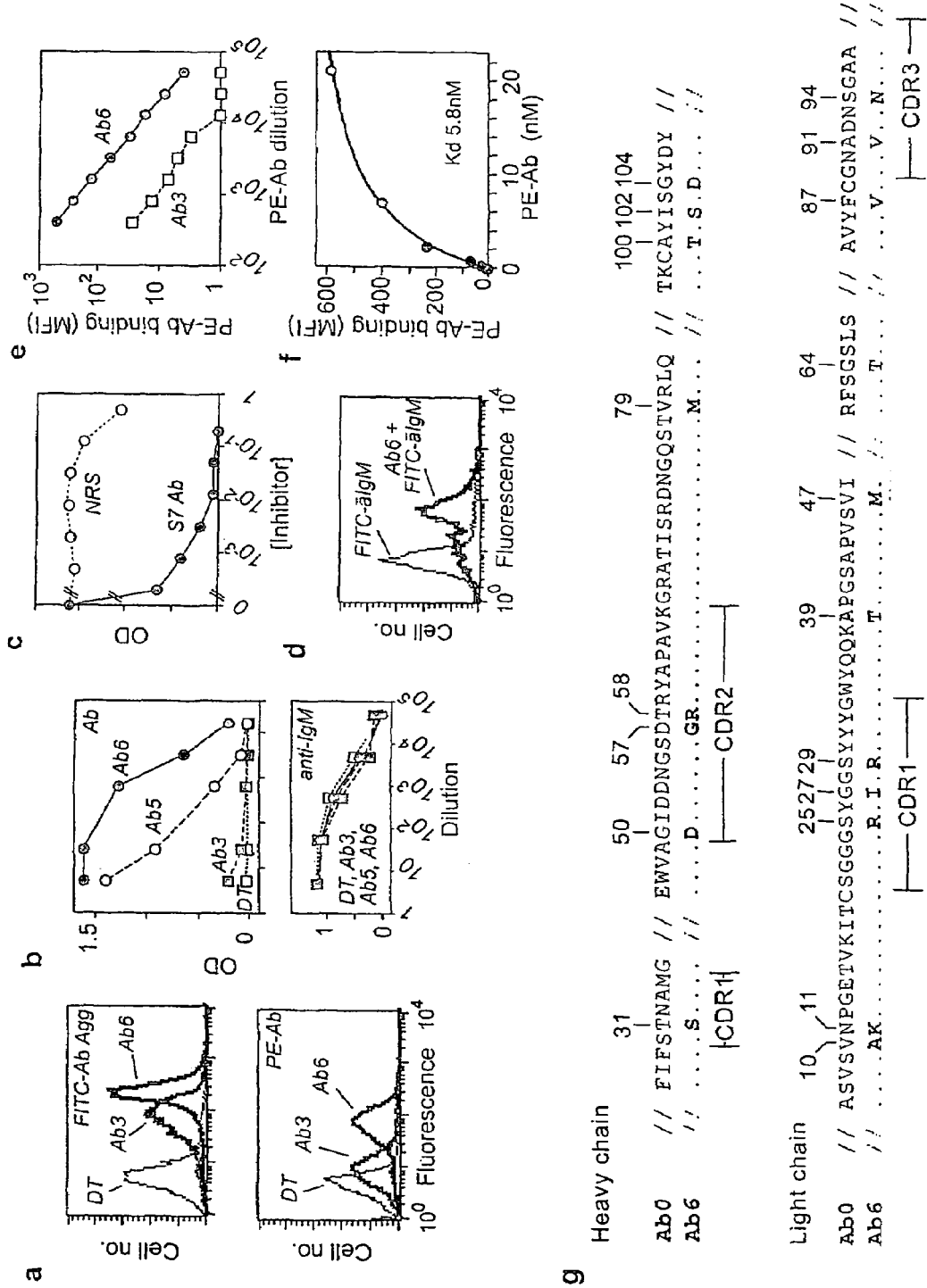

FIG. 23. A dynasty of IgMs from DT40 specific for a rat immunoglobulin idiotype. Cells were subjected to six rounds of selection using an aggregate of biotinylated-rat S7 IgG2a, monoclonal antibody (Ab)/FITC-streptavidin to yield DT-Ab3, which was then subjected to a further three rounds of sorting with a direct PE-Ab conjugate to yield DTAb6. (a) Analysis of the binding of biotinylated Ab/FITC-Strep aggregate as well as ofPE-Ab to DT-Ab3 and DT-Ab6 cells. (b) Binding of IgM in the supematant of DTAb3, 5 and 6 cells to the S7 Ab monitored by ELISA using plates coated with S7 Ab and detection with anti-chicken IgM. Supematants were controlled for total IgM titres. No binding by the DT-Ab6 IgM was detected to a wide variety of rat hybridoma and chimaericmAbs of different isotypes (generously provided by G. Butcher and M Bruggemann (not shown)).(c) Binding of DT-Ab6 IgM to S7 rat IgG Ab coated on to the plate is competed by S7 Ab itself but scarcely by normal rat serum. The S7 (stock at 0.5 mg/ml) and rat serum competitors were used at the dilutions indicated. (d) DT-Ab6 IgM can be used to stain S7 hybridoma cells. Staining was detected by flow cytometry of fixed, permeabilised cells, detecting using FITC-conjugated anti-chicken IgM. (e) Comparison of the staining of DT-Ab3 and DT-Ab6 cells byPE-Ab conjugate using various dilutions of the original 0.2 mg/ml stock (PE-S7 Ab; Pharamacia). (f) Affinity determination. DT-Ab6 cells (106) were incubated with 0.2 picomoles of PE-conjugated S7 Ab in various volumes to give the PE-Ab concentrations indicated; the mean fluorescence intensity (MFI) of the cells determined following washing. (g) Comparison of the $IgV_H/V_L$ sequences of DT-Ab6 and the parental population. Selection performed using an aggregate of biotinyleted ratIgGmAbS7 with FITC streprovidin (See Example 9 for details).

Sequence analysis of DT-Ab6 $V_H/V_L$ showing 19 amino acid substitutions as compared to the perental DT40 Sequence (Seq ID Nos: 88-99). The sequences are:

```
                                        (SEQ ID NO:88)
    FIFSTNAMG (SEQ ID NO:89)
    EWVAGIDDNGSDTRYAPAVKGRATISRDNGQSTVRLQ (SEQ ID NO:90)
    TKCAYISGYDY (SEQ ID NO:91)
    FIFSSNAMG (SEQ ID NO:92)
    EWVADIDDNGSGRRYAPAVKGRATISRDNGQSTMRLQ (SEQ ID NO:93)
    TKCTYSSDYDY (SEQ ID NO:94)
    ASVSVNPGETVKITCSGGGSYGGSYYYGWYQQKAPGSAPVSVI (SEQ ID NO:95)
    RFSGSLS (SEQ ID NO:96)
    AVYFCGNADNSGAA (SEQ ID NO:97)
    ASVSAKPGETVKITCSGGGRYIGRYYYGWYQQKTPGSAPVSMI (SEQ ID NO:98)
    RFSTSLS (SEQ ID NO:99)
    AVYVCGNVDNNGAA.
```

Figure 24:
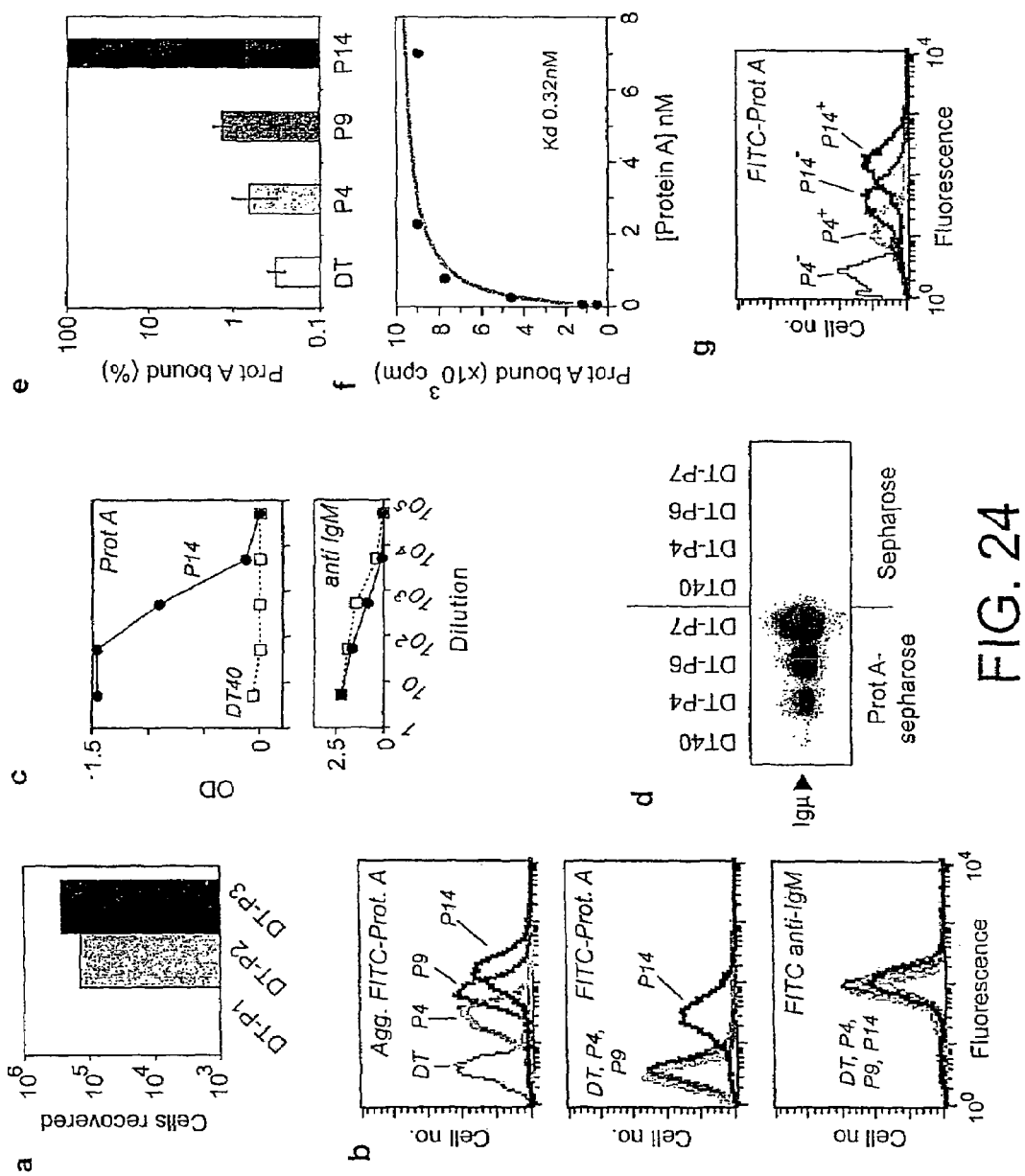

FIG. 24. A dynasty of Protein A-specific IgMs from DT40. (a) Selection of DT40variants binding to derivatised magnetic beads showing the number of cells recovered following incubation of 1 Os cells with 106 beads. DT-P1 and P2 were selected on streptavidin-beads coated with biotinylated-Protein A whereas DT-P3 was selected from DT-P2 on tosylated-magnetic beads directly coated with Protein A. (b) Comparison of staining of subclones of various DT-P cells by an aggregate of biotinylated Protein A with FITC-streptavidin, by Protein A that had been directly conjugated with FITC and by FITC-anti-IgM. (c) Binding of IgM in the supernatant of parental DT40 and DT-P14 bulk population to Protein A-coated plates monitored by ELISA using a mouse IgM mAb specific for chicken IgM (Southern Biotechnology) for detection. Total IgM titres were also compared as a control. (d) IgM from the supernatant of DT-P4,-P6 and P7 clones (but not from parental DT40) can be purified on Protein A, using Western blot to detect chicken IgM retained on the Protein A-Sepharose. (e)Binding of [3sS] Protein A to DTP cells. Parental DT40 (DT) or DT-P cells($5\times10^5$ cells in 0.1 ml)) were incubated on ice for 1 h with[$_{35}$S] Protein A (48,000 bindable cpm; 200-2000 Ci/mmol); bound cpm were determined following a single PBS wash. (f) Affinity determination. DT-P14 cells (106) were incubated with 0.7 picomoles [$_{35}$S] Protein A($7\times10^{10}$ bindable cpm/mole) in various volumes to yield the Protein A concentrations indicated; bound cpm were determined following washing. (g) Staining of DT-P4 and DT-P14 cells with FITCProtein A is enhanced by performing the staining in the presence (P4+, P14+) of 1 mg/ml unlabelled rabbit IgG. (h) IgV gene sequences from DT-P subclones. Selection performed with strephavidim beeds coated with biotinyleted ProtA. (DT-P2 FIG. 24; See Example 9 for details).

Sequence analysis of DT-P14 showing 17 amino acid substitutions as composed to the parental DT40Sequence (FIG. 24h). The seciuences (SEQ ID Nos: 100-127) are:

```
                                        (SEQ ID NO:100)
    PGGALSLV (SEQ ID NO:101)
    STNAMGWVRQAPDK (SEQ ID NO:102)
    DNGSDTRYAPAVKGRATISRDNGQSTVRLQ (SEQ ID NO:103)
    AYISGYDY (SEQ ID NO:104)
    PGGPLRLV (SEQ ID NO:105)
    STNAMGWVRQAPDK (SEQ ID NO:106)
    DDGSDTRYAPAVKGRATISRDNGQRTVRLQ (SEQ ID NO:107)
    AYISGCDY (SEQ ID NO:108)
    PGGPLRLV (SEQ ID NO:109)
    STNAMGWVRQAPDK (SEQ ID NO:110)
    DDGSDTRYAPAVKGRATISRDNGQRTVRLQ (SEQ ID NO:111)
    AYISGCDY (SEQ ID NO:112)
    PGGPLRLV (SEQ ID NO:113)
    SSNAMGWVRQAPGK (SEQ ID NO:114)
    DDGSDTRYAPAVKGRATISRDNGQRTVRLQ (SEQ ID NO:115)
    AYISGCDY (SEQ ID NO:116)
    PGGPLRLV (SEQ ID NO:117)
    SSNAMGWVRQAPGK (SEQ ID NO:118)
    DDGSDTRYAPAVKGRATISRDNGQRTVRLQ (SEQ ID NO:119)
    AYISGCDY (SEQ ID NO:120)
    ASVSVNPGETVKITCSGGGSYGGSYYYGWYQQKAPGSAPVSVI (SEQ ID NO:121)
    DDEAVYFCGNADNSGAAFGA (SEQ ID NO:122)
    ASVSVNPGETVKITCSGGGSYGGSYYYGWYQQKAPGSAPVSVI (SEQ ID NO:123)
    DDEAVYFCGNADNSGAAFGA (SEQ ID NO:124)
    ASVSANPGETVKITCSGGGRYGASYYYVWYQQKAPGSAPVSVI
```

-continued

DDEAVYFCGNADNSGAAFGA (SEQ ID NO:125)

ASVSANPGETVKITCSGGGRYGASYYYVWYQQKAPGSAPVTVI (SEQ ID NO:126)

DDEAVYFCGNADNSGAAFGA. (SEQ ID NO:127)

Figure 25:
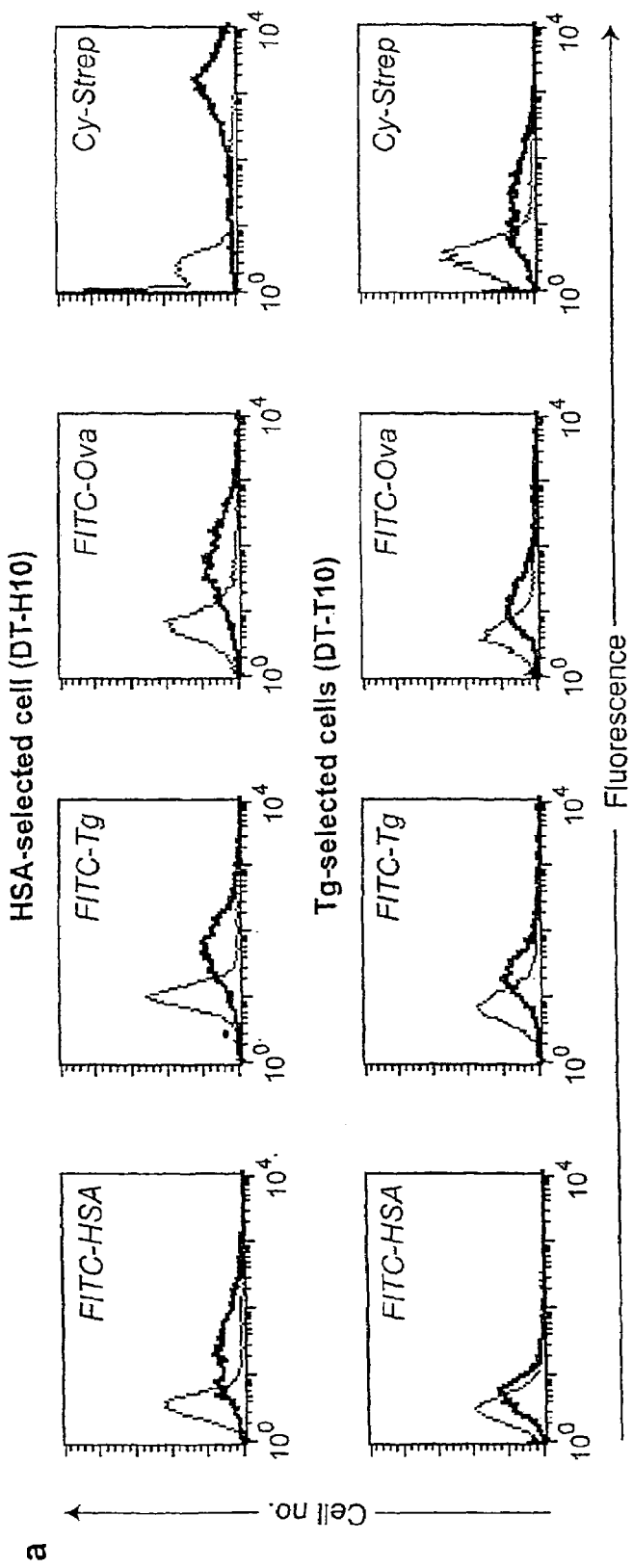
Figure 25:
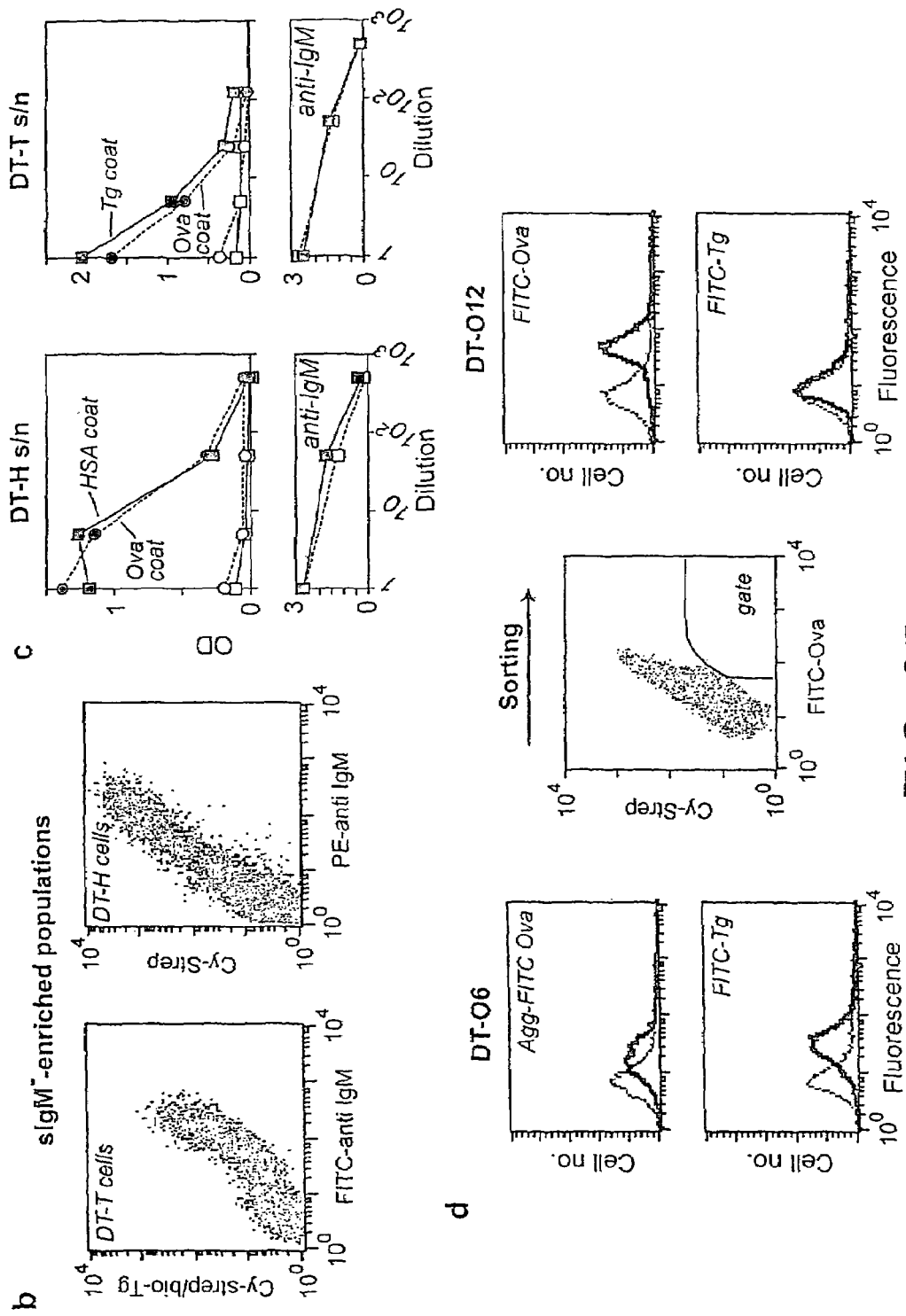

FIG. 25. Antigen-selection of DT40 can yield polyreactive IgMs with the possibility of maturation into specificity. DT-H10 cells were obtained by ten sequential rounds of selection from the parental Xrcc2-deficient DT40 pool using carboxylated magnetic beads to which human serum albumin (HSA) had been coupled. DT-T10 and DT-06 cells were obtained by serial rounds of flow cytometric selection of cells stained with aggregates of FITC-streptavidin with either biotinylated thyrogobulin (DT-T cells) or ovalbumin (DT-O cells), taking the brightest 2% of the population in each round. (a) Flow cytometric analysis of DT-H6 and DT-T6 cells stained with the reagents indicated (Cy-strep, cychrome-streptavidin). (b) Antigen binding by DT-H6 and DT-T6 cells is mediated by the surface IgM as witnessed by 2D flow cytometric analysis of DT-H6 and DT-T6 subpopulations that have been enriched for sIgM-loss variants. (c) ELISA of DTH6 and DT-T6 culture supernatants, monitoring chicken IgM specific for the antigens indicated. (d) DT-06 cells (selected with ovalbumin aggregates) also bind Tg (as well as several other antigens tested (not shown)) but sequential sorting for FITC-Ova$_{bright}$/Cystreptavidin$_{dull}$ cells yields a population exhibiting greater specificity for Ova.

Figure 26:
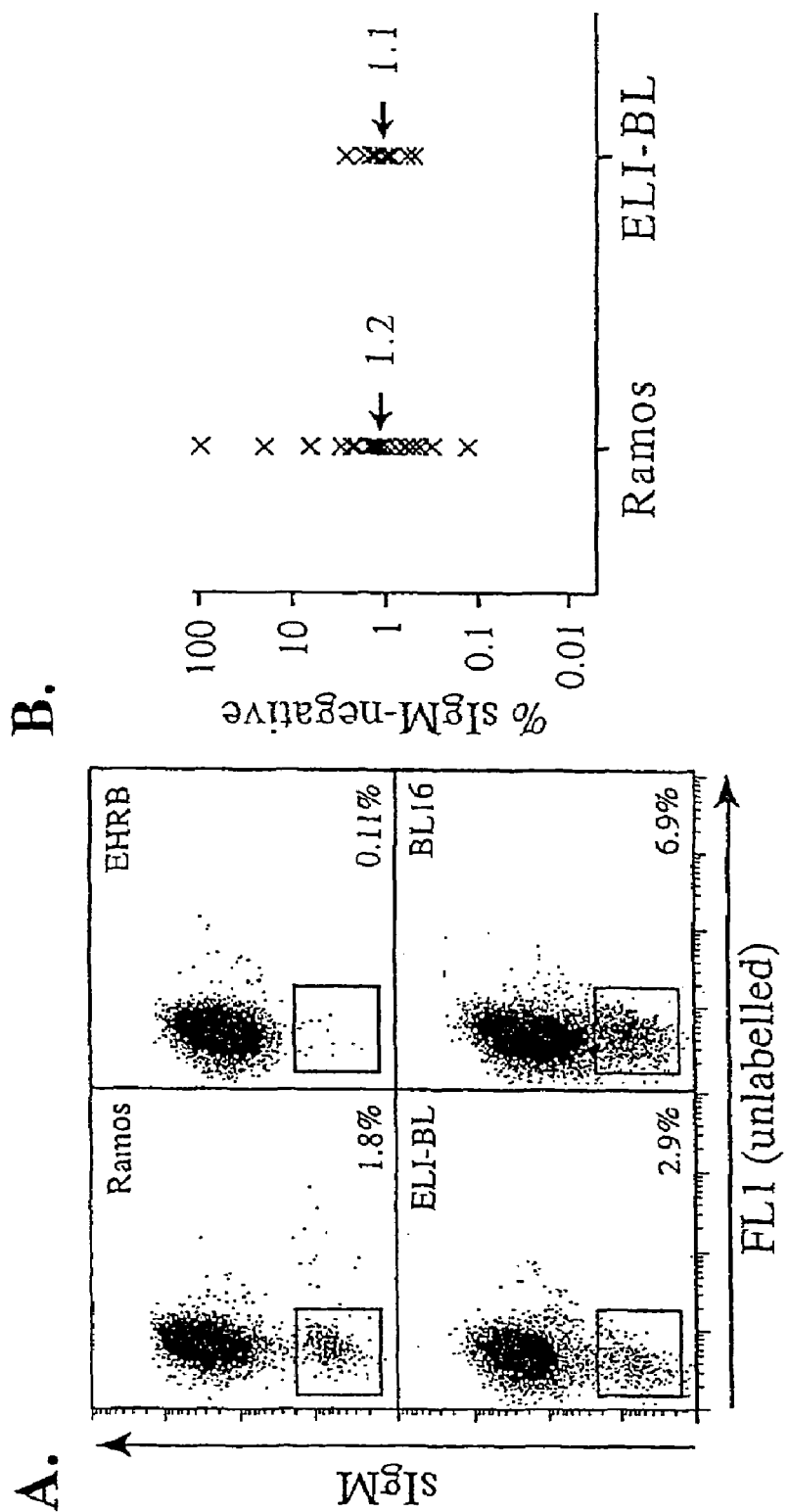

FIG. 26. Analysis of naturally-occurring constitutively hypermutating BL cell lines. The sequence of FIG. 26. C is SEQ ID NO: 87; SEQ ID NO: 130.

DETAILED DESCRIPTION OF THE INVENTION

The present invention makes available for the first time a cell line which constitutively hypermutates selected nucleic acid regions. This permits the design of systems which produce mutated gene products by a technique which mirrors affinity maturation in natural antibody production. The Ramos Burkitt line constitutively diversifies its rearranged immunoglobulin V gene during in vitro culture. This hypermutation does not require stimulation by activated T cells, exogenously-added cytokines or even maintenance of the B cell antigen receptor.

The rate of mutation (which lies in the range $0.2\text{-}1 \times 10^{-4}$ $bp^{-1}$ generation$^{-1}$) is sufficiently high to readily allow the accumulation of a large database of unselected mutations and so reveal that hypermutation in Ramos exhibits most of the features classically associated with immunoglobulin V gene hypermutation in vivo (preferential targeting of mutation to the V; stepwise accumulation of single nucleotide substitutions; transition bias; characteristic mutational hotspots). The large majority of mutations in the unselected database are single nucleotide substitutions although deletions and duplications (sometimes with a flanking nucleotide substitution) are detectable. Such deletions and duplications have also been proposed to be generated as a consequence of hypermutation in vivo (Wilson et al., 1998; Goosens et al., 1998; Wu & Kaartinen, 1995).

The isolation of cells which constitutively hypermutate selected nucleic acid regions is based on the monitoring of V gene mutation in cell lines derived from antibody-producing cells such as B cells. The selection method employed in the invention may be configured in a number of ways.

Selection of Hypermutating Cells

Hypermutating cells may be selected from a population of cells by a variety of techniques, including sequencing of target sequences, selection for expression loss mutants, assay using bacterial MutS protein and selection for change in gene product activity.

One of the features of hypermutation of target nucleic acids is that the process results in the introduction of stop codons into the target sequence with far greater frequency than would be observed in the absence of hypermutation. This results in loss of production of a gene product from the cell. This loss may be exploited to identify cells which are hypermutating nucleic acid sequences.

In a preferred embodiment of the invention, the target nucleic acid encodes an immunoglobulin. Immunoglobulin loss may be detected both for cells which secrete immunoglobulins into the culture medium, and for cells in which the immunoglobulin is displayed on the cell surface. Where the immunoglobulin is present on the cell surface, its absence may be identified for individual cells, for example by FACS analysis, immunofluorescence microscopy or ligand immobilisation to a support. In a preferred embodiment, cells may be mixed with antigen-coated magnetic beads which, when sedimented, will remove from the cell suspension all cells having an immunoglobulin of the desired specificity displayed on the surface.

The technique may be extended to any immunoglobulin molecule, including antibodies, T-cell receptors and the like. The selection of immunoglobulin molecules will depend-on the nature of the clonal population of cells which it is desired to assay according to the invention.

Alternatively, cells according to the invention may be selected by sequencing of target nucleic acids, such as V genes, and detection of mutations by sequence comparison. This process may be automated in order to increase throughput.

In a further embodiment, cells which hypermutate V genes may be detected by assessing change in antigen binding activity in the immunoglobulins produced in a clonal cell population. For example, the quantity of antigen bound by a specific unit amount of cell medium or extract may be assessed in order to determine the proportion of immunoglobulin produced by the cell which retains a specified binding activity. As the V genes are mutated, so binding activity will be varied and the proportion of produced immunoglobulin which binds a specified antigen will be reduced.

Alternatively, cells may be assessed in a similar manner for the ability to develop a novel binding affinity, such as by exposing them to an antigen or mixture of antigens which are initially not bound and observing whether a binding affinity develops as the result of hypermutation.

In a further embodiment, the bacterial MutS assay may be used to detect sequence variation in target nucleic acids. The MutS protein binds to mismatches in nucleic acid hybrids. By creating heteroduplexes between parental nucleic acids and those of potentially mutated progeny, the extent of mismatch formation, and thus the extent of nucleic acid mutation, can be assessed.

Where the target nucleic acid encodes an gene product other than an immunoglobulin, selection may be performed by screening for loss or alteration of a function other than binding. For example, the loss or alteration of an enzymatic activity may be screened for.

Cells which target sequence hypermutation are assessed for mutation in other nucleic acid regions. A convenient region to assay is the constant (C) region of an immunoglobulin gene. C regions are not subject to directed hypermutation according to the invention. The assessment of C regions is preferably made by sequencing and comparison, since this is the most certain method for determining the absence of mutations. However, other techniques may be employed, such as monitoring for the retention of C region activities, for example complement fixation, which may be disrupted by hypermutation events.

Genetic Manipulation of Cells

Hypermutating cells according to the invention may be selected from cells which have been genetically manipulated to enhance rates of hypermutation in the Ig V-region. Genes which are responsible for modulation of mutation rates include, in general, in nucleic acid repair procedures in the cell. Genes which are manipulated in accordance with the present invention may be upregulated, downregulated or deleted.

Up- or down-regulation refers to an increase, or decrease, in activity of the gene product encoded by the gene in question by at least 10%, preferably 25%, more preferably 40, 50, 60, 70, 80, 90, 95, 99% or more. Upregulation may of course represent an increase in activity of over 100%, such as 200% or 500%. A gene which is 100% downregulated is functionally deleted and is referred to herein as "deleted".

Preferred genes manipulated in accordance with the present invention include analogues and/or paralogues of the Rad51 gene, in particular xrcc2, xrcc3 and Rad51 genes.

Rad51 analogues and/or paralogues are advantageously downregulated, and preferably deleted. Downregulation or deletion of one or more Rad51 paralogues, gives rise to an increase in hypermutation rates in accordance with the invention. Preferably, two or more Rad51 genes, including analogues and/or paralogues thereof, are downregulated or deleted.

In a highly preferred embodiment, avian cell lines such as the chicken DT40 cell line are modified by deletion of xrcc2 and/or xrcc3. Δ xrcc2 DT40 as well Δxrcc3-DT40 are constitutively hypermutating cell lines isolated in accordance with the present invention.

Adaptation of the Endogenous Gene Products

Having obtained a cell line which constitutively hypermutates an endogenous gene, such as an immunoglobulin V region gene, the present invention provides for the adaptation of the endogenous gene product, by constitutive hypermutation, to produce a gene product having novel properties. For example, the present invention provides for the production of an immunoglobulin having a novel binding specificity or an altered binding affinity.

The process of hypermutation is employed, in nature, to generate improved or novel binding specificities in immunoglobulin molecules. Thus, by selecting cells according to the invention which produce immunoglobulins capable of binding to the desired antigen and then propagating these cells in order to allow the generation of further mutants, cells which express immunoglobulins having improved binding to the desired antigen may be isolated.

A variety of selection procedures may be applied for the isolation of mutants having a desired specificity. These include Fluorescence Activated Cell Sorting (FACS), cell separation using magnetic particles, antigen chromatography methods and other cell separation techniques such as use of polystyrene beads.

Separating cells using magnetic capture may be accomplished by conjugating the antigen of interest to magnetic particles or beads. For example, the antigen may be conjugated to superparamagnetic iron-dextran particles or beads as supplied by Miltenyi Biotec GmbH. These conjugated particles or beads are then mixed with a cell population which may express a diversity of surface immunoglobulins. If a particular cell expresses an immunoglobulin capable of binding the antigen, it will become complexed with the magnetic beads by virtue of this interaction. A magnetic field is then applied to the suspension which immobilises the magnetic particles, and retains any cells which are associated with them via the covalently linked antigen. Unbound cells which do not become linked to the beads are then washed away, leaving a population of cells which is isolated purely on its ability to bind the antigen of interest. Reagents and kits are available from various sources for performing such one-step isolations, and include Dynal Beads (Dynal AS; http://www.dynal.no), MACS-Magnetic Cell Sorting (Miltenyi Biotec GmbH; www.miltenvibiotec.com), CliniMACS (AmCell; www.amcell.com) as well as Biomag, Amerlex-M beads and others.

Fluorescence Activated Cell Sorting (FACS) can be used to isolate cells on the basis of their differing surface molecules, for example surface displayed immunoglobulins. Cells in the sample or population to be sorted are stained with specific fluorescent reagents which bind to the cell surface molecules. These reagents would be the antigen(s) of interest linked (either directly or indirectly) to fluorescent markers such as fluorescein, Texas Red, malachite green, green fluorescent protein (GFP), or any other fluorophore known to those skilled in the art. The cell population is then introduced into the vibrating flow chamber of the FACS machine. The cell stream passing out of the chamber is encased in a sheath of buffer fluid such as PBS (Phosphate Buffered Saline). The stream is illuminated by laser light and each cell is measured for fluorescence, indicating binding of the fluorescent labelled antigen. The vibration in the cell stream causes it to break up into droplets, which carry a small electrical charge. These droplets can be steered by electric deflection plates under computer control to collect different cell populations according to their affinity for the fluorescent labelled antigen. In this manner, cell populations which exhibit different affinities for the antigen(s) of interest can be easily separated from those cells which do not bind the antigen. FACS machines and reagents for use in FACS are widely available from sources world-wide such as Becton-Dickinson, or from service providers such as Arizona Research Laboratories www.arl.Arizona.edu/facs/).

Another method which can be used to separate populations of cells according to the affinity of their cell surface protein(s) for a particular antigen is affinity chromatography. In this method, a suitable resin (for example CL-600 Sepharose, Pharmacia Inc.) is covalently linked to the appropriate antigen. This resin is packed into a column, and the mixed population of cells is passed over the column. After a suitable period of incubation (for example 20 minutes), unbound cells are washed away using (for example) PBS buffer. This leaves only that subset of cells expressing immunoglobulins which bound the antigen(s) of interest, and these cells are then eluted from the column using (for example) an excess of the antigen of interest, or by enzymatically or chemically cleaving the antigen from the resin. This may be done using a specific protease such as factor X, thrombin, or other specific protease known to those skilled in the art to cleave the antigen from the column via an appropriate cleavage site which has previously been incorporated into the antigen-resin complex. Alternatively, a non-specific protease, for example trypsin, may be employed to remove the antigen from the resin, thereby releasing that population of cells which exhibited affinity for the antigen of interest.

Insertion of Heterologous Transcription Units

In order to maximise the chances of quickly selecting an antibody variant capable of binding to any given antigen, or to exploit the hypermutation system for non-immunoglobulin genes, a number of techniques may be employed to engineer cells according to the invention such that their hypermutating abilities may be exploited.

In a first embodiment, transgenes are transfected into a cell according to the invention such that the transgenes become targets for the directed hypermutation events.

As used herein, a "transgene" is a nucleic acid molecule which is inserted into a cell, such as by transfection or transduction. For example, a "transgene" may comprise a heterologous transcription unit as referred to above, which may be inserted into the genome of a cell at a desired location.

The plasmids used for delivering the transgene to the cells: are of conventional construction and comprise a coding sequence, encoding the desired gene product, under the control of a promoter. Gene transcription from vectors in cells according to the invention may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with the heterologous coding sequence, provided such promoters are compatible with the host system of the invention.

Transcription of a heterologous coding sequence by cells according to the invention may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100-270) and the CMV early promoter enhancer. The enhancer may be spliced into the vector at a position 5' or 3' to the coding sequence, but is preferably located at a site 5' from the promoter.

Advantageously, a eukaryotic expression vector may comprise a locus control region (LCR). LCRs are capable of directing high-level integration site independent expression of transgenes integrated into host cell chromatin, which is of importance especially where the heterologous coding sequence is to be expressed in the context of a permanently-transfected eukaryotic cell line in which chromosomal integration of the vector has occurred, in vectors designed for gene therapy applications or in transgenic animals.

Eukaryotic expression vectors will also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA.

An expression vector includes any vector capable of expressing a coding sequence encoding a desired gene product that is operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding a heterologous coding sequence may be inserted into a vector suitable for expression of cDNAs in mammalian cells, e.g. a CMV enhancer-based vector such as pEVRF (Matthias, et al., 1989).

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing gene product expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

In one variation of the first embodiment, transgenes according to the invention also comprise sequences which direct hypermutation. Such sequences have been characterised, and include those sequences set forth in Klix et al., (1998), and Sharpe et al., (1991), incorporated herein by reference. Thus, an entire locus capable of expressing a gene product and directing hypermutation to the transcription unit encoding the gene product is transferred into the cells. The transcription unit and the sequences which direct hypermutation are thus exogenous to the cell. However, although exogenous the sequences which direct hypermutation themselves may be similar or identical to the sequences which direct hypermutation naturally found in the cell In a second embodiment, the endogenous V gene(s) or segments thereof may be replaced with heterologous V gene(s) by homologous recombination, or by gene targeting using, for example, a Lox/Cre system or an analogous technology or by insertion into hypermutating cell lines which have spontaneously deleted endogenous V genes. Alternatively, V region gene(s) may be replaced by exploiting the observation that hypermutation is accompanied by double stranded breaks in the vicinity of rearranged V genes.

The invention is further described below, for the purposes of illustration only, in the following examples.

EXAMPLE 1

Selection of a Hypermutating Cell

In order to screen for a cell that undergoes hypermutation in vitro, the extent of diversity that accumulates in several human Burkitt lymphomas during clonal expansion is assessed. The Burkitt lines BL2, BL41 and BL70 are kindly provided by G. Lenoir (IARC, Lyon, France) and Ramos (Klein et al., 1975, *Intervirology* 5: 319-334) is provided by D. Fearon (Cambridge, UK). Their rearranged $V_H$ genes are PCR amplified from genomic DNA using multiple $V_H$ family primers together with a $J_H$ consensus oligonucleotide. Amplification of rearranged $V_H$ segments is accomplished using Pfu polymerase together with one of 14 primers designed for each of the major human $V_H$ families (Tomlinson, 1997, V Base database of human antibody genes. Medical Research Council, Centre for Protein Engineering, UK.) and a consensus $J_H$ back primer which anneals to all six human $J_H$ segments (JOL48, 5'-GCGGTACCTGAG-GAGACGGTGACC-3' (SEQ ID NO: 1), gift of C. Jolly). Amplification of the Ramos $V_H$ from genomic DNA is performed with oligonucleotides RVHFOR (5'-CCCCAAGCTTCCCAGGTGCAGCTACAGCAG (SEQ ID NO: 2), and JOL48. Amplification of the expressed $V_H$-Cµ cDNA is performed using RVHFOR and Cµ 2BACK (5'-CCCCGGTACCAGATGAGCTTGGACTTGCGG (SEQ ID NO: 3)). The genomic Cµ C1/2 region is amplified using Cµ 2BACK with Cµ 1FOR (5'-CCCCAAGCTTCGG-GAGTGCATCCGCCCCAACCCTT (SEQ ID NO: 4)); the functional Cµ allele of Ramos contains a C at nucleotide 8 of Cµ 2 as opposed to T on the non-functional allele. Rearranged Vλ's are amplified using 5'-CCCCAAGCTTC-CCAGTCTGCCCTGACTCAG (SEQ ID NO: 5) and 5'-CCCCTCTAGACCACCTAGGACGGTC-AGCTT (SEQ ID NO: 6). PCR products are purified using QIAquick (Qiagen) spin columns and sequenced using an ABI1377 sequencer following cloning into M13. Mutations are computed using the GAP4 alignment program (Bonfield et al., 1995, *NAR* 23: 4992-99).

Sequencing of the cloned PCR products reveals considerable diversity in the Ramos cell line (a prevalence of $2.8 \times 10^{-3}$ mutations $bp^{-1}$ in the $V_H$) although significant heterogeneity is also observed in BL41 as well as in BL2. See FIG. 1A. Sequence diversity in the rearranged $V_H$ genes of four sporadic Burkitt lymphoma lines are shown as pie charts. The rearranged $V_H$ genes in each cell line are PCR amplified and cloned into M13. For each cell line, the consensus is taken as the sequence common to the greatest number of M13 clones and a germline counterpart (indicated above each pie) assigned on the basis of closest match using the VBASE database of human immunoglobulin sequences (Tomlinson, 1997). The $V_H$ consensus sequence for Ramos used herein differs in 3 positions from the sequence determined by Chapman et al (1996), five positions from that determined by Ratech (1992) and six positions from its closest germline counterpart $V_H4$(DP-63).

The analysis of $V_H$ diversity in Ramos is extended by sequencing the products from nine independent PCR amplifications. This enables a likely dynastic relationship between the mutated clones in the population to be deduced, minimising the number of presumed independent repeats of individual nucleotide substitutions (FIG. 1B). 315 M13$V_H$ clones obtained from nine independent PCR amplifications are sequenced; the dynasty only includes sequences identified (rather than presumed intermediates). Individual mutations are designated according to the format "C230" with 230 being the nucleotide position in the Ramos $V_H$ (numbered as in FIG. 3) and the "C" indicating the novel base at that position. The criterion used to deduce the genealogy is a minimisation of the number of independent occurrences of the same nucleotide substitution. The majority of branches contain individual members contributed by distinct PCR amplifications. The rare deletions and duplications are indicated by the prefix "x" and "d" respectively. Arrows highlight two mutations (a substitution at position 264 yielding a stop codon and a duplication at position 184) whose position within the tree implies that mutations can continue to accumulate following loss of functional heavy chain expression.

PCR artefacts make little contribution to the database of mutations; not only is the prevalence of nucleotide substitutions greatly in excess of that observed in control PCR amplifications ($<0.05 \times 10^{-3}$ $bp^{-1}$) but also identically mutated clones (as well as dynastically related ones) are found in independent amplifications. In many cases, generations within a lineage differ by a single nucleotide substitution indicating that only a small number of substitutions have been introduced in each round of mutation.

Analysis of $V_\lambda$, rearrangements reveals that Ramos harbours an in-frame rearrangement of $V_\lambda 2.2$-16 (as described by Chapman et al. 1996)) and an out-of-frame rearrangement of $V_\lambda 2.2$-25. There is mutational diversity in both rearranged $V_\lambda$s although greater diversity has accumulated on the non-functional allele (FIG. 1C).

A classic feature of antibody hypermutation is that mutations largely accumulate in the V region but scarcely in the C. This is also evident in the mutations that have accumulated in the Ramos IgH locus (FIG. 1D). M13 clones containing cDNA inserts extending through $V_H$, Cµ1 and the first 87 nucleotides Cµ2 are generated by PCR from the initial Ramos culture. The Pie charts (presented as in FIG. 1A) depict the extent of mutation identified in the 341 nucleotide stretch of $V_H$ as compared to a 380 nucleotide stretch of Cµ extending from the beginning of Cµ1.

The IgM immunoglobulin produced by Ramos is present both on the surface of the cells and, in secreted form, in the culture medium. Analysis of the culture medium reveals that Ramos secretes immunoglobulin molecules to a very high concentration, approximately 1 µg/ml. Thus, Ramos is capable of secreting immunoglobulins to a level which renders it unnecessary to redone immunoglobulin genes into expression cell lines or bacteria for production.

EXAMPLE 2

$V_H$ Diversification in Ramos is Constitutive

To address whether V gene diversification is ongoing, the cells are cloned and $V_H$ diversity assessed using a MutS-based assay after periods of in vitro culture. The Ramos $V_H$ is PCR amplified and purified as described above using oligonucleotides containing a biotinylated base at the 5'-end. Following denaturation/renaturation (99° C. for 3 nun; 75° C. for 90 min), the extent of mutation is assessed by monitoring the binding of the mismatched heteroduplexed material to the bacterial mismatch-repair protein MutS, filter-bound, with detection by ECL as previously described (Jolly et al., 1997).

The results indicate that $V_H$ diversification is indeed ongoing (see FIG. 2A). DNA is extracted from Ramos cells that have been cultured for 1 or 3 months following limit dilution cloning. The rearranged $V_H$ is PCR amplified using biotinylated oligonucleotides prior to undergoing denaturation/renaturation; mismatched heteroduplexes are then detected by binding to immobilised MutS as previously described (Jolly et al., 1997). An aliquot of the renatured DNA is bound directly onto membranes to confirm matched DNA loading (Total DNA control). Assays performed on the Ramos $V_H$ amplified from a bacterial plasmid template as well as from the initial Ramos culture are included for comparison.

The $V_H$ genes are PCR amplified from Ramos cultures that have been expanded for four (Rc1) or six (Rc13 and 14)

weeks (FIG. 2B). A mutation rate for each clone is indicated and is calculated by dividing the prevalence of independent $V_H$ mutations at 4 or 6 weeks post-cloning by the presumed number of cell divisions based on a generation time of 24 h.

The sequences reveal step-wise mutation accumulation with a mutation rate of about $0.24 \times 10^{-4}$ mutations $bp^{-1}$ generation$^{-1}$.

Direct comparison of the $V_H$ mutation rate in Ramos to that in other cell-lines is not straightforward since there is little information on mutation rates in other lines as judged by unselected mutations incorporated throughout the $V_H$ obtained following clonal expansion from a single precursor cell. However, the prevalence of mutations following a two week expansion of 50 precursor BL2 cells has been determined under conditions of mutation induction ($2.7 \times 10^{-3}$ mutations $bp^{-1}$; Denepoux et al., 1997). Similar experiments performed with Ramos under conditions of normal culture reveal a mutation prevalence of $2.3 \times 10^{-3}$ mutations $bp^{-1}$. Various attempts to enhance the mutation rate by provision of cytokines, helper T cells etc. have proved unsuccessful. Thus, the rate of mutation that can be achieved by specific induction in BL2 cells appears to be similar to the constitutive rate of $V_H$ mutation in Ramos.

EXAMPLE 3

Examination of the Nature of $V_H$ Mutations in Ramos

A database of mutational events is created which combines those detected in the initial Ramos culture (from 141 distinct sequences) with those detected in four subclones that have been cultured in various experiments without specific selection (from a further 135 distinct sequences). This database is created after the individual sets of sequences have been assembled into dynastic relationships (as detailed in the legend to FIG. 1B) to ensure that clonal expansion of an individual mutated cell does not lead to a specific mutational event being counted multiple times. Here an analysis of this composite database of 340 distinct and presumably unselected mutational events (200 contributed by the initial Ramos culture and 140 from the expanded subclones) is described; separate analysis of the initial and subclone populations yields identical conclusions.

The overwhelming majority of the mutations (333 out of 340) are single nucleotide substitutions. A small number of deletions (4) and duplications (3) are observed but no untemplated insertions; these events are further discussed below. There are only five sequences which exhibited nucleotide substitutions in adjacent positions; however, in three of these five cases, the genealogy revealed that the adjacent substitutions have been sequentially incorporated. Thus, the simultaneous creation of nucleotide substitutions in adjacent positions is a rare event.

Figure 3:
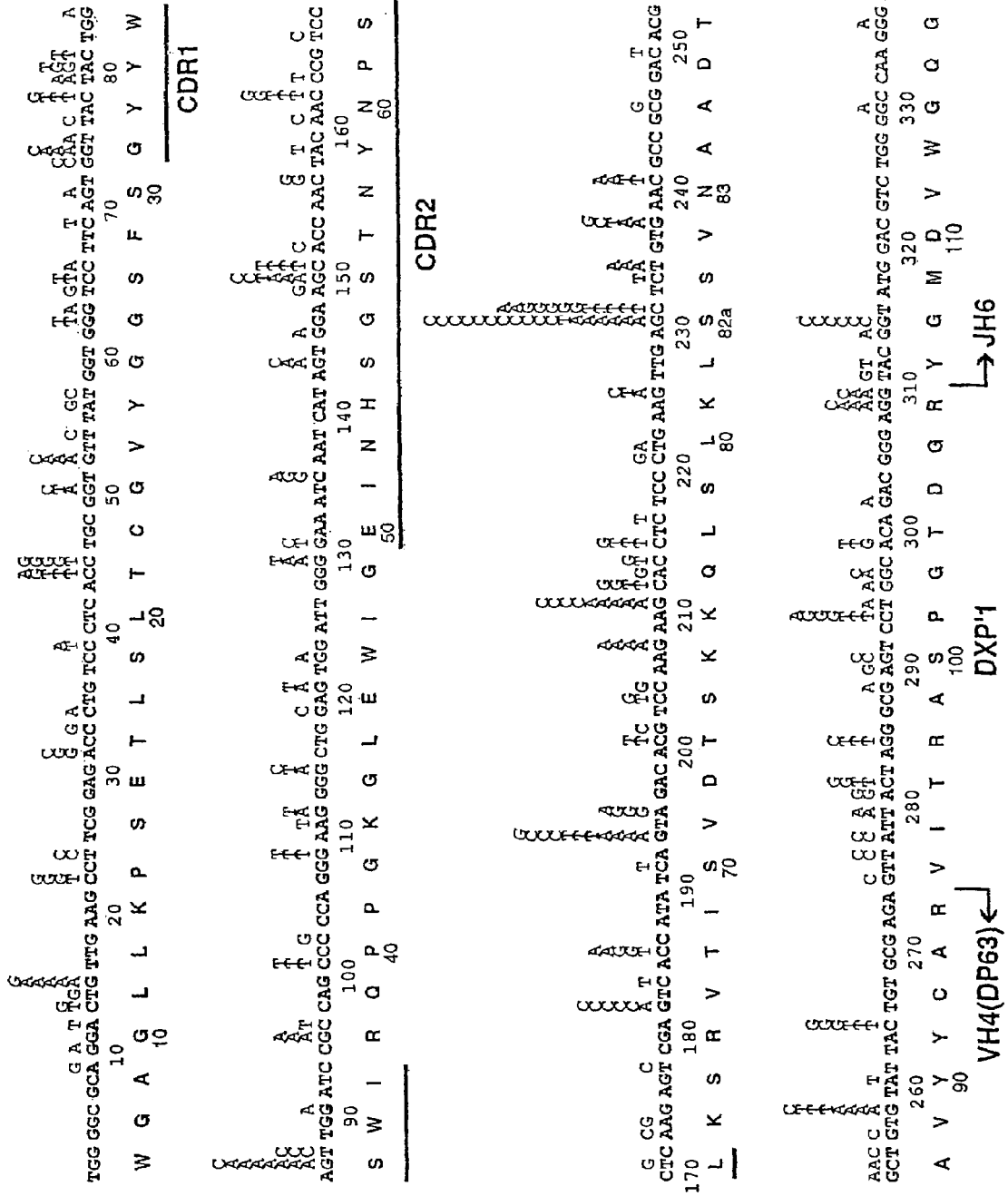
FIG. 3. Distribution of unselected nucleotide substitutions along the Ramos $V_H$ (SEQ ID NO: 15; SEQ ID NO: 128—nucleic acid and amino acid sequences, respectively).

The distribution of the mutations along the $V_H$ is highly non-random (See FIG. 3). Independently occurring base substitutions are indicated at each nucleotide position. The locations of CDR1 and 2 are indicated. Nucleotide positions are numbered from the 3'-end of the sequencing primer with nucleotide position +1 corresponding to the first base of codon 7; codons are numbered according to Kabat. Mutations indicated in italics (nucleotide position 15, 193, 195 and 237) are substitutions that occur in a mutated subclone and have reverted the sequence at that position to the indicated consensus.

The major hotspot is at the G and C nucleotides of the Ser82a codon, which has previously been identified as a major intrinsic mutational hotspot in other $V_H$ genes (Wagner et al., 1995; Jolly et al., 1996) and conforms to the RGYW consensus (Rogozin and Kolchanov, 1992; Betz et al., 1993). Whilst the dominant intrinsic mutational hotspot in many $V_H$ genes is at Ser31, this codon is not present in the Ramos consensus $V_H$ (or its germline counterpart) which have Gly at that position. The individual nucleotide substitutions show a marked bias in favour of transitions (51% rather than randomly-expected 33%). There is also a striking preference for targeting G and C which account for 82% of the nucleotides targeted (Table 1).

TABLE 1

Nucleotide substitution preferences of hypermutation in Ramos

| Parental nucleotide | Frequency of substitution to | | | | |
|---|---|---|---|---|---|
| | T | C | G | A | Total |
| T | — | 3.9 | 1.2 | 3.0 | 8.1 |
| C | 17.4 | — | 12.6 | 4.8 | 34.8 |
| G | 7.2 | 15.9 | — | 24.0 | 47.1 |
| A | 2.4 | 1.8 | 5.7 | — | 9.9 |

Single nucleotide substitutions were computed on the $V_H$ coding strand and are given as the percentage of the total number (333) of independent, unselected nucleotide substitutions identified.

EXAMPLE 4

Selection of Hypermutating Cells by IgM-Loss

Analysis of the Ramos variants reveals several mutations that must have inactivated $V_H$ (see FIG. 1B) suggesting it might be possible for the cells to lose IgM expression but remain viable. If this is the case, Ig expression loss would be an easy means to select a constitutively hypermutating B cell line.

Figure 4:
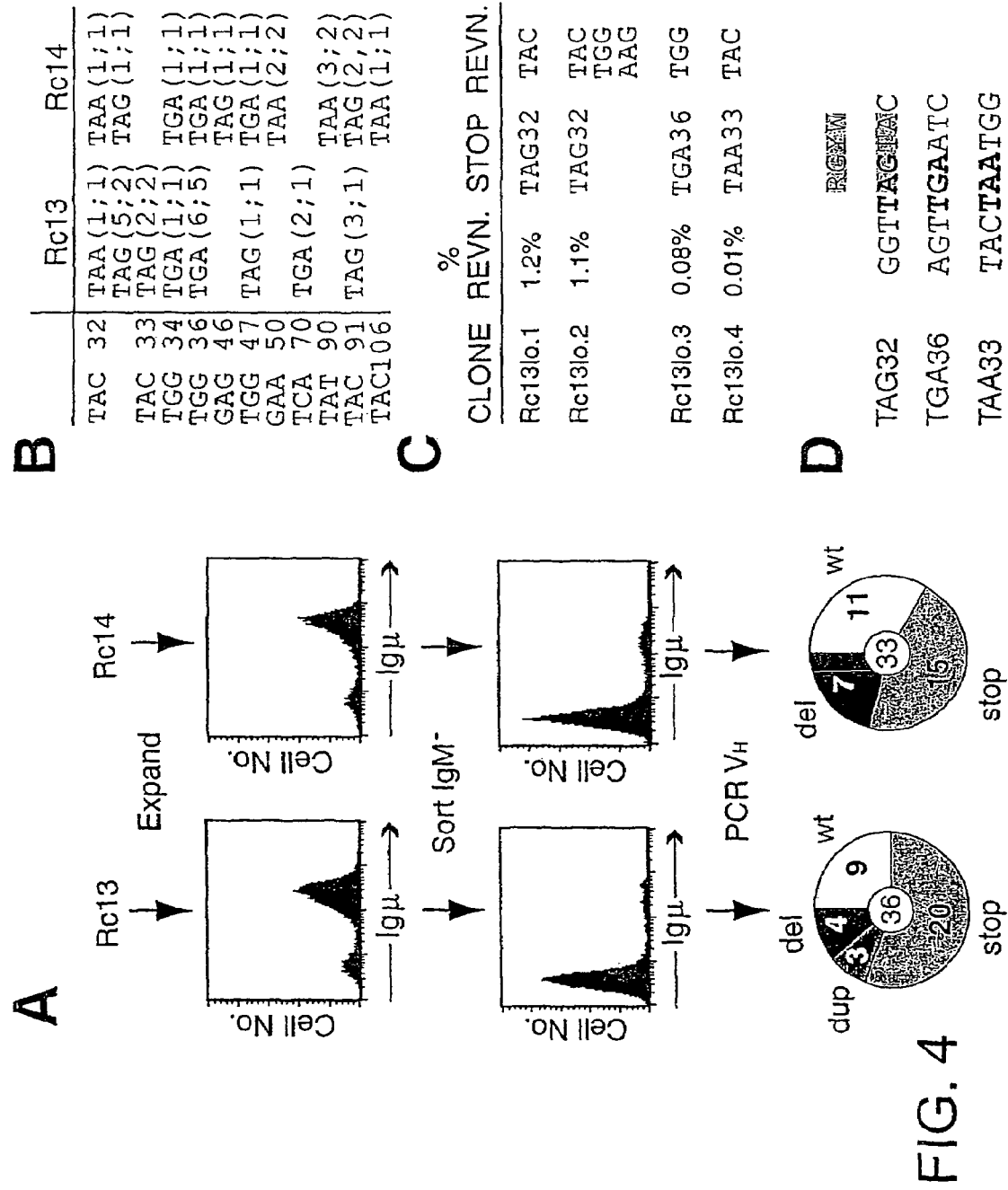
FIG. 4. Hypermutation in Ramos generates diverse revertible IgM-loss variants.
(A) Scheme showing the isolation of IgM-loss variants.
(B) Table showing that multiple nonsense mutations can contribute to $V_H$ inactivation. Each $V_H$ codon position at which stops are observed in these two populations is listed.
(C) Table of reversion rates of IgM-loss variants.
(D) Sequence surrounding the stop codons in the IgM-loss derivatives.

Analysis of the Ramos culture reveals it to contain 8% surface IgM$^-$ cells. Such IgM-loss variants are generated during in vitro culture, as follows. The starting Ramos culture is transfected with a pSV2neo plasmid, diluted into 96-well plates and clones growing in selective medium allowed to expand. Flow cytometry performed on the expanded clones six months after the original transfection reveals the presence of IgM-loss variants, constituting 16% and 18% of the two clonal populations (Rc13 and Rc14) shown here (FIG. 4A). Enrichment by a single round of sorting yields subpopulations that contain 87% (Rc13) and 76% (Rc14) surface IgM-negative cells. Following PCR amplification of the rearranged $V_H$ gene in these subpopulations, sequencing reveals that 75% (Rc13) and 67% (Rc14) of the cloned $V_H$ segments contained a nonsense (stop), deletion (del) or duplication (dup) mutation within the 341 nucleotide $V_H$ stretch analysed. The remainder of the clones are designated wild type (wt) although no attempt is made to discriminate possible $V_H$-inactivating missense mutations. The 4 deletions and 3 duplications identified in the Rc13 population are all distinct whereas only 4 distinct mutations account for the 7 Rc14 sequences determined that harbour deletions. The nature of the deletions and duplications is presented in FIG. 6: each event is named with a letter followed by a number. The letter gives the provenance of the mutation (A, B and C being the cloned TdT$^-$ control transfectants, D, E and F the TdT$^+$ transfectants and U signifies events identified in the initial, unselected Ramos culture); the number indicates the first nucleotide position in the sequence string. Nucleotides deleted are specified above the line and nucleotides added (duplications or non-templated insertions) below the line; single nucleotide substitutions are encircled with the novel base being specified. The duplicated segments of $V_H$ origin are underlined; non-templated insertions are in bold. With several deletions or duplications, the event is flanked by a single nucleotide of unknown provenance. Such flanking changes could well arise by nucleotide substitution (rather than non-templated insertion) and these events therefore separately grouped; the assignment of the single base substitution (encircled) to one or other end of the deletion/duplication is often arbitrary.

Figure 5:
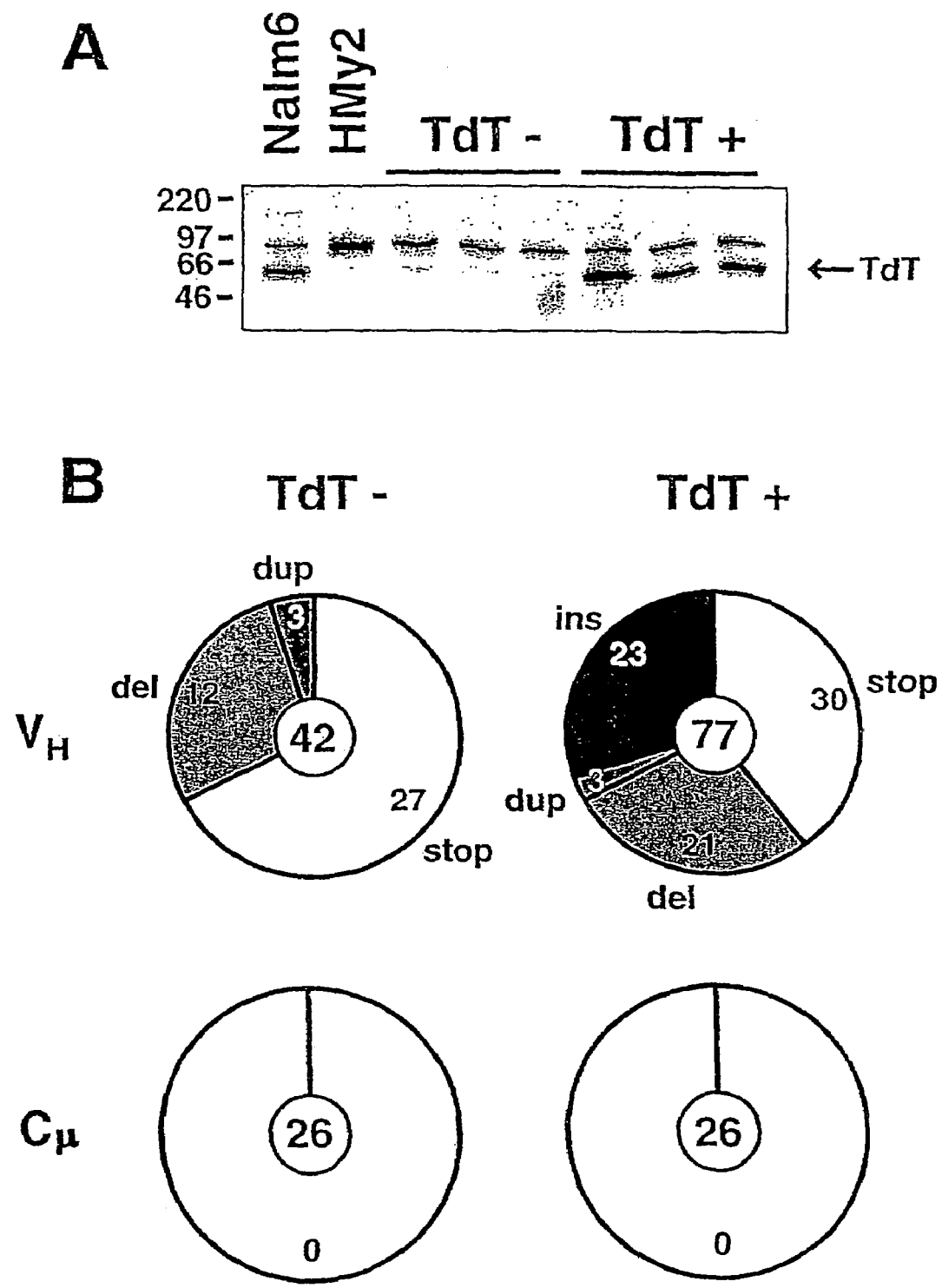
FIG. 5. IgM-loss variants in Ramos transfectants expressing TdT.
(A) Western blot analysis of expression of TdT in three pSV-pβG/TdT and three control transfectants of Ramos.
(B) Pie charts depicting independent mutational events giving rise to IgM-loss variants.

The IgM⁻ cells are enriched in a single round of sorting prior to PCR amplification and cloning of their $V_H$ segments. The sequences reveal a considerable range of $V_H$-inactivating mutations (stop codons or frameshifts) (FIG. 4) although diverse inactivating mutations are even evident in IgM-loss variants sorted after only 6 weeks of clonal expansion (see FIG. 5). In FIG. 5A expression of TdT in three pSV-pβG/TdT and three control transfectants of Ramos is compared by Western blot analysis of nuclear protein extracts. Nalm6 (a TdT-positive human pre-B cell lymphoma) and HMy2 (a TdT-negative mature human B lymphoma) provided controls.

In FIG. 5B, pie charts are shown depicting independent mutational events giving rise to IgM-loss variants. IgM⁻ variants (constituting 1-5% of the population) are obtained by sorting the three TdT⁺ and three TdT⁻ control transfectants that have been cultured for 6 weeks following cloning. The $V_H$ regions in the sorted subpopulations are PCR amplified and sequenced. The pie charts depict the types of mutation giving rise to $V_H$ inactivation with the data obtained from the TdT⁺ and TdT⁻ IgM⁻ subpopulations separately pooled. Abbreviations are as in FIG. 4A except that "ins" indicates clones containing apparently non-templated nucleotide insertions. Clones containing deletions or duplications together with multiple nucleotide non-templated insertions are only included within the "ins" segment of the pie. Only unambiguously distinct mutational events are computed. Thus, of the 77 distinct $V_H$-inactivating mutations identified in the TdT⁺ IgM-loss subpopulations, 30 distinct stop codon mutations are identified; if the same stop codon have been independently created within the IgM-loss population derived from a single Ramos transfectant, this would have been underscored.

The stop codons are created at variety of positions (FIG. 4B) but are not randomly located. FIG. 4B summarises the nature of the stop codons observed in the Rc13 and Rc14 IgM-loss populations. At least eight independent mutational events yield the nonsense mutations which account for 20 out of the 27 non-functional $V_H$ sequences in the Rc13 database; a minimum of ten independent mutational events yield the nonsense mutations which account for 15 of the 22 non-functional $V_H$ sequences in the Rc14 database. The numbers in parentheses after each stop codon give the number of sequences in that database that carry the relevant stop codon followed by the number of these sequences that are distinct, as discriminated on the basis of additional mutations. Analysis of stop codons in IgM-loss variants selected from four other clonal populations reveals stop codon creation at a further five locations within $V_H$. In data obtained in six independent experiments, stop codon creation is restricted to 16 of the 39 possible sites; the DNA sequences at these preferred sites being biased (on either coding or non-coding strand) towards the RGYW consensus.

Not surprisingly, whereas deletions and insertions account for only a small proportion of the mutations in unselected Ramos cultures (see above), they make a much greater contribution when attention is focused on, VT-inactivating mutations. It is notable that a large proportion of the IgM-loss variants can be accounted for by stop-codon/frameshift mutations in the $V_H$ itself. This further supports the proposal that hypermutation in Ramos is preferentially targeted to the immunoglobulin V domain—certainly rather than the C domain or, indeed other genes (such as the Igα/Igβ sheath) whose mutation could lead to a surface IgM⁻ phenotype. It also may well be that the Ramos $V_H$ is more frequently targeted for hypermutation than its productively rearranged $V_λ$, a conclusion supported by the pattern of mutations in the initial culture (FIG. 1C).

Selection of cells by detection of Ig loss variants is particularly useful where those variants are capable of reverting, i.e. of reacquiring their endogenous Ig-expressing ability. The dynasty established earlier (FIG. 1B) suggests not only that IgM-loss cells could arise but also that they might undergo further mutation. To confirm this, IgM-loss variants sorted from Rc13 are cloned by limiting dilution. Three weeks after cloning, the presence of IgM⁺ revertants in the IgM⁻ subclones is screened by cytoplasmic immunofluorescence analysis of 5×10⁴ cells; their prevalence is given (FIG. 4C). These IgM⁺ revertants are then enriched in a single round of sorting and the $V_H$ sequences of the clonal IgM⁻ variant compared to that it of its IgM⁺ revertant descendants.

Cytoplasmic immunofluorescence of ten expanded clonal populations reveals the presence of Ig⁺ revertants at varying prevalence (from 0.005% to 1.2%; FIG. 4C) allowing a mutation rate of 1×10⁻⁴ mutations bp⁻¹ generation⁻¹ to be calculated by fluctuation analysis. This is somewhat greater than the rate calculated by direct analysis of unselected mutations (0.25×10⁻⁴ mutations bp⁻¹ generation⁻¹; see above), probably in part reflecting that different IgM-loss clones revert at different rates depending upon the nature of the disrupting mutation. Indeed, the sequence surrounding the stop codons in the IgM-loss derivatives of Rc13 reveals that TAG32 conforms well to the RGYW consensus (R=purine, Y=pyrimidine and W=A or T; Rogozin and Kolchanov, 1992) which accounts for a large proportion of intrinsic mutational hotspots (Betz et al., 1993) whereas TAA33 and TGA36 do not (FIG. 4D).

EXAMPLE 5

Selection of a Novel Ig Binding Activity

In experiments designed to demonstrate development of novel-binding affinities, it is noted that most members of the Ramos cell line described below express a membrane IgM molecule which binds anti-idiotype antibodies (anti-Id1 and anti-Id2), specifically raised against the Ramos surface IgM. However, a few cells retain a surface IgM, yet fail to bind the anti-idiotype antibody. This is due to an alteration in binding affinity in the surface IgM molecule, such that it no longer binds antibody. Cells which express a surface IgM yet cannot bind antibody can be selected in a single round of cell sorting according to the invention.

This is demonstrated by isolating μ positive/id-negative clones which have lost the capacity to bind to anti-Id2 despite the retention of a surface IgM, by ELISA. The clones are sequenced and in six independent clones a conserved $V_H$ residue, K70, is found to be mutated to N, M or R as follows:

| Clone | Mutation | |
|---|---|---|
| 2 | K70N | AAG-AAC |
|   | S77N | AGC-AAC |
| 4 | K70M | AAG-ATG |
| 9 | S59R | AGT-AGG |
|   | K70N | AAG-AAC |
| 10 | K70N | AAG-AAC |
| 12 | K70N | AAG-AAC |
| 13 | K70R | AAG-AGG |

No mutations were observed in the light chain. Thus, it is apparent that mutants may be selected from the Ramos cell line in which the Ig molecule produced has a single base-pair variation with respect to the parent clone.

Making use of an anti-Id1, a similar population of cells is isolated which retain expression of the Igμ constant region but which have lost binding to the anti-idiotype antibody. These cells are enriched by sorting cytometry and the sequence of $V_H$ determined (FIG. 7). This reveals six mutations when compared with the consensus sequence of the starting population. Two of these mutations result in amino acid sequence changes around CDR3 (R->T at 95 and P->H at 98). Thus, selection of more subtle changes in the immunoglobulin molecule are selectable by assaying for loss of binding.

In further experiments, hypermutating cells according to the invention are washed, resuspended in PBS/BSA ($10^8$ cells in 0.25 ml) and mixed with an equal volume of PBS/BSA containing 10% (v/v) antigen-coated magnetic beads. In the present experiment, streptavidin coated magnetic beads (Dynal) are used. After mixing at 4° C. on a roller for 30 mins, the beads are washed three times with PBS/BSA, each time bringing down the beads with a magnet and removing unbound cells. remaining cells are then seeded onto 96 well plates and expanded up to $10^8$ cells before undergoing a further round of selection. Multiple rounds of cell expansion (accompanied by constitutively-ongoing hypermutation) and selection are performed. After multiple rounds of selection, the proportion of cells which bind to the beads, which is initially at or close to background levels of 0.02%, begins to rise.

After 4 rounds, enrichment of streptavidin binding cells is seen. This is repeated on the fifth round (FIG. 8). The low percentage recovery reflects saturation of the beads with cells since changing the cell:bead ratio from vast excess to 1:2 allows a recovery of approximately 20% from round five streptavidin binding cells (FIG. 9). This demonstrates successful selection of a novel binding specificity from the hypermutating Ramos cell line, by four rounds of iterative selection.

Nucleotide sequencing of the heavy and light chains from the streptavidin binding cells predicts one amino acid change in $V_H$ CDR3 and four changes in $V_L$ (1 in FR1, 2 in CDR1 and 1 in CDR2) when compared with the consensus sequence of the staring population (FIG. 11).

To ensure that the binding of streptavidin is dependent on expression of surface immunoglobulin, immunoglobulin negative variants of the streptavidin binding cells; are enriched by sorting cytometry. This markedly reduces the recovery of streptavidin binding cells with an excess of beads. The cells recovered by the Dynal-streptavidin beads from the sorted negative cells are in fact Igμ positive and most likely represent efficient recovery of Igμ streptavidin binding cells contaminating the immunoglobulin negative sorted cell population.

Preliminary data suggest that the efficiency of recovery is reduced as the concentration of streptavidin on the beads is reduced (FIG. 9). This is confirmed by assaying the recovery of streptavidin binding cells with beads incubated with a range of concentrations of streptavidin (FIG. 10). The percentage of cells recoverable from a binding population is dictated by the ratio of beads to cells. In this experiment the ratio is <1:1 beads:cells.

In a further series of experiments, a further two rounds of selection are completed, talking the total to 7. This is accomplished by reducing the concentration of streptavidin bound to the beads from 50 μg/ml in round 5 to 10 μg/ml in round 7. Although the secretion levels of IgM is comparable for the populations selected in rounds 4 to 7 (FIG. 12), streptavidin binding as assessed by ELISA is clearly greatly increased in rounds 6 and 7, in comparison with round 4 (FIG. 13).

This is confirmed by assessment of binding by Surface Plasmon Resonance on a BiaCore chip coated with streptavidin (FIG. 14). The supernatant from round 7 is injected to flow across the chip at point A, and stopped at point B. At point C, anti-human IgM is injected, to demonstrate that the material bound to the streptavidin is IgM. The gradient A-B represents the association constant, and the gradient B-C to dissociation constant. From the BiaCore trace it is evident that round 6 supernatant displays superior binding characteristics to that isolated from round 4 populations or unselected Ramos cells.

Antibodies from round 6 of the selection process also show improved binding with respect to round 4. Binding of cells from round 6 selections to streptavidin-FITC aggregates, formed by preincubation of the fluorophore with a biotinylated protein, can be visualised by FACS, as shown in FIG. 15. Binding to round 4 populations, unselected. Ramos cells or IgM negative Ramos is not seen, indicating maturation of streptavidin binding.

Use of unaggregated streptavidin-FITC does not produce similar results, with the majority of round 6 cells not binding. This, in agreement with ELISA data, suggests that binding to streptavidin is due to avidity of the antibody binding to an array of antigen, rather than to a monovalent affinity. Higher affinity binders may be isolated by sorting for binding to non-aggregated streptavidin-FITC.

In order to determine the mutations responsible for the increased binding seen in round 6 cells over round 4 cells, the light and heavy chain antibody genes are amplified by PCR, and then sequenced. In comparison with round 4 cells, no changes in the heavy chain genes are seen, with the mutation R103S being conserved. In the light chain, mutations V23F and G24C are also conserved, but an additional mutation is present at position 46. Wild-type Ramos has an Aspartate at this position, whilst round 6 cells have an Alanine. Changes at this position are predicted to affect antigen binding, since residues in this region contribute to CDR2 of the light chain (FIG. 16). It seems likely that mutation D46A is responsible for the observed increase in binding to streptavidin seen in round 6 cells.

EXAMPLE 6

In Vitro Maturation of Ramos Streptavidin Binders

Ram B->Ram C (Selecting with FITC-Poly-Streptavidin)

Approximately $5 \times 10^7$ Ram B cells. (derived from the Ramos cell line to bind Streptavidin coated microbeads) are washed with PBS and incubated on ice in 1 ml of PBS/BSA solution containing Poly-Streptavidin-FITC for 30 minutes (Poly-Streptavidin-FITC is made by adding streptavidin FITC (20 µg/ml protein content) to a biotinylated protein (10 µg/ml) and incubating on ice for a few minutes prior to the addition of cells)

The cells are then washed in ice cold PBS briefly, spun down and resuspended in 500 µl PBS.

The most fluorescent 1% of cells are sorted on a MoFlo cell sorter, and this population of cells is returned to tissue culture medium, expanded to approximately $5 \times 10^7$ cells and the procedure repeated.

After four rounds of sorting with poly-Streptavidin-FITC the cells are binding weakly to Streptavidin-FITC. Sequence of the expressed immunoglobulin V regions from this Ramos cell population reveals that amino acid number 82a in framework three of; the heavy chain V region had changed from Serine to Arginine. This population of cells is called Ram C.

Ram C->Ram D (Selecting with FITC-Streptavidin)

The next few rounds of cell sorting are done as described above but now using streptavidin-FITC (20 µg/ml protein content).

After three rounds of sorting using Streptavidin-FITC the sorted cell population (called Ram D) is binding more strongly to Streptavidin FITC as assayed by FACS. Sequence of the expressed V genes reveals a further amino acid change. In framework three the amino acid at position 65, originally a Serine, has changed to Arginine Ram D->Ram E (Selecting with FITC-Streptavidin and Unlabelled Streptavidin Competition)

A subsequent sorting is done as described above using Streptavidin-FITC. However, after staining the cells on ice for 30 minutes, the cells are washed in ice cold PBS once and then resuspended in 0.5 mg/ml Streptavidin and incubated on ice for 20 minutes. This is in order to compete against the already bound Streptavidin-FITC, such that only Streptavidin-FITC that is strongly bound remains. The cells are then washed once in ice cold PBS and resuspended in 500 µl PBS prior to sorting the most fluorescent 1% population as before.

After repeating this sorting protocol a further two times the Ramos cell population (Ram E) appears to bind quite strongly to Streptavidin-FITC. These cells have acquired another amino acid change in framework one of the expressed heavy chain V gene; the amino acid at position 10 had changed from Glycine to Arginine. Moreover, residue 18 has changed from Leucine to Methionine.

The results of the streptavidin maturation in Ramos cells are shown in FIG. 17.

ELISA Comparison

An ELISA assay performed with the supernatants of the various Ramos cell populations confirms that the IgM antibody expressed and secreted from Ramos cells has been matured in vitro to acquire a strong affinity for streptavidin. The results are set forth in FIG. 18.

EXAMPLE 7

Construction of Transgene Comprising Hypermutation-Directing Sequences

It is known that certain elements of Ig gene loci are necessary for direction of hypermutation events in vivo. For example, the intron enhancer and matrix attachment region Ei/MAR has been demonstrated to play a critical role (Betz et al., 1994). Moreover, the 3' enhancer E3' is known to be important (Goyenechea et al., 1997). However, we have shown that these elements, whilst necessary, are not sufficient to direct hypermutation in a transgene.

In contrast, provision of Ei/MAR and E3' together with additional $J_\kappa$-$C_\kappa$ intron DNA and $C_\kappa$ is sufficient to confer hypermutability. A βG-Cκ transgene is assembled by joining an 0.96 Kb PCR-generated KpnI-SpeI β-globin fragment (that extends from −104 with respect to the β-globin transcription start site to +863 and has artificial KpnI and SpeI restriction sites at its ends) to a subfragment of LκΔ[3'F1] [Betz et al., 1994] that extends from nucleotide 2314 in the sequence of Max et al [1981] through Ei/MAR, $C_\kappa$ and E3', and includes the 3'F1 deletion.

Hypermutation is assessed by sequencing segments of the transgene that are PCR amplified using Pfu polymerase. The amplified region extends from immediately upstream of the transcription start site to 300 nucleotides downstream of $J_\kappa 5$.

This chimeric transgene is well targeted for mutation with nucleotide substitutions accumulating at a frequency similar to that found in a normal Igκ transgene. This transgene is the smallest so far described that efficiently recruits hypermutation and the results indicate that multiple sequences located somewhere in the region including and flanking $C_\kappa$ combine to recruit hypermutation to the 5'-end of the β-globin/Igκ chimaera The recruitment of hypermutation can therefore be solely directed by sequences lying towards the 3'-end of the hypermutation domain. However, the 5'-border of the mutation domain in normal Ig genes in the vicinity of the promoter, some 100-200 nucleotides downstream of the transcription start site. This positioning of the 5'-border of the mutation domain with respect to the start site remains even in the βG-Cκ transgene when the β-globin gene provides both the promoter and the bulk of the mutation domain. These results are consistent with findings made with other transgenes indicating that it is the position of the promoter itself that defines the 5'-border of the mutation domain.

The simplest explanation for the way in which some if not all the κ regulatory elements contribute towards mutation recruitment is to propose that they work by bringing a hypermutation priming factor onto the transcription initiation complex. By analogy with the classic studies on enhancers as transcription regulatory elements, the Igκ enhancers may work as regulators of hypermutation in a position and orientation-independent manner. Indeed, the data obtained with the βG-Cκ transgene together with previous results in which E3' was moved closer to $C_\kappa$ [Betz et al., 1994] reveal that the hypermutation-enhancing activity of E3' is neither especially sensitive to its position or orientation with respect to the mutation domain.

Ei/MAR normally lies towards the 3'-end of the mutation domain. Whilst deletion of Ei/MAR drastically reduces the efficacy of mutational targeting, its restoration to a position upstream of the promoter (and therefore outside the transcribed region) gives a partial rescue of mutation but without apparently affecting the position of the 5'-border of the mutational domain. Independent confirmation of these results was obtained in transgenic mice using a second transgene, tk-neo::Cκ, in which a neo transcription unit (under control of the HSVtk promoter) is integrated into the $C_\kappa$ exon by gene targeting in embryonic stem cells [Zou, et al., 1995]. In this mouse, following $V_\kappa$-$J_\kappa$ joining, the Igκ Ei/MAR is flanked on either side by transcription domains: the V gene upstream and tk::neo downstream. The tk-neo gene is PCR amplified from sorted germinal centre B cells of mice homozygous for the neo insertion.

For the tk-neo insert in tk-neo::Cκmice, the amplified region extends from residues 607 to 1417 [as numbered in plasmid pMCNeo (GenBank accession U43611)], and the nucleotide sequence determined from position 629 to 1329. The mutation frequency of endogenous VJκ rearrangements in tk-nec ::Cκ mice is determined using a strategy similar to that described in Meyer et al., 1996. Endogenous $VJ\kappa_5$ rearrangements are amplified using a Vκ FR3 consensus forward primer (GGACTGCAGTCAGGTTCAGTG-GCAGTGGG (SEQ ID NO: 7)) and an oligonucleotide LκFOR (Gonzalez-Fernandez and Milstein, 1993, *Proc. Nati. Acad. Sci. USA* 90: 9862-9866) that primes back from downstream of the Jκ cluster.

Although the level of mutation of the tk-neo is low and it is Certainly less efficiently targeted for mutation than the 3'-flanking region of rearranged $V_\kappa$ genes in the same cell population, it appears that—as with normal V genes—the mutation domain in the neo gene insert starts somewhat over 100 nucleotides downstream of the transcription start site despite the fact that Ei/MAR is upstream of the promoter.

Thus, transgenes capable of directing hypermutation in a constitutively hypermutating cell line may be constructed using Ei/MAR, E3' and regulatory elements as defined herein found downstream of $J_\kappa$. Moreover, transgenes may be constructed by replacement of or insertion into endogenous V genes, as in the case of the tk-neo::$C_\kappa$ mice, or by linkage of a desired coding sequence to the $J_\kappa$ intron, as in the case of the βG-Cκ transgene.

EXAMPLE 8

Selection of Constitutively Hypermutating Cell Line

As described above, a small proportion of V gene conversion events can lead to the generation of a non-functional Ig gene, most frequently through the introduction of frameshift mutations. Thus, the generation of sIgM loss-variants in the chicken bursal lymphoma cell line, DT40, can be used to give an initial indication of IgV gene: conversion activity. Compared to the parental DT40 line, a mutant that lacks Rad54 shows a considerably diminished proportion of sIgM-loss variants (FIG. 19). A fluctuation analysis performed on multiple clones reveals that the ΔRAD54 line generates sIgM-loss variants at a frequency nearly tenfold less than that of parental DT40 whilst a ΔRAD52 line generates sIgM-loss variants at a similar frequency to wildtype cells (FIG. 19). These observations are in keeping with earlier findings concerning gene conversion in ΔRAD54 and ΔRAD52-DT40 cells (Bezzubova, et al., 1997; Yamaguchi-Iwai et al, 1998).

This analysis is extended to DT40 cells lacking Xrcc2 and Xrcc3. These Rad51 paralogues have been proposed to play a role in the recombination-dependent pathway of DNA damage repair (Liu et al., 1998; Johnson et al, 1999; Brenneman et al., 2000; Takata et al., 2001). Rather than giving rise to a diminished abundance of sIgM-loss variants, the ΔXRCC2 and ΔXRCC3 lines show a much greater accumulation of loss variants than the parental line (FIG. 19). In the case of ΔXRCC2-DT40, transfection of the human Xrcc2 cDNA under control of the human β-globin promoter causes the frequency of generation of sIgM-loss variants to revert to close to wildtype values. FIG. 19 shows the generation of sIgM-loss variants by wildtype and repair-deficient DT40 cells. Flow cytometric analyses of the heterogeneity of sIgM expression in cultures derived by 1 month of clonal expansion of single sIgM$^+$ normal (WT) or repair-deficient (ΔRAD54, ΔRAD52, ΔXRCC2, ΔXRCC3) DT40 cells are shown in panel (a). An analysis of cultures derived from three representative sIgM$^+$ precursor clones is shown for each type of repair-deficient DT40. The percentage of sIgM$^-$ cells in each analysis is indicated with the fluorescence gate set as eightfold below the centre of the sIgM$^+$ peak. Panel (b) shows fluctuation analysis of the frequency of generation of sIgM-loss variants. The abundance of sIgM-loss variants is determined in multiple parallel cultures derived from sIgM$^+$ single cells after 1 month of clonal expansion; median percentages are noted above each data set and indicated by the dashed bar. The [pβG-hXRCC2]ΔXRCC2 transfectants analysed are generated by transfection of pβG-hXRCC2 into sIgM$^+$ DT40-ΔXRCC2 subclones that have 6.4% and 10.2% sIgM cells in the fluctuation analysis. The whole analysis is performed on multiple, independent sIgM$^+$ clones (with distinct, though similar ancestral Vλ sequences) giving, for each repair-deficient line, average median frequencies at which sIgM-loss variants are generated after 1 month of WT (0.4%), ΔRAD54 (0.07%), ΔRAD52 (0.4%), ΔXRCC2 (6%) and ΔXCRCC3 (2%).

Since deficiency in both Xrcc2 and Xrcc3 is associated with chromosomal instability (Liu et al., 1998); Cui et al., 1999; Deans et al., 2000; Griffin et al., 2000), it is possible that the increased frequency of sIgM-loss variants could reflect gross rearrangements or deletions within Ig loci. However, Southern blot analysis of 24 sIgM$^-$ subclones of ΔXRCC3-DT40 does not reveal any loss or alteration of the 6 kb SalI-BamHI fragment containing the rearranged Vλ.

Therefore, to ascertain whether more localised mutations in the V gene could account for the loss of sIgM expression, the rearranged Vλ segments in populations of sIgM$^-$ cells that are sorted from wildtype, ΔXRCC2- and ΔXRCC3- DT40 subclones after one month of expansion are cloned and sequenced.

Cell culture, Transfection and Analysis

DT40 subclone CL18 and mutants thereof are propagated in RPMI 1640 supplemented with 7% foetal calf serum, 0.3% chicken serum (Life Technologies), 50 μM 2-mercaptoethanol, penicillin and streptomycin at 37° C. in 10% $CO_2$. Cell density was maintained at between 0.2-1.0×10$^6$ ml$^{-1}$ by splitting the cultures daily. The generation of the DT40 derivatives carrying targeted gene disruptions has been described elsewhere. (Bezzubova et al., 1997; Yamaguchi-Iwai et al, 1998; Takata et al., 1998, 2000, 2001). Transfectants of ΔXRCC2-DT40 harbouring a pSV2-neo based plasmid that contains the XRCC2 open reading frame (cloned from HeLa cDNA) under control of the β-globin promoter are generated by electroporation.

CL18 is an sIgM$^-$ subclone of DT40 and is the parental clone for the DNA repair-mutants described here. Multiple sIgM⁺ subclones are obtained from both wild type and repair-deficient mutants using a Mo-Flo (Cytomation) sorter after staining with FITC-conjugated goat anti-chicken IgM (Bethyl Laboratories). There is little variation in the initial Vλ sequence expressed by all the sIgM+DT40-CL18 derived repair-deficient cells used in this work since nearly all the sIgM⁺ derivatives have reverted the original CL18 Vλ frameshift by gene conversion using the ψV8 donor (which is most closely related to the frameshifted CL18 CDR1).

Mutation Analysis

Genomic DNA is PCR amplified from 5000 cell equivalents using Pfu Turbo (Stratagene) polymerase and hotstart touchdown PCR [8 cycles at 95° C. 1'; 68-60° C. (at 1° C. per cycle) 1 min.; 72 ° C. 1 min., 30 sec.; 22 cycles @ 94° C., 30 sec."; 60 ° C., 1 min.; 72° C., 1 min., 30 sec.]. The rearranged Vλ is amplified using CVLF6 (5'-CAG-GAGCTCGCGGGGCCGTCACTGATTGCCG (SEQ ID NO:8); priming in the leader-Vλ intron) and CVLR3 (5'-GCGCAAGCTTCCCCAGCCTGCCGCCAAGTCCAAG (SEQ ID NO:9); priming back from 3' of Jλ); the unrearranged Vλ1 using CVLF6 with CVLURR1 (5'-GGAAT-TCTCAGTGGGAGCAGGAGCAG (SEQ ID NO:10)); the rearranged $V_H$ gene using CVH1F1(5'-CGGGAGCTCCGT-CAGCGCTCTCTGTCC (SEQ ID NO:11)) with CJH1R1 (5'-GGGGTACCCGGAGGAGACGATGACTTCGG (SEQ ID NO:12)) and the $C_\lambda$ region using CJCIR1F (5'-GCAGT-TCAAGAATTCCTCGCTGG (SEQ ID NO:13); priming from within the $J_\lambda$ -$C_\lambda$ intron) with CCMUCLAR (5'-GGAGCCATCGATCACCCAATCCAC (SEQ ID NO:14); priming back from within $C_\lambda$). After purification on QIAquick spin columns (Qiagen), PCR products are cut with the appropriate restriction enzymes, cloned into pBluescriptSK and sequenced using the T3 or T7 primers and an AB1377 sequencer (Applied Biosystems). Sequence alignment (Bonfield et at., 1995, supra) with GAP4 allowed identification of changes from the consensus sequence of each clone.

All sequence changes are assigned to one of three categories: gene conversion, point mutation or an ambiguous category. This discrimination rests on the published sequences of the Vλ pseudogenes that could act as donors for gene conversion. The database of such donor sequences is taken from Reynaud et al. (1987) but implementing the modifications (McCormack et al., 1993) pertaining to the Igλ G4 allele appropriate (Kim et al. 1990) to the expressed Igλ in DT40. (The sequences/gene conversions identified in this work supported the validity of this ψVλ sequence database). For each mutation the database of Vλ pseudogenes is searched for potential donors. If no pseudogene donor containing a string ≥9 bp could be found then it is categorised as an untemplated point mutation. If a such a string is identified and there are further mutations which could be explained by the same donor, then all these mutations are assigned to a single gene conversion event. If there are no further mutations then the isolated mutation could have arisen through a conversion mechanism or could have been untemplated and is therefore categorised as ambiguous.

With regard to the Vλ sequences cloned from the sIgM⁻ subpopulations sorted from multiple wildtype DT40 clones, 67% carry mutations: in the majority (73%) of cases, these mutations render the Vλ obviously non-functional, as shown in FIG. 20. Presumably, most of the remaining sIgM⁻ cells carry inactivating mutations either in $V_H$ or outside the sequenced region of Vλ. FIG. 20 shows analyses of Vλ sequences cloned from sIgm-loss variants. In panel (a), comparison of Vλ sequences obtained from, sIgM-loss cells that have been sorted from parental sIgM+clones of normal or Xrcc2-deficient DT40 cells after 1 month of clonal expansion. Each horizontal line represents the rearranged Vλ1/Jλ (427 bp) with mutations classified as described above as point mutations (lollipop), gene conversion tracts (horizontal bar above line) or single nucleotide substitutions which could be a result of point mutation or gene conversion (ambiguous, vertical bar). Hollow boxes straddling the line depict deletions, triangles indicate a duplications. Pie charts are shown in panel (b), depicting the proportion of Vλ sequences that carry different numbers of point mutations (PM), gene conversions (GC) or mutations of ambiguous origin (Amb) amongst sorted sIgM-loss populations derived from wildtype, ΔXRCC2 or ΔXRCC3 DT40 sIgM⁺ clones after 1 month of clonal expansion. The sizes of the segments are proportional to the number of sequences carrying the number of mutations indicated around the periphery of the pie. The total number of Vλ sequences analysed is indicated in the centre of each pie with the data compiled from analysis of four subclones of wildtype DT40, two of ΔXRCC2-DT40 and three of ΔXRCC3-DT40. Deletions, duplications and insertions are excluded from this analysis; in wildtype cells, there are additionally 6 deletions, 1 duplication and 1 insertion. There are no other events in ΔXRCC2-DT40 and a single example each of a 1 bp deletion and a 1 bp insertion in the ΔXRCC3-DT40 database.

Causes of Vλ gene inactivation in wildtype, ΔXRCC2 (ΔX2) and ΔXRCC3 (ΔX3) DT40 cells expressed as a percentage of the total sequences that contained an identified inactivating mutation are set forth in panel (c): Missense mutation (black); Gene conversion-associated frameshift (white); Deletions, insertions or duplication-associated frameshift (grey). Additional mutational events associated with each inactivating mutation are then shown in (d). The data are expressed as the mean number of additional mutations associated with each inactivating mutation with the type of additional mutation indicated as in panel (c). Thus, ΔXRCC2-DT40 has a mean of 1.2 additional point mutations in addition to the index inactivating mutation whereas wildtype DT40 has only 0.07.

As detailed above, the mutations may be classified as being attributable to gene conversion templated by an upstream Vλ pseudogene, to non-templated point mutations or as falling into an ambiguous category. Most (67%) of the inactivating mutations are due to gene conversion although some (15%) are stop codons generated by non-templated point mutations demonstrating that the low frequency of point mutations seen here and elsewhere (Buerstedde et al., (1985); Kim et al., 1990) in DT40 cells is not a PCR artefact but rather reveals that a low frequency of point mutation does indeed accompany gene conversion in wildtype DT40.

A strikingly different pattern of mutation is seen in the Vλ sequences of the sIgM-loss variants from ΔXRCC2-DT40; Nearly all the sequences carry point mutations, typically with multiple point mutations per sequence. A substantial shift towards point mutations is also seen in the sequences from the sIgM ΔXRCC3-DT40 cells. Thus, whereas a Vλ-inactivating mutation in wild type DT40 is most likely to reflect an out of frame gene conversion tract, in ΔXRCC2/3 it is likely to be a missense mutation (FIG. 20c). Furthermore, whereas most of the nonfunctional Vλ sequences obtained from sorted sIgM-loss variants of ΔXRCC2-DT40 (53%) or ΔXRCC3-DT40 (64%) carry additional point mutations in addition to the Vλ-inactivating mutation, such hitchhiking is only rarely observed in the nonfunctional Vλ sequences from the parental DT40 line (7%; FIG. 20d).

All these observations suggest that the high prevalence of sIgM-loss variants in ΔXRCC2/3-DT40 cells simply reflects a very high frequency of spontaneous IgV gene hypermutation in these cells. FIG. 21 represents analyses of Ig sequences cloned from unsorted DT40 populations after one month of clonal expansion. The Vλ sequences obtained from representative, wildtype and ΔXRCC2 DT40 clones are presented in panel (a) with symbols as in FIG. 20. In panel (b), pie charts are shown depicting the proportion of the Vλ sequences carrying different numbers of the various types of mutation as indicated. The data are pooled from analysis of independent clones: wildtype (two clones), ΔXRCC2 (four clones) and ΔXRCC3 (two clones). In addition to the mutations shown, one ΔXRCC2-DT40 sequence contained a 2 bp insertion in the leader intron which was not obviously templated from a donor pseudogene and one ΔXRCC3-DT40 sequence carried a single base pair deletion also in the leader intron.

Mutation at other loci of ΔXRCC2-DT40 is shown in panel (c). Pie charts depict the proportion of sequences derived from 1 month-expanded ΔXRCC2-DT40 cells that carry mutations in the rearranged $V_H$ (272 bp extending from CDR1 to the end of $J_H$) of the rearranged heavy chain of, in the unrearranged Vλ1 on the excluded allele (458 bp) and in the vicinity of Cλ (425 bp extending from the Jλ-Cλ intron into the first 132 bp of Cλ). Analysis of known $V_H$ pseudogene sequences (Reynaud et al., 1989) does not indicate that any of the mutations observed in the rearranged $V_H$ are due to gene conversion, strongly suggesting that they are due to point mutation although this assignment cannot be regarded as wholly definitive. The mutation prevalences in these data sets are: $1.6 \times 10^{-3}$ mutations.bp$^{-1}$ for $V_H$, $0.03 \times 10^{-3}$ for the unrearranged Vλ1 and $0.13 \times 10^{-3}$ for Cλ as compared to $2.0 \times 10^{-3}$ for point mutations in the rearranged Vλ1 in ΔXRCC2-DT40, $0.13 \times 10^{-3}$ for point mutations in rearranged Vλ1 in wildtype DT40 and $0.04 \times 10^{-3}$ for background PCR error.

The distribution of point mutations across Vλ1 is shown in panel (d). The ΔXRCC2-DT40 consensus is indicated in upper case with the first base corresponding to the 76$^{th}$ base pair of the leader intron. Variations found in the ΔXRCC3-DT40 consensus are indicated in italic capitals below. The mutations are shown in lower case letters above the consensus with those from ΔXRCC2-DT40 in black and those from ΔXRCC3-DT40 in mid-grey. All mutations falling into the point mutation and ambiguous categories are included. Correction has been made for clonal expansion as described previously (Takata et al., 1998) so each lower case letter represents an independent mutational event. The majority of the 27 mutations thereby removed from the original database of 158 are at one of the seven major hotspots; the correction for clonality will, if it gives rise to any distortion, lead to a underestimate of hotspot dominance. Of the seven major hotspots (identified by an accumulation of ≧5 mutations), five conform to the AGY consensus sequence on one of the two strands as indicated with black boxes. Nucleotide substitution preferences (given as a percentage of the database of 131 independent events) as shown in panel (e) are deduced from the point mutations in sequences from unselected ΔXRCC2- and ΔXRCC3-DT40. A similar pattern of preferences is evident if the ΔXRCC2/ΔXRCC3 databases are analysed individually.

The spontaneous Vλ mutation frequency in wildtype and ΔXRCC2/3-DT40 cells is analysed by PCR amplifying the rearranged Vλ segments from total (unsorted) DT40 populations that have been expanded for 1 month following subcloning. The result reveals that there is indeed a much higher spontaneous accumulation of mutations in the ΔXRCC2 and ΔXRCC3 cells than in the parental DT40 (FIG. 21a, b). In ΔXRCC2-DT40 cells, mutations accumulate in Vλ at a rate of about $0.4 \times 10^{-4}$ bp$^{-1}$.generation$^{-1}$ (given an approximately 12 hour division time), a value similar to that seen in the constitutively mutating human Burkitt lymphoma line Ramos.

Somatic hypermutation in germinal centre B cells in man and mouse: is preferentially targeted to the rearranged immunoglobulin $V_H$ and $V_L$ segments. A similar situation applies to the point mutations in ΔXRCC2-DT40 cells. Thus, a significant level of apparent point mutation is also seen in the productively rearranged $V_H1$ gene (FIG. 3c). However, this does not reflect a general mutator phenotype since mutation accumulation is much lower in Cλ than in the rearranged Vλ and is also low in the unrearranged Vλ on the excluded allele where the apparent mutation rate does not rise above the background level ascribable to the PCR amplification itself (FIG. 21c).

The distribution of the mutations over the Vλ domain in ΔXRCC2-DT40 cells is strikingly non-random. The mutations, which are predominantly single nucleotide substitutions, show preferential accumulation at hotspots that conform to an AGY (Y=pyrimidine) consensus on one of the two DNA strands (FIG. 21d). They also occur overwhelmingly (96%) at G/C. This G/C-biased, hotspot-focused hypermutation in ΔXRCC2-DT40 cells, although exhibiting somewhat less of a bias in favour of nucleotide transitions, is strikingly similar to the pattern of V gene hypermutation described in cultured human Burkitt lymphoma cells as well as that occurring in vivo in frog, shark and Msh2-deficient mice (Rada et al., 1998; Diaz et al., 2001). The IgV gene hypermutation that occurs in vivo in man and normal mice appears, as previously discussed, to be achieved by this hotspot-focused G/C biased component acting in concert with a mechanism that targets A/T (FIG. 21e).

Thus, whereas the DT40 chicken bursal lymphoma line normally exhibits a low frequency of IgV diversification by gene conversion, a high frequency of constitutive IgV gene somatic mutation (similar in nature to that occurring in human B cell lymphoma models) can be elicited by ablating Xrcc2 or Xrcc3. This provides strong support to the earlier proposal that IgV gene conversion and hypermutation might constitute different ways of resolving a common DNA lesion (Maizels et al., 1995; Weill et al., 1996). Recent data suggest that the initiating lesion could well be a double strand break (Sale & Neuberger, 1998; Papavasilou et at, 2000; Bross et al. 2000) and it would therefore appear significant that both Xrcc2 and Xrcc3 have been implicated in a recombination-dependent pathway of DNA break repair (Liu et al., 1998; Johnson et al., 1999; Pierce et al., 1999; Brennerman et al., 2000; Takata et al., 2001). Indeed, a similar induction of IgV gene: hypermutation in DT40 cells is achieved by ablating another gene: (RAD51B) whose product is implicated in recombination-dependent repair of breaks (Takata et al., 2000) but not by ablating genes for Ku70 and DNA-PK$_{CS}$ which are involved in non-homologous end-joining. FIG. 22 shows the analysis of sIgM-loss variants in DT40 cells deficient in DNA-PK, Ku70 and Rad51B. Fluctuation analysis of the frequency of generation of sIgM-loss variants after 1 month of clonal expansion is shown in panel (a). The median values obtained with wildtype and ΔXRCC2 DT40 are included for comparison. Pie charts depicting the proportion of Vλ sequences amplified from the sIgM-loss variants derived from two sIgM+ Rad51B-deficient DT40 clones that carry various types of mutation as indicated are shown in panel (b). In addition, one sequence carried a 9 bp deletion, one carried a 4 bp duplication and one carried a single base pair insertion.

The results, however, do not simply suggest that, in the absence of Xrcc2, a lesion which would normally be resolved by gene conversion is instead resolved by a process leading: to somatic hypermutation. First, ΔXRCC2-DT40 cells retain the ability to perform IgV gene conversion, albeit at a somewhat reduced level (FIG. 21b). Second, the frequency of hypermutation in ΔXRCC2-DT40 cells is about an order of magnitude greater than the frequency of gene conversion in the parental DT40 line. It is therefore likely that, in normal DT40 cells, only a minor proportion of the lesions in the IgV gene are subjected to templated repair from an upstream pseudogene thereby leading to the gene conversion events observed. We believe that the major proportion of the lesions are subjected to a recombinational repair using the identical V gene located on the sister chromatid as template and which is therefore 'invisible'. This would be consistent with the observations of Papavasiliou and Schatz (2000) who found that detectable IgV gene breaks in hypermutating mammalian B cells are restricted to the G2/S phase. In the absence of Xrcc2, Xrcc3 or Rad51B, we propose that the 'invisible' sister chromatid-dependent recombinational repair is perverted, resulting in hypermutation. Whether this hypermutation reflects that the sister chromatid-dependent recombinational repair becomes error-prone in the absence of Xrcc2/3 or whether it reflects an inhibition of such repair thereby revealing an alternate, non-templated mechanism of break resolution is an issue that needs to be addressed. This question is not only important for an understanding of the mechanism of hypermutation but may also provide insight into the physiological function of the Rad51 paralogues.

EXAMPLE 9

Affinity Maturation in Δxrcc2 DT40 IgM

A population of Xrcc2-deficient DT40 cells which had been expanded for several months was used to determine whether the action of hypermutation on the unique $V_HDJ_H/V_LJ_L$ rearrangement in these cells could generate sufficient functional diversity to allow the evolution of maturing lineages of antibodies to a significant proportion of antigens tested. We used two methods for selection. In a first approach, cells were incubated with soluble aggregates formed by mixing) FITC-streptavidin with different biotinylated antigens (casein, insulin, ovalbumin (Ova), thyroglobulin (Tg) and a rat monoclonal antibody (Ab)); binding variants were then enriched by flow cytometry. Alternatively, variants were selected using magnetic beads coated with S. aureus Protein A or human serum albumin (HSA). None of the antigens tested showed detectable binding to the parental DT40 or its secreted IgM. After six sequential rounds of selection, there were essentially three types of outcome. In the case of insulin and casein, there was no evidence for enrichment of binding variants. In the cases of the rat monoclonal antibody and Protein A, specific binders were obtained. And in the cases of HSA, Ova and Tg, binders were obtained but these exhibited varying degrees of polyreactivity. Thus, in the selection performed using an aggregate of biotinylated rat IgG mAb S7 with FITC-streptavidin (FIG. 23), specific binding was already evident by round three. Subsequent enrichments were performed using the rat IgG S7 mAb directly conjugated to phycoeythrin (PE). The cells obtained in round six (DT-Ab6) were specific for the rat IgG S7 mAb as judged by the lack of staining by a variety of other reagents. ELISA of the culture supernatant demonstrated that the binding of S7 mAb by DT-Ab6 cells was conferred by the DT-Ab6IgM itself (FIG. 23b). This DT-Ab6 IgM is in fact an anti-S7 idiotype. It recognises purified S7 mAb (and can be used for staining permeabilised S7 hybridoma cells) but this interaction is not competable by other rat immunoglobulins (FIG. 23c, d). DT-Ab6 cells could be stained using high dilutions of PES7 mAb conjugate—suggesting a high affinity of interaction. By performing the staining at a fixed ratio of molecules PE-S7 mAb: DT-Ab6 cells but varying the volume, an affinity in the range of 5.8 nM was deduced (FIG. 23f).

Sequence analysis revealed that DT-Ab6 $V_H/V_L$ carry a total of 19 amino acid substitutions compared to the parental DT40 sequence (FIG. 23g).

In the case of the bead selections performed using streptavidin beads coated with biotinylated Protein. A, binding variants were evident by round two (DT-P2; FIG. 24a). However, many of the cells in the DT-P2 population were sticky in that they also bound to various other types of bead that displayed neither streptavidin nor Protein A. Further enrichments using tosylated beads to which Protein A had been directly conjugated yielded a population of cells (DT-P4) that could be stained with a FITC conjugated Protein A aggregate (FIG. 24b). Serial selection for binding to this aggregate by use of flow cytometry gave rise to a population (DT-P9) which could be stained weakly with unaggregated FITC-Protein A; further sorting with FITC-Protein A then gave rise to more brightly staining descendants (FIG. 24b). The IgM secreted by DT-P14 cells (as well as by several of its precursors) bound well to Protein A as judged by both ELISA and immunoprecipitation (FIG. 24c, d). Direct binding assays using radiolabelled Protein A indicated a substantial increase in affinity had occurred between DT-P9 and DT-P14 (FIG. 24e), consistent with the flow cytometric analysis (FIG. 24b). This increase, which is entirely due to a Ala->Val substitution adjacent to $V_H$ CDR2 (FIG. 24h), yields an IgM with an apparent affinity for Protein A of about 0.32 nM (FIG. 24f). Interestingly, the interaction between DT-P IgM and Protein A differs from the well characterised interaction between Protein A and the Fc portion of rabbit IgG not just in the fact that the DT-P/Protein A interaction is with the V rather than C portion of the IgM molecule (mutations are found in $V_H$ not in $C_\mu$) but also in the fact that it is likely that different sites on Protein A are used to interact with DT-P IgM and rabbit IgG since high concentrations of rabbit IgG do not inhibit the staining of DT-P4/P9 cells by FITC-Protein A (FIG. 24g). Indeed, an enhancement of staining is seen, presumably due to aggregation of Protein A by the rabbit IgG.

The sequence of the DT-P14 $V_H/V_L$ reveals 17 amino acid substitutions compared to the parental DT40 sequence. Five of these mutations are shared with the rat idiotype-specific variant DT-Ab6. However, at least four of the five mutations must have occurred independently in the two dynasties (rather than reflecting descent from a common mutated precursor in the pool of Xrcc2-deficient DT40 cells) since these four mutations common to DT-P14 and DT-Ab6 are not found in DT-P4. This tendency to repeat substitutions might in part reflect that mutation in DT40 is largely restricted to the hotspot-focussed GC-biased first phase of mutations (lacking some of the breadth of mutation that we have ascribed to the A/T-biased second phase; Sale and Neuberger, 1998; Rada et al., 1998) although it is also possible that they confer an advantage by predisposing the antibody structure to maturability. It is notable that whilst Xrcc2-deficient DT40 cells retain the ability to perform IgV gene conversion. (albeit at much lower frequency than somatic hypermutation)$_5$, comparison of the V gene sequences in DT-P14 and DT-Ab6 cells (FIG. 24h) with those of the germline V segments (Reynaud et al., 1987; 1989) reveals that the changes are largely (if not exclusively) due to point mutations rather than gene conversions. The cells obtained after six rounds of selection using HSA-derivatised carboxylated magnetic beads (DT-H6) stained not only with FITC-HSA, but also, with FITC-Tg, FITC-Ova and Cychrome-conjugated streptavidin despite the fact that the DT-H6 cell population had never been exposed to these other antigens; further selections with HSA simply increased the brightness of polyspecific staining (FIG. 25a). A similar, though distinct, pattern of polyspecificity was evident in the cell population that had been subjected to flow cytometric enrichment using complexes of FITC-streptavidin with either biotinylated Tg or biotinylated Ova (FIG. 25a, d). Analysis of subpopulations revealed that the apparent polyspecificity is not a reflection of cellular heterogeneity. The polyspecific staining was mediated by the surface IgM itself since sIgM-loss variants lose antigen-binding activity. Furthermore, antigen binding is readily detected by ELISA of the culture supernatants (FIG. 25b, c).

Polyreactive antibodies are well described in man and mouse (both in serum and amongst hybridomas), where the issue has been raised as to whether they constitute a good starting point for the evolution of monospecificity (Casali and Schettino, 1996; Bouvet and Dighiero, 1998). The same issue arises in the in vitro selection system (though without the constraint of avoiding autoimmunity). We therefore tested whether it is possible to evolve the DT-O6 population towards increased specificity for Ova by flow cytometric enrichment for FITC-Ova$_{bright}$/Cychrome-streptavidin$_{dull}$ cells. After multiple rounds of sorting, cells displaying greater specificity for FITC-Ova were obtained (FIG. 25d). It will be interesting to ascertain whether a polyspecific binding population provides a better starting point for the evolution of specificity than the parental DT40 population.

The results presented here clearly demonstrate that hypermutating cell lines can be used for both the derivation and iterative maturation of antibodies in vitro. Given the genetic tractability of DT40, it is possible to extend the application to transfected IgV genes and thereby mature the affinity of existing antibodies. Furthermore, since the hypermutation mechanism can target heterologous genes put in place of the rearranged IgV segment (Yelamos et al., 1995), it may well prove possible to extend the strategy to the maturation of other ligand/receptor pairs. With regard to the de novo selection of antibodies, it is striking that the action of somatic hypermutation on a single $V_H/V_L$ rearrangement has generated a repertoire from which it has been possible to select and mature high affinity binders to two of the seven antigens tested as well as obtain signs of initial low affinity (but maturable) binding to three of the others. This reflects the fact that very low antigen affinities suffice to initiate the selection: these binding sites are then maturable. Clearly, if wishing to extrapolate the approach to allow the in vitro production of high-affinity human monoclonal antibodies, it would be advantageous to exploit the genetic tractability of DT40 so as to generate a primary repertoire that includes more than a single $V_H/V_L$ rearrangement. The results obtained here indicate that this primary repertoire of rearrangements would be orders of magnitude smaller than the primary repertoire used in vivo.

EXAMPLE 10

Isolation of Naturally-Occuring Constitutively Hypermutating EBV Positive BL Cell Lines A survey of naturally occurring EBV$^+$ BL cell lines revealed an absence of a clearly identifiable population of sIgM-loss variants amongst many of them (e.g. Akata, BL74, Chep, Daudi, Raji, and Wan). However, a clear sIgM$^{-/low}$ population was noted in two of these EBV$^+$ cell lines, ELI-BL and BL16, suggesting an intrinsic hypermutation capacity. sIgM expression profiles of Ramos, EHRB, ELI-BL, and BL16 are shown in FIG. 26a. The sIgM$^{-/low}$ cell population is boxed and the percentage of cells therein indicated. Each dot represents one cell. Note that the sizable sIgM$^{-/low}$ population in BL16 is in part due to less intensely staining positive cells, which also occluded fluctuation analyses. ELI-BL harbors a type 2 EBV, resembles germinal center B cells, and expresses a latency gene repertoire consisting only of EBNA1 and the non-coding, EBER and BamA RNAs (Rowe, et al., 1987) BL16 also contains a type 2 virus but, in contrast to ELI-BL, it appears more LCL-like and expresses a full latency gene repertoire (Rooney et al., 1984; Rowe et al., 1987).

Although a clear sIgM$^{-/low}$ population was visible in ELI-BL and BL16 cultures, it was important to address whether these variants could be attributed to bonafide hypermutation. This was assessed by fluctiation analysis. In brief, (sub)clones were transferred to 24 or 48 well plates, maintained with fresh medium for 3 to 8 weeks, and analyzed by washing cells (1-2.5×10$^5$) twice in PBS/3% FBS, staining (30 min on ice) with the relevant antibody or antibody combination (below) and again washing prior to analysis of at least 10$^4$ cells by flow cytometry (FACSCalibur, Becton Dickinson). Antibodies used were R-phycoerythrin-conjugated, goat anti-human IgM (µ-chain specific; Sigma), fluorescein isothiocyanate (FITC)-conjugated, mouse monoclonal anti-Ramos idiotype [ZL16/1 (Zhang et al.,1995); provided generously by M. Cragg and M. J. Glennie, Tenovus Research Laboratory, Southampton], and FITC-conjugated, goat anti-mouse IgM (Southern Biotechnology Associates, Inc.). Data were acquired and analyzed using CellQuest software (Becton Dickinson).

Unless noted otherwise, cells compared in fluctuation analyses were derived, cultured, and analyzed in parallel. The median (as opposed to the mean) percentage of sIgM-loss variants amongst a number of identically-derived (sub) clones is used as an indicator of a cells somatic hypermutation capacity to minimize the effects of early mutational events Fluctuation analysis of ELI-BL subclones revealed that the sIgM$^{-/low}$ variants were indeed being generated at high frequency during in vitro culture (FIG. 26b; each cross represents the percentage of cells falling within the sIgM$^{-/low}$ window following a 1 month outgrowth of a single subclone; the median percentages are indicated), and $V_H$ sequence analysis, in the case of BL16 subclones, confirmed that this instability reflected somatic hypermutation (FIG. 26c). Base substitution mutations are indicated in lower case letters above the 338 bp consensus DNA sequence in triplets of capital letters. Complementarity-determining regions and partial PCR primer sequences are underlined and emboldened, respectively. The corresponding amino acid sequence is indicated by single capital letters. This consensus sequence differs at two positions from GenBank entry gi.2253343 [TCA (Ser20)-TCT and AGC (Ser55)-ACC (Thr)].

Considerable $V_H$ sequence diversity, including several sequences with multiple base substitution mutations, and an overall high $V_H$ mutation frequency indicated that hypermutation is ongoing in BL16. Moreover, despite the relatively small number of $V_H$ sequences sampled, one dynastic relationship could be inferred [$1^{st}$ mutation at Gly54 (G GT-GAT); $2^{nd}$ mutation at Val92 (GTG-ATG)]. Finally, like Ramos, most of the BL16 $V_H$ base substitution mutations occurred at G or C nucleotides (24/33 or 73%) and clustered within the complementarity determining regions (underlined in FIG. 26c). Thus; several hallmarks of ongoing hypermutation were also distinguishable in two natural EBV+ BL cell lines, one expressing a limited latency gene repertoire and the other expressing a full combination. It was therefore clear that somatic hypermutation can proceed unabated even in the presence of EBV.

REFERENCES

Adetugbo, K., Milstein, C. and Secher, D. S. (1977). Molecular analysis of spontaneous somatic mutants. Nature 265, 299-304.

Bahler, D. W. and Levy, R. (1992). Clonal evolution of a follicular lymphoma: Evidence for antigen selection. Proc. Natl. Acad. Sci. USA 89, 6770-6774.

Bass, S., R. Greene, and J. A. Wells. (1990). Hormone Phage: An Enrichment Method for Variant Proteins With Altered Binding Properties. Proteins. 8, 309-314.

Berek, C. and Milstein, C. (1988). The dynamic nature of the antibody repertoire. Immunol. Rev. 105, 5-26.

Betz, A. G., Milstein, C., Gonzalez-Fernandez, A., Pannell, R., Larson, T. and Neuberger, M. S., Cell 1994. 77: 239-248.

Betz, A. G., Neuberger, M. S. and Milstein, C. (1993). Discriminating intrinsic and antigen-selected mutational hotspots in immunoglobulin V genes. Immunol. Today 14, 405-411.

Bezzubova, O., Silbergleit, A., Yamaguchi-Iwai, Y., Takeda, S. & Buerstedde, J.

M. Reduced X-ray resistance and homologous recombination frequencies in a RAD54-/- mutant of the chicken DT40 cell line. Cell 89, 185-193. (1997).

Bonfield, J. K., Smith, K. F. and Staden, R. (1995). A new DNA-sequence assembly program. Nucleic Acids Res. 23, 4992-99.

Bouvet J. P. & Dighiero, G. From natural polyreactive autoantibodies to a la carte monoreactive antibodies to infectious agents: is it a small world after all? Infect. Immun. 66, 1-4 (1998).

Braeuninger, A., Küppers, R, Strickler, J. G., Wacker, H.-H., Rajewsky, K. and Hansmann, M.-L. (1997). Hodgkin and Reed-Sternberg cells in lymphocyte predominant disease represent clonal populations of germinal center-derived tumor B cells. Proc. Natl. Acad. Sci. USA 94, 9337-9342.

Brenneman, M. A., Weiss, A. E., Nickoloff, J. A. & Chen, D. J. XRCC3 is required for efficient repair of chromosome breaks by homologous recombination. Mutat Res 459, 89-97. (2000).

Bross, L., Fulcita, Y., McBlane, F., Demolliere, C., Rajewsky, K. & Jacobs, H. DNA double-strand breaks immunoglobulin genes undergoing somatic hypermutation. Immunity 13, 589-597. (2000)

Brüggemann, M., Radbruch, A. and Rajewsky, K. (1982). Immunoglobulin; V region variants in hybridoma cells. I. Isolation of a variant with altered idiotypic and antigen binding specificity. EMBO J. 1, 629-634.

Buerstedde, J. M., Reynaud, C. A., Humphries, E. H., Olson, W., Ewert, D. L. & Weill, J. C. Light chain gene conversion continues at high rate in an ALV-induced cell line. Embo J9, 921-927. (1990)

Capizzi and Jameson, (1973) Mutat. Res. 17:147-8

Casali P. & Schettino, E. W. Structure and function of natural antibodies. Curr. Top. Microbiol. Immunol. 10, 167-179 (1996).

Chapman, C. J., Mockridge, C. I., Rowe, M., Rickinson, A. B. and Stevenson, F. K. (1995). Analysis of VH genes used by neoplastic B cells in endemic Burkitt's lymphoma shows somatic hypermutation and intraclonal heterogeneity. Blood 85, 2176-2181.

Chapman, K. B. and Szostak, J. W. (1994) Curr. op. Struct. Biol., 4, 618-622.

Chui, Y.-L., Lozano, F., Jarvis, J. M., Pannell, R. and Milstein, C. (1995). A reporter gene to analyse the hypermutation of immunoglobulin genes. J. Mol. Biol. 249, 555-563;

Clackson, T. and Wells, J. A. (1994) Trends Biotechnol, 12, 173-84.

Coffino, P. and Scharff, M. D. (1971). Rate of somatic mutation in immunoglobulin production by mouse myeloma cells. Proc. Natl. Acad. Sci. USA 68, 219-223.

Cui, X., Brenneman, M., Meyne, J., Oshimura, M., Goodwin, E. H. & Chen D. J. The XRCC2 and XRCC3 repair genes are required for chromosome stability in mammalian cells. Mutat Res 434, 75-88. (1999).

Cull, M. G., Miller, J. F. and Schatz, P. J. (1992) Proc Natl Acad Sci USA, 89, 1865-9.

Deans, B., Griffin, C. S., Maconochie, M. & Thacker, J. Xrcc2 is required for genetic stability, embryonic neurogenesis and viability in mice. Embo J 19, 6675-6685. (2000).

Denépoux, S., Razanajaona, D., Blanchard, D., Meffre, G., Capra, J. D., Banchereau, J and Lebecque, S. (1997). Induction of somatic mutation in a human B cell line in vitro. Immunity 6, 35-46.

Diaz, M., Flajnik, M. F. & Klinman, N. Evolution and the molecular basis of somatic hypermutation of antigen receptor genes. Philos Trans R Soc Lond B Biol Sci 356, 67-72. (2001)

Drake, J. W. (1998) Genetics 148:1667-1686.

Ellington, A. D. and Szostak, J. W. (1990) Nature, 346, 81822.

Gold, L., Polisky, B., Uhlenbeck, O. and Yarus, M. (1995) Annu Rev Biochem, 64, 763-97.

Goossens, T., Klein, U. and Küppers, R. (1998). Frequent occurrence of deletions and duplications during somatic hypermutation: Implications for oncogenic translocations and heavy chain disease. Proc. Natl. Acad. Sci. USA 95, 2463-2468

Goyenechea, B., Klix, N., Yélamos, J., Williams, G. T., Riddell, A; Neuberger, M. S. and Milstein, C., EMBO J. 1997. 16, 3987-3994

Green, N. S., Lin, M. M. and Scharff, M. D. (1998). Immunoglobulin hypermutation in cultured cells. Immunol. Rev. 162, 77-87.

Green, R. and Szostak, J. W. (1992) Science, 258, 1910-5.

Griffin, C. S., Simpson, P. J., Wilson, C. R. & Thacker, J. Mammalian recombination-repair genes XRCC2 and XRCC3 promote correct chromosome segregation. Nat Cell Biol 2, 757-761. (2000)

Jain, R., Roncella, S., Hashimoto, S., Carbone, A., Franco di Celle. P., Foa, R., Ferrarini, M and Chiorazzi, N. (1994). A potential role for antigen selection in the clonal evolution of Burkitt's lymphoma. J. Immunol. 153, 45-52.

Johnson, R. D., Liu, N. & Jasin, M. Mammalian XRCC2 promotes the repair of DNA double-strand breaks by homologous recombination. *Nature* 401, 397-399. (1999).

Jolly, C. J., Klix, N. and Neuberger, M. S. (1997). Rapid methods for the analysis of immunoglobulin gene hypermutation: application to transgenic and gene targeted mice. Nucleic Acids Res. 25, 1913-1919.

Jolly, C. J., Wagner, S. D., Rada, C. A., Klix, N., Milstein, C. and Neuberger, M. S. (1996). The targeting of somatic hypermutation. Semin. Immunol. 8, 159-168.

Joyce, G. F. (1994) *Curr. op. Structural Biol.,* 4, 331-336.

Kim, S., Humphries, E. H., Tjoelker, L., Carlson, L. & Thompson, C. B. Ongoing diversification of the rearranged immunoglobulin light-chain gene in: a bursal lymphoma cell line. *Mol Cell Biol* 10, 3224-3231. (1990)

Klein, G., Giovanella, B., Westman, A., Stehlin, J. and Mumford, D. (1975). An EBV negative cell line established from a American Burkitt lymphoma; receptor characteristics, EBV infectability and permanent conversion into EBV-positive sublines by in vitro infection. Intervirology 5319-334.

Klix et al., (1998) Eur. J. Immunol. 28:317-326.

Liu, N., Lamerdin, J. E., Tebbs, R. S., Schild, D., Tucker, J. D., Shen, M. R., Brookman, K. W., Siciliano, M. J., Walter, C. A., Fan, W., Narayana, L. S., Zhou, Z. Q., Adamson, A. W., Sorenson, K. J., Chen, D. J., Jones, N. J. & Thompson, L. H. XRCC2 and XRCC3, new human Rad51-family members, promote chromosome stability and protect against DNA cross-links and other damages. *Mol Cell* 1, 783-793. (1998).

Lundberg, K. S., et al., (1991) Gene 108:1-6.

Luria and Delbreck., (1943) Genetics 28:491-511

Maizels, N. Somatic hypermutation: how many mechanisms diversify V region sequences? *Cell* 83, 9-12. (1995).

Mattheakis, L. C., Bhatt, R. R. and Dower, W. J. (1994) Proc Natl Acad Sci USA, 91, 9022-6.

Matthias, et al., (1989) NAR 17, 6418.

Max, E. E., Maizel, J. V. and Leder, P., *J. Biol. Chem.* 1981. 256: 5116-5120.

McCafferty, J., Griffiths, A. D., Winter, G. and Chiswell, D. J. (1990) Nature, 348, 552-4.

McCormack, W. T., Hurley, E. A. & Thompson, C. B. Germ line maintenance of the pseudogene donor pool for somatic immunoglobulin gene conversion in chickens. *Mol Cell Biol* 13, 821-830. (1993).

McKean, D., Huppi, K., Bell, M., Staudt, L., Gerhard, W. and Weigelt, M. (1984). Generation of antibody diversity in the immune response of BALB/c mice to influenza virus haemagglutinin. Proc. Natl. Acad. Sci. USA 81, 3180-3184.

Moore, M. J. (1995) Nature, 374, 766-7.

Neuberger, M. S. and. Milstein, C. (1995). Somatic hypermutation. Curr. Opin. Immunol. 7, 248-254.

Papavasiliou, F. N. & Schatz, D. G. Cell-cycle-regulated DNA double-stranded breaks in somatic hypermutation of immunoglobulin genes. *Nature* 408, 216-221. (2000).

Parham, P. (ed). (1998). Somatic hypermutation of immunoglobulin genes. Immunological Reviews, Vol. 162 (Copenhagen, Denmark: Munksgaard);

Pierce, A. J., Johnson, R. D., Thompson, L. H. & Jasin, M. XRCC3 promotes omology-directed repair of DNA damage in mammalian cells. *Genes Dev* 13, 2633-2638. (1999).

Rada, C., Ehrenstein, M. R., Neuberger, M. S. & Milstein, C. Hot spot focusing of somatic hypermutation in MSH2-deficient mice suggests two stages of mutational targeting. *Immunity* 9, 135-141. (1998).

Ratech, H. (1992). Rapid cloning of rearranged immunoglobulin heavy chain genes from human B-cell lines using anchored polymerase chain reaction. Biochem. Biophys. Res. Commun. 182, 1260-1263

Reynaud, C. A., Anquez, V., Grimal, H. & Weill, J. C. A. hyperconversion mechanism generates the chicken light chain preimmune repertoire. *Cell* 48, 379-388. (1987).

Reynaud, C. A., Dahan, A., Anquez, V. & Weill, J. C. Somatic hyperconversion diversifies the single $V_H$ gene of the chicken with a high incidence in the D region. *Cell* 59, 171-183 (1989)

Rogozin, I. B. and Kolchanov, N. A. (1992). Somatic hypermutation of immunoglobulin genes. II. Influence of neighbouring base sequences on mutagenesis. Biochem. Biophys. Acta 1171, 11-18.

Rooney, C. M., A. B. Rickinson, D. J. Moss, G. M. Lenoir, and M. A. Epstein. 1984. Paired Epstein-Barr virus-carrying lymphoma and lymphoblastoid cell lines from Burkitt's lymphoma patients: comparative sensitivity to non-specific and to allo-specific cytotoxic responses in vitro. Int J Cancer. 34:339A48

Rowe, M., D. T. Rowe, C. D. Gregory, L. S. Young, P. J. Farrell, H. Rupani, and A. B. Rickinson. 1987. Differences in B cell growth phenotype reflect novel patterns of Epstein-Barr virus latent gene expression in Burkitt's lymphoma cells. Embo J. 6:2743-51

Sale, J. E. & Neuberger, M. S. TdT-accessible breaks are scattered over the immunoglobulin V domain in a constitutively hypermutating B cell line. *Immunity* 9, 859-869. (1998).

Sharpe et al, (1991) EMBO J. 10:2139-2145.

Smith, G. P. (1985) Science, 228, 1,15-7.

Takata, M., Sasaki, M. S., Sonoda, E., Fukushima, T., Morrison, C., Albala, J. S., Swagemakers, S. M., Kanaar, R., Thompson, L. H. & Takeda, S. The Rad51 paralog Rad51B promotes homologous recombinational repair. *Mol Cell Biol* 20, 6476-6482. (2000).

Takata, M., Sasaki, M. S., Sonoda, E., Morrison, C., Hashimoto, M., Utsumi, H., Yamaguchi-Iwai, Y., Shinohara, A. & Takeda, S. Homologous recombination and non-homologous end-joining pathways of DNA double-strand break repair have overlapping roles in the maintenance, of chromosomal integrity in vertebrate cells. *Embo J* 17, 5497-5508. (1998)

Takata, M., Sasaki, M. S., Tachiiri, S., Fukushima, T., Sonoda, E., Schild, D., Thompson, L. H. & Takeda, S. Chromosome Instability and Defective Recombinational Repair in Knockout Mutants of the Five Rad51 Paralogs. *Mol Cell Biol* 21, 2858-2866. (2001).

Tomlinson, I. M. (1997). V Base database of human antibody genes. Medical Research Council, Centre for Protein Engineering, UK. www.mrc-cpe.cam.ac.uk Tuerk, C. and Gold, L. (1990) Science, 249, 505-10.

Wabl, M., Burrows, P. D., von Gabain, A. and Steinberg, C. M. (1985). Hypermutation at the immunoglobulin heavy chain locus in a pre-B-cell line. Proc. Natl. Acad. Sci. USA 82, 479-482.

Wagner, S. D., Milstein, C. and Neuberger, M. S. (1995). Codon bias targets mutation. Nature 376, 732.

Weill, J. C. & Reynaud, C. A. Rearrangement/hypermutation/gene conversion: when, where and why? *Immunol Today* 17, 92-97. (1996)

Wilson, P. C., de Boutellier, O., Liu, Y-J., Potter, K., Banchereau, J., Capra, J. D. and Pascual, V. (1998). Somatic hypermutation introduces insertions and deletions into immunoglobulin V genes. J. Exp. Med. 187, 59-70.

Wu, H., and Kaartinen, M., (1995) Scand. J. Immunol. 42:52-59.

Wu, H., Pelkonen, E., Knuutila, S and Kaartinen M. (1995). A human follicular lymphoma B cell line hypermutates its functional immunoglobulin genes in vitro. Eur. J. Immunol. 25; 3263-3269.

Yamaguchi-Iwai, Y., Sonoda, E., Buerstedde, J. M, Bezzubova, O., Morrison, C., Takata, M., Shinohara, A. & Takeda, S. Homologous recombination, but not DNA repair, is reduced in vertebrate cells deficient in RAD52. Mol Cell Biol 18, 6430-6435. (1998).

Yélamos, J., Klix, N., Goyenechea, B., Lozano, F., Chui, Y. L., González Feranddez, A., Pannell, R., Neuberger, M. S. & Milstein, C (1995). Targeting of non-Ig sequences in place of the V segment by somatic hypermutation. Nature 376, 225-229.

Zhang, L., R. R. French, H. T. Chan, T. L. O'Keefe, M. S. Cragg, M. J. Power, and M. J. Glennie. 1995. The development of anti-CD79 monoclonal antibodies for treatment of B-cell neoplastic disease. Ther Immunol. 2:191-202

Zhu, M., Rabinowitz, J. L., Green, N. S., Kobrin, B. J. and Scharff, M. D. (1995) A well-differentiated B cell line is permissive for somatic mutation of a transfected immunoglobulin heavy-chain gene. Proc. Natl. Acad. Sci. USA 92, 2810-2814.

Zou, X., Xian, J., Popov, A. V., Rosewell, I. R., Muller, M. and Brüggemann, M., Eur. J. Immunol. 1995. 25: 2154-62.

SEQUENCE LISTING

```
<160> NUMBER OF SEQ ID NOS: 130

<210> SEQ ID NO 1
<211> LENGTH: 24
<212> TYPE: DNA
<213> ORGANISM: Artificial
<220> FEATURE:
<223> OTHER INFORMATION: Primer

<400> SEQUENCE: 1
gcggtacctg aggagacggt gacc                                               24

<210> SEQ ID NO 2
<211> LENGTH: 30
<212> TYPE: DNA
<213> ORGANISM: Artificial
<220> FEATURE:
<223> OTHER INFORMATION: primer

<400> SEQUENCE: 2
ccccaagctt cccaggtgca gctacagcag                                         30

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
ccccggtacc agatgagctt ggacttgcgg                                         30

<210> SEQ ID NO 4
<211> LENGTH: 35
<212> TYPE: DNA
<213> ORGANISM: Artificial
<220> FEATURE:
<223> OTHER INFORMATION: Primer

<400> SEQUENCE: 4
ccccaagctt cgggagtgca tccgcccaa ccctt                                    35

<210> SEQ ID NO 5
<211> LENGTH: 30
<212> TYPE: DNA
<213> ORGANISM: Artificial
<220> FEATURE:
<223> OTHER INFORMATION: primer
```

<400> SEQUENCE: 5
ccccaagctt cccagtctgc cctgactcag                              30

<210> SEQ ID NO 6
<211> LENGTH: 30
<212> TYPE: DNA
<213> ORGANISM: Artificial
<220> FEATURE:
<223> OTHER INFORMATION: primer

<400> SEQUENCE: 6
cccctctaga ccacctagga cggtcagctt                              30

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
ggactgcagt caggttcagt ggcagtggg                               29

<210> SEQ ID NO 8
<211> LENGTH: 31
<212> TYPE: DNA
<213> ORGANISM: Artificial
<220> FEATURE:
<223> OTHER INFORMATION: primer

<400> SEQUENCE: 8
caggagctcg cggggccgtc actgattgcc g                            31

<210> SEQ ID NO 9
<211> LENGTH: 34
<212> TYPE: DNA
<213> ORGANISM: Artificial
<220> FEATURE:
<223> OTHER INFORMATION: primer

<400> SEQUENCE: 9
gcgcaagctt ccccagcctg ccgccaagtc caag                         34

<210> SEQ ID NO 10
<211> LENGTH: 26
<212> TYPE: DNA
<213> ORGANISM: Artificial
<220> FEATURE:
<223> OTHER INFORMATION: primer

<400> SEQUENCE: 10
ggaattctca gtgggagcag gagcag                                  26

<210> SEQ ID NO 11
<211> LENGTH: 27
<212> TYPE: DNA
<213> ORGANISM: Artificial
<220> FEATURE:
<223> OTHER INFORMATION: primer

<400> SEQUENCE: 11
cgggagctcc gtcagcgctc tctgtcc                                 27

<210> SEQ ID NO 12

```
<211> LENGTH: 29
<212> TYPE: DNA
<213> ORGANISM: Artificial
<220> FEATURE:
<223> OTHER INFORMATION: primer

<400> SEQUENCE: 12
ggggtacccg gaggagacga tgacttcgg                                           29

<210> SEQ ID NO 13
<211> LENGTH: 23
<212> TYPE: DNA
<213> ORGANISM: Artificial
<220> FEATURE:
<223> OTHER INFORMATION: primer

<400> SEQUENCE: 13
gcagttcaag aattcctcgc tgg                                                 23

<210> SEQ ID NO 14
<211> LENGTH: 24
<212> TYPE: DNA
<213> ORGANISM: Artificial
<220> FEATURE:
<223> OTHER INFORMATION: primer

<400> SEQUENCE: 14
ggagccatcg atcacccaat ccac                                                24

<210> SEQ ID NO 15
<211> LENGTH: 341
<212> TYPE: DNA
<213> ORGANISM: Homo sapiens
<220> FEATURE:
<221> NAME/KEY: misc_feature
<222> LOCATION: (1)..(341)

<400> SEQUENCE: 15
tggggcgcag gactgttgaa gccttcggag accctgtccc tcacctgcgg tgtttatggt          60
gggtccttca gtggttacta ctggagctgg atccgccagc ccccagggaa ggggctggag         120
tggattgggg aaatcaatca tagtggaagc accaactaca acccgtccct caagagtcga         180
gtcaccatat cagtagacac gtccaagaag cagctctccc tgaagttgag ctctgtgaac         240
gccgcggaca cggctgtgta ttactgtgcg agagttatta ctagggcgag tcctggaaca         300
gacgggaggt acggtatgga cgtctggggc caagggacca c                            341

<210> SEQ ID NO 16
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: A62
      Sequence 'tcag tgg' is deleted

<400> SEQUENCE: 16
ggtcctttac ta                                                             12

<210> SEQ ID NO 17
<211> LENGTH: 12
<212> TYPE: DNA
<213> ORGANISM: Homo sapiens
<220> FEATURE:
<221> NAME/KEY: misc_feature
```

```
<222> LOCATION: (7)..(7)
<223> OTHER INFORMATION: A 120
      Nucleotide 'T' at position 7 is deleted

<400> SEQUENCE: 17
gtggatgggg aa                                                          12

<210> SEQ ID NO 18
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: A276
      Nucleotides TGTGNNNNNNNNNNNNNNNNNNNTACT are deleted
      N = nucleotides A, T, G or C

<400> SEQUENCE: 18
tattacaggg cg                                                          12

<210> SEQ ID NO 19
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: A306
      Nucleotide 'C' at position 7 is deleted

<400> SEQUENCE: 19
gaggtaggta tg                                                          12

<210> SEQ ID NO 20
<211> LENGTH: 11
<212> TYPE: DNA
<213> ORGANISM: Homo sapiens
<220> FEATURE:
<221> NAME/KEY: misc_feature
<222> LOCATION: (7)..(7)
<223> OTHER INFORMATION: B93
      Nucleotide G at position 7 is deleted

<400> SEQUENCE: 20
ccgccacccc a                                                           11

<210> SEQ ID NO 21
<211> LENGTH: 11
<212> TYPE: DNA
<213> ORGANISM: Homo sapiens
<220> FEATURE:
<221> NAME/KEY: misc_feature
<222> LOCATION: (7)..(7)
<223> OTHER INFORMATION: B98
      Nucleotide 'C' at position 7 is deleted

<400> SEQUENCE: 21
agcccaggga a                                                           11

<210> SEQ ID NO 22
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: B227
      The sequence 'CTGTG' is deleted
```

```
<400> SEQUENCE: 22
tgagctaacg cc                                                           12

<210> SEQ ID NO 23
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: C82
      The sequence  TGGA.37bp.GAGT is deleted

<400> SEQUENCE: 23
tggagtggat tg                                                           12

<210> SEQ ID NO 24
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: C209
      The sequence 'tctt ccctgaagtt' is  deleted

<400> SEQUENCE: 24
agcaccgagc tc                                                           12

<210> SEQ ID NO 25
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: C187
      The sequence  'GTACACACGTCCAAGA' is  deleted

<400> SEQUENCE: 25
atatcaagca cc                                                           12

<210> SEQ ID NO 26
<211> LENGTH: 11
<212> TYPE: DNA
<213> ORGANISM: Homo sapiens
<220> FEATURE:
<221> NAME/KEY: misc_feature
<222> LOCATION: (7)..(7)
<223> OTHER INFORMATION: U26
      Nucleotides 'CC' are deleted

<400> SEQUENCE: 26
cggagactgc c                                                            11

<210> SEQ ID NO 27
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: U199
      Nucleotides 'AAG' are deleted

<400> SEQUENCE: 27
acgtccaagc ac                                                           12
```

```
<210> SEQ ID NO 28
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: U208
      Nucleotide 'C' at position 7 is deleted.

<400> SEQUENCE: 28
aagcagtttc tc                                                           12

<210> SEQ ID NO 29
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: U268
      The sequence 'GTTATTA' is deleted

<400> SEQUENCE: 29
gcgagactag gg                                                           12

<210> SEQ ID NO 30
<211> LENGTH: 34
<212> TYPE: DNA
<213> ORGANISM: Homo sapiens
<220> FEATURE:
<221> NAME/KEY: misc_feature
<222> LOCATION: (17)..(29)
<223> OTHER INFORMATION: A255
      The sequence 'CGAGAGTTATTA' is inserted between positions 17 and
      29 and is a duplication of nucleotides between positions 5 and
      16.

<400> SEQUENCE: 30
tgtgcgagag ttattacgag agttattact aggg                                   34

<210> SEQ ID NO 31
<211> LENGTH: 166
<212> TYPE: DNA
<213> ORGANISM: Homo sapiens
<220> FEATURE:
<221> NAME/KEY: misc_feature
<222> LOCATION: (18)..(80)
<223> OTHER INFORMATION: N= nucleotide a,g,c or t
<220> FEATURE:
<221> NAME/KEY: misc_feature
<222> LOCATION: (84)..(161)
<223> OTHER INFORMATION: A113 Nucleotides 'agtggat
      tgggnnnnnnnnnnnnnnnnnnnnnnnnnnnnnnn nnnnnnnnnn nnnnnnnnnn
      nnnnnntatc' are inserted between positions 84 and 161 and
      duplicate nucleotides between positions 7 and 83.
<220> FEATURE:
<221> NAME/KEY: misc_feature
<222> LOCATION: (95)..(157)
<223> OTHER INFORMATION: N= nucleotide a,g,c or t

<400> SEQUENCE: 31
ggctggagtg gattgggnnn nnnnnnnnnn nnnnnnnnnn nnnnnnnnnn nnnnnnnnnn        60
nnnnnnnnnn nnnnnnnnnt atcagtggat tgggnnnnnn nnnnnnnnnn nnnnnnnnnn       120
nnnnnnnnnn nnnnnnnnnn nnnnnnnnnn nnnnnntatc agtaga                     166

<210> SEQ ID NO 32
```

```
<211> LENGTH: 30
<212> TYPE: DNA
<213> ORGANISM: Homo sapiens
<220> FEATURE:
<221> NAME/KEY: misc_feature
<222> LOCATION: (16)..(25)
<223> OTHER INFORMATION: U43
      The sequence 'GGTGTTTAT' is inserted and duplicates sequences
      between positions 7 and 16.

<400> SEQUENCE: 32
acctgcggtg tttatggtgt ttatggtggg                                    30

<210> SEQ ID NO 33
<211> LENGTH: 34
<212> TYPE: DNA
<213> ORGANISM: Homo sapiens
<220> FEATURE:
<221> NAME/KEY: misc_feature
<222> LOCATION: (16)..(29)
<223> OTHER INFORMATION: U318
      The sequence 'ACGTCTGGGGCCA' is inserted and duplicates
      sequences between positions 3 and 15

<400> SEQUENCE: 33
ggacgtctgg ggccaacgtc tgggccaag ggac                                34

<210> SEQ ID NO 34
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: D27
      The sequence 'CCTCA' is deleted

<400> SEQUENCE: 34
ggagaccctg cg                                                       12

<210> SEQ ID NO 35
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: D31
      Nucleotide 'A" is deleted at positions 7

<400> SEQUENCE: 35
accctccctg cg                                                       12

<210> SEQ ID NO 36
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: D219
      Nucleotide 'G' is deleted at position 7.

<400> SEQUENCE: 36
cctgaattga gc                                                       12

<210> SEQ ID NO 37
<211> LENGTH: 12
<212> TYPE: DNA
```

```
<213> ORGANISM: Homo sapiens
<220> FEATURE:
<221> NAME/KEY: misc_feature
<222> LOCATION: (7)..(7)
<223> OTHER INFORMATION: D150
      Nucleotide 'C' is deleted at position 7

<400> SEQUENCE: 37
caccaataca ac                                                    12

<210> SEQ ID NO 38
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: D109
      Nucleotide 'C' at position 7 is deleted

<400> SEQUENCE: 38
aaggggtgga gt                                                    12

<210> SEQ ID NO 39
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: E28
      The sequence 'CCTGC' is  deleted.

<400> SEQUENCE: 39
ccctcaggtg tt                                                    12

<210> SEQ ID NO 40
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: E81
      The sequence "ttgg annnnnnnnn nnnnnnnnn nnnnnnnnn nnnnnnnntg
      gag' is deleted

<400> SEQUENCE: 40
ctggagtgga tt                                                    12

<210> SEQ ID NO 41
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: E88
      The sequence  'cgcc' is  deleted

<400> SEQUENCE: 41
tggatcagcc cc                                                    12

<210> SEQ ID NO 42
<211> LENGTH: 11
<212> TYPE: DNA
<213> ORGANISM: Homo sapiens
<220> FEATURE:
<221> NAME/KEY: misc_feature
```

```
<222> LOCATION: (6)..(6)
<223> OTHER INFORMATION: E92
      Nucleotide 'g' at position 6 is deleted

<400> SEQUENCE: 42
cgccaccccc a                                                            11

<210> SEQ ID NO 43
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: E136
      The sequence 'AGTGGAAGCACCAACTA' is deleted

<400> SEQUENCE: 43
aatcatcaac cc                                                           12

<210> SEQ ID NO 44
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: F66
      The sequence 'TGGTTACTACT' is deleted

<400> SEQUENCE: 44
cttcacggag tt                                                           12

<210> SEQ ID NO 45
<211> LENGTH: 12
<212> TYPE: DNA
<213> ORGANISM: Homo sapiens
<220> FEATURE:
<221> NAME/KEY: misc_feature
<222> LOCATION: (7)..(13)
<223> OTHER INFORMATION: F183
      Nucleotides 'ATCAGTA' are deleted between postions 7 and 13
<220> FEATURE:
<221> NAME/KEY: misc_feature
<222> LOCATION: (7)..(13)
<223> OTHER INFORMATION: F183
      The sequence 'ATCAGTA'  is deleted

<400> SEQUENCE: 45
tatcatacac gt                                                           12

<210> SEQ ID NO 46
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: F215
      The sequence  TGAA.18bp.CGCC is deleted

<400> SEQUENCE: 46
tctcccgcgg ac                                                           12

<210> SEQ ID NO 47
<211> LENGTH: 12
<212> TYPE: DNA
<213> ORGANISM: Homo sapiens
<220> FEATURE:
```

```
<221> NAME/KEY: misc_feature
<222> LOCATION: (7)..(7)
<223> OTHER INFORMATION: F267
      Nucleotides 'AG' between are deleted.

<400> SEQUENCE: 47
tgcgagttat ta                                                          12

<210> SEQ ID NO 48
<211> LENGTH: 102
<212> TYPE: DNA
<213> ORGANISM: Homo sapiens
<220> FEATURE:
<221> NAME/KEY: misc_feature
<222> LOCATION: (9)..(50)
<223> OTHER INFORMATION: N = nucleotides A, T, G or C
<220> FEATURE:
<221> NAME/KEY: misc_feature
<222> LOCATION: (54)..(99)
<223> OTHER INFORMATION: D55
      The sequence 'gtggnn nnnnnnnnnn nnnnnnnnnn nnnnnnnnnn nnnnnnnna
      ggg' is inserted between positions 54 and 99 and duplicates
      sequences between positions 5 and 53
<220> FEATURE:
<221> NAME/KEY: misc_feature
<222> LOCATION: (58)..(95)
<223> OTHER INFORMATION: N = nucleotides A, T, G or C

<400> SEQUENCE: 48
tatggtggnn nnnnnnnnnn nnnnnnnnnn nnnnnnnnnn nnnnnnnna ggggtggnnn       60 nnnnnnnnnn nnnnnnnnnn nnnnnnnnnn nnnnagggaa gg                        102

<210> SEQ ID NO 49
<211> LENGTH: 55
<212> TYPE: DNA
<213> ORGANISM: Homo sapiens
<220> FEATURE:
<221> NAME/KEY: misc_feature
<222> LOCATION: (29)..(50)
<223> OTHER INFORMATION: D123
      The sequence 'GGAAATCAATCATAGGGAAGC' is inserted between
      positions 29 and 50 and duplicates sequences between 7 and 28

<400> SEQUENCE: 49
gattggggaa atcaatcata gtggaagcgg aaatcaatca tagggaagca ccaac           55

<210> SEQ ID NO 50
<211> LENGTH: 44
<212> TYPE: DNA
<213> ORGANISM: Homo sapiens
<220> FEATURE:
<221> NAME/KEY: misc_feature
<222> LOCATION: (9)..(19)
<223> OTHER INFORMATION: N = nucleotides A, T, G or C
<220> FEATURE:
<221> NAME/KEY: misc_feature
<222> LOCATION: (23)..(41)
<223> OTHER INFORMATION: F85
      The sequence' ggatnnnnnnnnnnnnccca' is inserted between positions
      23 and 41 and duplicates the sequence between positions 4 and 22
<220> FEATURE:
<221> NAME/KEY: misc_feature
<222> LOCATION: (27)..(37)
<223> OTHER INFORMATION: N = nucleotides A, T, G or C

<400> SEQUENCE: 50
agttggatnn nnnnnnnncc caggatnnnn nnnnnccca ggga                        44

<210> SEQ ID NO 51
<211> LENGTH: 17
```

```
<212> TYPE: DNA
<213> ORGANISM: Homo sapiens
<220> FEATURE:
<221> NAME/KEY: misc_feature
<222> LOCATION: (7)..(12)
<223> OTHER INFORMATION: D3
      The sequence GACCC between positions 7 and 12 replace the
      sequence AGGACTGT

<400> SEQUENCE: 51
ggtcgcgacc ctgaagc                                                    17

<210> SEQ ID NO 52
<211> LENGTH: 130
<212> TYPE: DNA
<213> ORGANISM: Homo sapiens
<220> FEATURE:
<221> NAME/KEY: misc_feature
<222> LOCATION: (9)..(59)
<223> OTHER INFORMATION: N = nucleotides A, T, G or C
<220> FEATURE:
<221> NAME/KEY: misc_feature
<222> LOCATION: (64)..(124)
<223> OTHER INFORMATION: D56
      The sequence 'ggtgggnn nnnnnnnnnn nnnnnnnnnn nnnnnnnnnn
      nnnnnnnnnn nnnnnnnncaggg' is inserted  between positions 64 and
      124 and is a duplicate of the sequence between positions 2 and 63
<220> FEATURE:
<221> NAME/KEY: misc_feature
<222> LOCATION: (70)..(120)
<223> OTHER INFORMATION: N = nucleotides A, T, G or C

<400> SEQUENCE: 52
atggtgggnn nnnnnnnnnn nnnnnnnnnn nnnnnnnnnn nnnnnnnnnn nnnnnnnnca     60
gggggtgggn nnnnnnnnnn nnnnnnnnnn nnnnnnnnnn nnnnnnnnnn nnnnnnnnnc    120
agggaagggg                                                           130

<210> SEQ ID NO 53
<211> LENGTH: 15
<212> TYPE: DNA
<213> ORGANISM: Homo sapiens
<220> FEATURE:
<221> NAME/KEY: misc_feature
<222> LOCATION: (7)..(10)
<223> OTHER INFORMATION: D71
      The nucleotides 'GGG' between positions 7 and 10 replace the
      nucleotide 'A'

<400> SEQUENCE: 53
gtggttgggc tactg                                                      15

<210> SEQ ID NO 54
<211> LENGTH: 15
<212> TYPE: DNA
<213> ORGANISM: Homo sapiens
<220> FEATURE:
<221> NAME/KEY: misc_feature
<222> LOCATION: (7)..(9)
<223> OTHER INFORMATION: D75
      The nucleotides 'GG' between positions 7 and 9 replace the
      nucleotide 'C'

<400> SEQUENCE: 54
ttactaggtg gagtt                                                      15

<210> SEQ ID NO 55
<211> LENGTH: 14
<212> TYPE: DNA
<213> ORGANISM: Homo sapiens
```

```
<220> FEATURE:
<221> NAME/KEY: misc_feature
<222> LOCATION: (6)..(9)
<223> OTHER INFORMATION: D126
     The sequence 'GGG' between positions 6 and 9 replaces the
     sequence 'AATCAATCAT'

<400> SEQUENCE: 55
tgggagggag tgga                                                     14

<210> SEQ ID NO 56
<211> LENGTH: 21
<212> TYPE: DNA
<213> ORGANISM: Homo sapiens
<220> FEATURE:
<221> NAME/KEY: misc_feature
<222> LOCATION: (7)..(15)
<223> OTHER INFORMATION: D223
     The sequence 'GACCCGGC' between positions 7 and 15 replaces the
     sequences 'AG'

<400> SEQUENCE: 56
aagttggacc cggcctctgt g                                             21

<210> SEQ ID NO 57
<211> LENGTH: 42
<212> TYPE: DNA
<213> ORGANISM: Homo sapiens
<220> FEATURE:
<221> NAME/KEY: misc_feature
<222> LOCATION: (15)..(37)
<223> OTHER INFORMATION: D232
     The sequence 'GCCCCCGTCCTGTGAACGCCGC' is inserted between
     positions 15 and 37

<400> SEQUENCE: 57
tctgtgaacg ccgcgccccc gtcctgtgaa cgccgcggac ac                      42

<210> SEQ ID NO 58
<211> LENGTH: 17
<212> TYPE: DNA
<213> ORGANISM: Homo sapiens
<220> FEATURE:
<221> NAME/KEY: misc_feature
<222> LOCATION: (7)..(12)
<223> OTHER INFORMATION: D235
     The sequence 'GGAGG' is inserted between positions 7 and 12

<400> SEQUENCE: 58
gtaaacggag ggccgcg                                                  17

<210> SEQ ID NO 59
<211> LENGTH: 15
<212> TYPE: DNA
<213> ORGANISM: Homo sapiens
<220> FEATURE:
<221> NAME/KEY: misc_feature
<222> LOCATION: (7)..(9)
<223> OTHER INFORMATION: D252
     The sequence 'TCC' between positions 7 and 9 replace the sequence
     'GTATTACTGT'

<400> SEQUENCE: 59
ggctgttccg cgaga                                                    15

<210> SEQ ID NO 60
<211> LENGTH: 16
<212> TYPE: DNA
<213> ORGANISM: Homo sapiens
```

```
<220> FEATURE:
<221> NAME/KEY: misc_feature
<222> LOCATION: (7)..(9)
<223> OTHER INFORMATION: D268
      The nucleotides 'AGG' between positions 7 and 9 replace the
      nucleotides 'GT'

<400> SEQUENCE: 60
gcgagaaggt attatt                                                       16

<210> SEQ ID NO 61
<211> LENGTH: 14
<212> TYPE: DNA
<213> ORGANISM: Homo sapiens
<220> FEATURE:
<221> NAME/KEY: misc_feature
<222> LOCATION: (7)..(8)
<223> OTHER INFORMATION: D332
      The nculeotides 'GG' between psoitions 7 and 8 replace nucleotide
      ' C'

<400> SEQUENCE: 61
ttattaggta gggc                                                         14

<210> SEQ ID NO 62
<211> LENGTH: 11
<212> TYPE: DNA
<213> ORGANISM: Homo sapiens
<220> FEATURE:
<221> NAME/KEY: misc_feature
<222> LOCATION: (7)..(9)
<223> OTHER INFORMATION: D332
      The nucleotides AG' between positions 7 and 9 replace nucleotide
      'C'

<400> SEQUENCE: 62
aagggaagca c                                                            11

<210> SEQ ID NO 63
<211> LENGTH: 14
<212> TYPE: DNA
<213> ORGANISM: Homo sapiens
<220> FEATURE:
<221> NAME/KEY: misc_feature
<222> LOCATION: (6)..(8)
<223> OTHER INFORMATION: E51
      The nucleotides 'GT' replaces the sequence 'AGGA.51bp.CTTC'

<400> SEQUENCE: 63
gggcgcgtag tggt                                                         14

<210> SEQ ID NO 64
<211> LENGTH: 18
<212> TYPE: DNA
<213> ORGANISM: Homo sapiens
<220> FEATURE:
<221> NAME/KEY: misc_feature
<222> LOCATION: (7)..(12)
<223> OTHER INFORMATION: E51
      The sequence AGACC replaces the sequence TGGT.15bp.TACT

<400> SEQUENCE: 64
tgtttaagac cactggag                                                     18

<210> SEQ ID NO 65
<211> LENGTH: 15
<212> TYPE: DNA
<213> ORGANISM: Homo sapiens
<220> FEATURE:
```

```
<221> NAME/KEY: misc_feature
<222> LOCATION: (7)..(9)
<223> OTHER INFORMATION: E80
      The sequence CCC replaces the nucleotide G

<400> SEQUENCE: 65
actggaccct tggat                                                      15

<210> SEQ ID NO 66
<211> LENGTH: 16
<212> TYPE: DNA
<213> ORGANISM: Homo sapiens
<220> FEATURE:
<221> NAME/KEY: misc_feature
<222> LOCATION: (7)..(11)
<223> OTHER INFORMATION: E263
      The sequence GGTG replaces the sequence CGAGAGTTATTACT

<400> SEQUENCE: 66
actgtgggtg agggcg                                                     16

<210> SEQ ID NO 67
<211> LENGTH: 15
<212> TYPE: DNA
<213> ORGANISM: Homo sapiens
<220> FEATURE:
<221> NAME/KEY: misc_feature
<222> LOCATION: (7)..(9)
<223> OTHER INFORMATION: F89
      The sequence AGG replaces the sequence GCCAGCCCCAGGG

<400> SEQUENCE: 67
ggatccagga agggg                                                      15

<210> SEQ ID NO 68
<211> LENGTH: 15
<212> TYPE: DNA
<213> ORGANISM: Homo sapiens
<220> FEATURE:
<221> NAME/KEY: misc_feature
<222> LOCATION: (7)..(9)
<223> OTHER INFORMATION: F168
      The sequence GGG replaces the sequence AGAGTCGAGT

<400> SEQUENCE: 68
cctcaagggc accat                                                      15

<210> SEQ ID NO 69
<211> LENGTH: 17
<212> TYPE: DNA
<213> ORGANISM: Homo sapiens
<220> FEATURE:
<221> NAME/KEY: misc_feature
<222> LOCATION: (7)..(12)
<223> OTHER INFORMATION: F195
      The sequence AGGGC replaces the sequence GTCCAAGAAG

<400> SEQUENCE: 69
agacacaggg ccacctc                                                    17

<210> SEQ ID NO 70
<211> LENGTH: 15
<212> TYPE: DNA
<213> ORGANISM: Homo sapiens
<220> FEATURE:
<221> NAME/KEY: misc_feature
<222> LOCATION: (7)..(9)
<223> OTHER INFORMATION: F199
      The sequence CT replaces the sequence AAGAAG
```

```
<400> SEQUENCE: 70
acgtccctac cctga                                                    15

<210> SEQ ID NO 71
<211> LENGTH: 15
<212> TYPE: DNA
<213> ORGANISM: Homo sapiens
<220> FEATURE:
<221> NAME/KEY: misc_feature
<222> LOCATION: (7)..(9)
<223> OTHER INFORMATION: F242
      The sequence GGA replaces the sequence ACACGGCTGTGTATTACTGT

<400> SEQUENCE: 71
ccgcggggag cgaga                                                    15

<210> SEQ ID NO 72
<211> LENGTH: 17
<212> TYPE: DNA
<213> ORGANISM: Homo sapiens
<220> FEATURE:
<221> NAME/KEY: misc_feature
<222> LOCATION: (7)..(12)
<223> OTHER INFORMATION: F260
      the sequence CGTGA replaces the sequence GTG

<400> SEQUENCE: 72
attactcgtg acgagag                                                  17

<210> SEQ ID NO 73
<211> LENGTH: 15
<212> TYPE: DNA
<213> ORGANISM: Homo sapiens
<220> FEATURE:
<221> NAME/KEY: misc_feature
<222> LOCATION: (7)..(10)
<223> OTHER INFORMATION: F264
      The sequence ACA replaces the sequence GAGAG.46bp.CGTC

<400> SEQUENCE: 73
ctgtgcacat ggggc                                                    15

<210> SEQ ID NO 74
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: B123
      The nucleotide A replaces the nucleotide G

<400> SEQUENCE: 74
gattggaaaa tc                                                       12

<210> SEQ ID NO 75
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: C109
      The nucleotide T replaces nucleotide C

<400> SEQUENCE: 75
aagggttgga gt                                                       12
```

<210> SEQ ID NO 76
<211> LENGTH: 36
<212> TYPE: DNA
<213> ORGANISM: Homo sapiens
<220> FEATURE:
<221> NAME/KEY: misc_feature
<222> LOCATION: (17)..(31)
<223> OTHER INFORMATION: Insertion of the sequence GAAGCCTTCGGAGA that
      duplicates the sequence between position 3 and 16

<400> SEQUENCE: 76
ttgaagcctt cggactgaag ccttcggaga ccctgt                                  36

<210> SEQ ID NO 77
<211> LENGTH: 30
<212> TYPE: DNA
<213> ORGANISM: Homo sapiens
<220> FEATURE:
<221> NAME/KEY: misc_feature
<222> LOCATION: (15)..(25)
<223> OTHER INFORMATION: U180
      Insertion of sequence ACCATATCAG that duplicates the sequence
      between positions 5 and 14

<400> SEQUENCE: 77
agtcaccata tcaaaccata tcagtagaca                                         30

<210> SEQ ID NO 78
<211> LENGTH: 13
<212> TYPE: DNA
<213> ORGANISM: Homo sapiens
<220> FEATURE:
<221> NAME/KEY: misc_feature
<222> LOCATION: (7)..(7)
<223> OTHER INFORMATION: D45
      The sequence GTTTATGGTGGGT is deleted

<400> SEQUENCE: 78
ctgcgcgcct tca                                                           13

<210> SEQ ID NO 79
<211> LENGTH: 13
<212> TYPE: DNA
<213> ORGANISM: Homo sapiens
<220> FEATURE:
<221> NAME/KEY: misc_feature
<222> LOCATION: (8)..(8)
<223> OTHER INFORMATION: D164
      The sequence CAAG is deleted

<400> SEQUENCE: 79
cgtccccagt cga                                                           13

<210> SEQ ID NO 80
<211> LENGTH: 13
<212> TYPE: DNA
<213> ORGANISM: Homo sapiens
<220> FEATURE:
<221> NAME/KEY: misc_feature
<222> LOCATION: (8)..(8)
<223> OTHER INFORMATION: D216
      The sequence AAG.22bp.CGGA is deleted

<400> SEQUENCE: 80
ctcccttcac ggc                                                           13

<210> SEQ ID NO 81

```
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: E11
     The nucleotide 'T' is deleted

<400> SEQUENCE: 81
gactgtaaag cc                                                      12

<210> SEQ ID NO 82
<211> LENGTH: 13
<212> TYPE: DNA
<213> ORGANISM: Homo sapiens
<220> FEATURE:
<221> NAME/KEY: misc_feature
<222> LOCATION: (8)..(8)
<223> OTHER INFORMATION: E54
     The sequence GGG.25bp.GTTG is deleted

<400> SEQUENCE: 82
ttatggagat ccg                                                     13

<210> SEQ ID NO 83
<211> LENGTH: 13
<212> TYPE: DNA
<213> ORGANISM: Homo sapiens
<220> FEATURE:
<221> NAME/KEY: misc_feature
<222> LOCATION: (8)..(8)
<223> OTHER INFORMATION: F188
     The sequence AGACACGTCCAGAA is deleted

<400> SEQUENCE: 83
tatcagggca cct                                                     13

<210> SEQ ID NO 84
<211> LENGTH: 13
<212> TYPE: DNA
<213> ORGANISM: Homo sapiens
<220> FEATURE:
<221> NAME/KEY: misc_feature
<222> LOCATION: (8)..(8)
<223> OTHER INFORMATION: F220
     The sequence TGAGCTCTGTG is deleted

<400> SEQUENCE: 84
ctgaagcaac gcc                                                     13

<210> SEQ ID NO 85
<211> LENGTH: 300
<212> TYPE: DNA
<213> ORGANISM: Homo sapiens

<400> SEQUENCE: 85
cctgcctccg tgtctgggtc tcctggacag tcgatcacca tctcctgcac tggaaccagc    60
agtgacgttg gtggttataa ctatgtctcc tggtaccaac aaaacccagg caaagccccc   120
aaactcatga tttatgatgt cagtaatcgg ccctcaggga tttctaatcg cttctctggc   180
tccaagtctg gcaacacggc ctccctgacc atctctgggc tccaggctga cgacgaggct   240
gattattact gcacctcata tacaaacgac agcaattctc aggtattcgg cggagggacc   300

<210> SEQ ID NO 86
<211> LENGTH: 427
```

<210> SEQ ID NO 86
<211> LENGTH: (not shown)
<212> TYPE: DNA
<213> ORGANISM: Homo sapiens

<400> SEQUENCE: 86

```
ggggccgtca ctgattgccg ttttctcccc tctctcctct ccctctccag gttccctggt      60
gcaggcagcg ctgactcagc cggcctcggt gtcagcaaac ccaggagaaa ccgtcaagat     120
cacctgctcc gggggtggca gctatgctgg aagttactat tatggctggt accagcagaa     180
ggcacctggc agtgcccctg tcactgtgat ctatgacaac accaacagac cctcgaacat     240
cccttcacga ttctccggtt ccctatccga ctccacaaac acattaacca tcactggggt     300
ccgagccgat gacgaggctg tctatttctg tgggaatgca gacaacactg gtgctgcatt     360
tggggccggg acaaccctga ccgtcctagg tgagtcgctg acctcgtctc ggtctttctt     420
cccccat                                                              427
```

<210> SEQ ID NO 87
<211> LENGTH: 372
<212> TYPE: DNA
<213> ORGANISM: Homo sapiens

<400> SEQUENCE: 87

```
gtgcagctgg tggagtctgg gggaggcgtg gtccagcctg ggggtccct gagactctca       60
tgtgcagcct ctggattcac cgtcagtagc aactacatga cctgggtccg ccaggctcca     120
gggaaggggc tggagtgggt gtcacttatt tatagcggtg gtagcacaac atattacgca     180
gagtccgtga agggccgatt caccatctcc agagacaatt ccaaaaacac gatgtatctt     240
caaatgaaca gcctgagagt agaggacacg gctgtgtatt actgtgcggg agacctgaac     300
agcacctcgg tagggactaa taatttctac atggacgtct ggggcaaagg gaccacggtc     360
accgtctcct ca                                                         372
```

<210> SEQ ID NO 88
<211> LENGTH: 9
<212> TYPE: PRT
<213> ORGANISM: Homo sapiens

<400> SEQUENCE: 88

Phe Ile Phe Ser Thr Asn Ala Met Gly
1               5

<210> SEQ ID NO 89
<211> LENGTH: 37
<212> TYPE: PRT
<213> ORGANISM: Homo sapiens

<400> SEQUENCE: 89

Glu Trp Val Ala Gly Ile Asp Asp Asn Gly Ser Asp Thr Arg Tyr Ala
1               5                   10                  15

Pro Ala Val Lys Gly Arg Ala Thr Ile Ser Arg Asp Asn Gly Gln Ser
            20                  25                  30

Thr Val Arg Leu Gln
        35

<210> SEQ ID NO 90
<211> LENGTH: 11
<212> TYPE: PRT
<213> ORGANISM: Homo sapiens

<400> SEQUENCE: 90

```
Thr Lys Cys Ala Tyr Ile Ser Gly Tyr Asp Tyr
1               5                   10

<210> SEQ ID NO 91
<211> LENGTH: 9
<212> TYPE: PRT
<213> ORGANISM: Homo sapiens

<400> SEQUENCE: 91

Phe Ile Phe Ser Ser Asn Ala Met Gly
1               5

<210> SEQ ID NO 92
<211> LENGTH: 37
<212> TYPE: PRT
<213> ORGANISM: Homo sapiens

<400> SEQUENCE: 92

Glu Trp Val Ala Asp Ile Asp Asp Asn Gly Ser Gly Arg Arg Tyr Ala
1               5                   10                  15

Pro Ala Val Lys Gly Arg Ala Thr Ile Ser Arg Asp Asn Gly Gln Ser
                20                  25                  30

Thr Met Arg Leu Gln
            35

<210> SEQ ID NO 93
<211> LENGTH: 11
<212> TYPE: PRT
<213> ORGANISM: Homo sapiens

<400> SEQUENCE: 93

Thr Lys Cys Thr Tyr Ser Ser Asp Tyr Asp Tyr
1               5                   10

<210> SEQ ID NO 94
<211> LENGTH: 43
<212> TYPE: PRT
<213> ORGANISM: Homo sapiens

<400> SEQUENCE: 94

Ala Ser Val Ser Val Asn Pro Gly Glu Thr Val Lys Ile Thr Cys Ser
1               5                   10                  15

Gly Gly Gly Ser Tyr Gly Gly Ser Tyr Tyr Gly Trp Tyr Gln Gln
                20                  25                  30

Lys Ala Pro Gly Ser Ala Pro Val Ser Val Ile
            35                  40

<210> SEQ ID NO 95
<211> LENGTH: 7
<212> TYPE: PRT
<213> ORGANISM: Homo sapiens

<400> SEQUENCE: 95

Arg Phe Ser Gly Ser Leu Ser
1               5

<210> SEQ ID NO 96
<211> LENGTH: 14
<212> TYPE: PRT
<213> ORGANISM: Homo sapiens

<400> SEQUENCE: 96

Ala Val Tyr Phe Cys Gly Asn Ala Asp Asn Ser Gly Ala Ala
```

```
<210> SEQ ID NO 97
<211> LENGTH: 43
<212> TYPE: PRT
<213> ORGANISM: Homo sapiens

<400> SEQUENCE: 97

Ala Ser Val Ser Ala Lys Pro Gly Glu Thr Val Lys Ile Thr Cys Ser
1               5                   10                  15
Gly Gly Gly Arg Tyr Ile Gly Arg Tyr Tyr Gly Trp Tyr Gln Gln
            20                  25                  30
Lys Thr Pro Gly Ser Ala Pro Val Ser Met Ile
            35                  40

<210> SEQ ID NO 98
<211> LENGTH: 7
<212> TYPE: PRT
<213> ORGANISM: Homo sapiens

<400> SEQUENCE: 98

Arg Phe Ser Thr Ser Leu Ser
1               5

<210> SEQ ID NO 99
<211> LENGTH: 14
<212> TYPE: PRT
<213> ORGANISM: Homo sapiens

<400> SEQUENCE: 99

Ala Val Tyr Val Cys Gly Asn Val Asp Asn Gly Ala Ala
1               5                   10

<210> SEQ ID NO 100
<211> LENGTH: 8
<212> TYPE: PRT
<213> ORGANISM: Homo sapiens

<400> SEQUENCE: 100

Pro Gly Gly Ala Leu Ser Leu Val
1               5

<210> SEQ ID NO 101
<211> LENGTH: 14
<212> TYPE: PRT
<213> ORGANISM: Homo sapiens

<400> SEQUENCE: 101

Ser Thr Asn Ala Met Gly Trp Val Arg Gln Ala Pro Asp Lys
1               5                   10

<210> SEQ ID NO 102
<211> LENGTH: 30
<212> TYPE: PRT
<213> ORGANISM: Homo sapiens

<400> SEQUENCE: 102

Asp Asn Gly Ser Asp Thr Arg Tyr Ala Pro Ala Val Lys Gly Arg Ala
1               5                   10                  15
Thr Ile Ser Arg Asp Asn Gly Gln Ser Thr Val Arg Leu Gln
            20                  25                  30

<210> SEQ ID NO 103
```

```
<211> LENGTH: 8
<212> TYPE: PRT
<213> ORGANISM: Homo sapiens

<400> SEQUENCE: 103

Ala Tyr Ile Ser Gly Tyr Asp Tyr
1               5

<210> SEQ ID NO 104
<211> LENGTH: 8
<212> TYPE: PRT
<213> ORGANISM: Homo sapiens

<400> SEQUENCE: 104

Pro Gly Gly Pro Leu Arg Leu Val
1               5

<210> SEQ ID NO 105
<211> LENGTH: 14
<212> TYPE: PRT
<213> ORGANISM: Homo sapiens

<400> SEQUENCE: 105

Ser Thr Asn Ala Met Gly Trp Val Arg Gln Ala Pro Asp Lys
1               5                   10

<210> SEQ ID NO 106
<211> LENGTH: 30
<212> TYPE: PRT
<213> ORGANISM: Homo sapiens

<400> SEQUENCE: 106

Asp Asp Gly Ser Asp Thr Arg Tyr Ala Pro Ala Val Lys Gly Arg Ala
1               5                   10                  15

Thr Ile Ser Arg Asp Asn Gly Gln Arg Thr Val Arg Leu Gln
            20                  25                  30

<210> SEQ ID NO 107
<211> LENGTH: 8
<212> TYPE: PRT
<213> ORGANISM: Homo sapiens

<400> SEQUENCE: 107

Ala Tyr Ile Ser Gly Cys Asp Tyr
1               5

<210> SEQ ID NO 108
<211> LENGTH: 8
<212> TYPE: PRT
<213> ORGANISM: Homo sapiens

<400> SEQUENCE: 108

Pro Gly Gly Pro Leu Arg Leu Val
1               5

<210> SEQ ID NO 109
<211> LENGTH: 14
<212> TYPE: PRT
<213> ORGANISM: Homo sapiens

<400> SEQUENCE: 109

Ser Thr Asn Ala Met Gly Trp Val Arg Gln Ala Pro Asp Lys
1               5                   10
```

```
<210> SEQ ID NO 110
<211> LENGTH: 30
<212> TYPE: PRT
<213> ORGANISM: Homo sapiens

<400> SEQUENCE: 110

Asp Asp Gly Ser Asp Thr Arg Tyr Ala Pro Ala Val Lys Gly Arg Ala
1               5                   10                  15

Thr Ile Ser Arg Asp Asn Gly Gln Arg Thr Val Ser Leu Gln
            20                  25                  30

<210> SEQ ID NO 111
<211> LENGTH: 8
<212> TYPE: PRT
<213> ORGANISM: Homo sapiens

<400> SEQUENCE: 111

Ala Tyr Ile Ser Gly Cys Asp Tyr
1               5

<210> SEQ ID NO 112
<211> LENGTH: 8
<212> TYPE: PRT
<213> ORGANISM: Homo sapiens

<400> SEQUENCE: 112

Pro Gly Gly Pro Leu Arg Leu Val
1               5

<210> SEQ ID NO 113
<211> LENGTH: 14
<212> TYPE: PRT
<213> ORGANISM: Homo sapiens

<400> SEQUENCE: 113

Ser Ser Asn Ala Met Gly Trp Val Arg Gln Ala Pro Gly Lys
1               5                   10

<210> SEQ ID NO 114
<211> LENGTH: 30
<212> TYPE: PRT
<213> ORGANISM: Homo sapiens

<400> SEQUENCE: 114

Asp Asp Gly Ser Gly Thr Arg Tyr Ala Pro Ala Val Lys Gly Arg Ala
1               5                   10                  15

Thr Ile Ser Arg Asp Asn Gly Gln Arg Thr Val Ser Leu Gln
            20                  25                  30

<210> SEQ ID NO 115
<211> LENGTH: 8
<212> TYPE: PRT
<213> ORGANISM: Homo sapiens

<400> SEQUENCE: 115

Ala Tyr Ile Ser Gly Cys Asp Tyr
1               5

<210> SEQ ID NO 116
<211> LENGTH: 8
<212> TYPE: PRT
<213> ORGANISM: Homo sapiens

<400> SEQUENCE: 116
```

```
Pro Gly Gly Pro Leu Arg Leu Val
1               5
```

<210> SEQ ID NO 117
<211> LENGTH: 14
<212> TYPE: PRT
<213> ORGANISM: Homo sapiens

<400> SEQUENCE: 117

```
Ser Ser Asn Ala Met Gly Trp Val Arg Gln Ala Pro Gly Lys
1               5                   10
```

<210> SEQ ID NO 118
<211> LENGTH: 30
<212> TYPE: PRT
<213> ORGANISM: Homo sapiens

<400> SEQUENCE: 118

```
Asp Asp Gly Ser Gly Thr Arg Tyr Ala Pro Ala Val Lys Gly Arg Val
1               5                   10                  15

Thr Ile Ser Arg Asp Asn Gly Gln Arg Thr Val Ser Leu Gln
            20                  25                  30
```

<210> SEQ ID NO 119
<211> LENGTH: 8
<212> TYPE: PRT
<213> ORGANISM: Homo sapiens

<400> SEQUENCE: 119

```
Ala Tyr Ile Ser Gly Cys Asp Tyr
1               5
```

<210> SEQ ID NO 120
<211> LENGTH: 43
<212> TYPE: PRT
<213> ORGANISM: Homo sapiens

<400> SEQUENCE: 120

```
Ala Ser Val Ser Val Asn Pro Gly Glu Thr Val Lys Ile Thr Cys Ser
1               5                   10                  15

Gly Gly Gly Ser Tyr Gly Gly Ser Tyr Tyr Tyr Gly Trp Tyr Gln Gln
            20                  25                  30

Lys Ala Pro Gly Ser Ala Pro Val Ser Val Ile
            35                  40
```

<210> SEQ ID NO 121
<211> LENGTH: 20
<212> TYPE: PRT
<213> ORGANISM: Homo sapiens

<400> SEQUENCE: 121

```
Asp Asp Glu Ala Val Tyr Phe Cys Gly Asn Ala Asp Asn Ser Gly Ala
1               5                   10                  15

Ala Phe Gly Ala
            20
```

<210> SEQ ID NO 122
<211> LENGTH: 43
<212> TYPE: PRT
<213> ORGANISM: Homo sapiens

<400> SEQUENCE: 122

```
Ala Ser Val Ser Val Asn Pro Gly Glu Thr Val Lys Ile Thr Cys Ser
```

```
                1               5                  10                 15
Gly Gly Gly Arg Tyr Gly Gly Ser Tyr Tyr Gly Trp Tyr Gln Gln
                20                 25                 30

Lys Ala Pro Gly Ser Ala Pro Val Ser Val Ile
            35                  40

<210> SEQ ID NO 123
<211> LENGTH: 20
<212> TYPE: PRT
<213> ORGANISM: Homo sapiens

<400> SEQUENCE: 123

Asp Asp Glu Ala Val Tyr Phe Cys Gly Asn Ala Asp Asn Ser Gly Ala
1               5                   10                  15

Ala Phe Gly Ala
            20

<210> SEQ ID NO 124
<211> LENGTH: 43
<212> TYPE: PRT
<213> ORGANISM: Homo sapiens

<400> SEQUENCE: 124

Ala Ser Val Ser Ala Asn Pro Gly Glu Thr Val Lys Ile Thr Cys Ser
1               5                   10                  15

Gly Gly Gly Arg Tyr Gly Ala Ser Tyr Tyr Val Trp Tyr Gln Gln
                20                  25                 30

Lys Ala Pro Gly Ser Ala Pro Val Ser Val Ile
            35                  40

<210> SEQ ID NO 125
<211> LENGTH: 20
<212> TYPE: PRT
<213> ORGANISM: Homo sapiens

<400> SEQUENCE: 125

Asp Asp Glu Ala Val Tyr Phe Cys Gly Asn Ala Asp Asn Ser Gly Ala
1               5                   10                  15

Ala Phe Gly Ala
            20

<210> SEQ ID NO 126
<211> LENGTH: 43
<212> TYPE: PRT
<213> ORGANISM: Homo sapiens

<400> SEQUENCE: 126

Ala Ser Val Ser Ala Asn Pro Gly Glu Thr Val Lys Ile Thr Cys Ser
1               5                   10                  15

Gly Gly Gly Arg Tyr Gly Ala Ser Tyr Tyr Val Trp Tyr Gln Gln
                20                  25                 30

Lys Ala Pro Gly Ser Ala Pro Val Thr Val Ile
            35                  40

<210> SEQ ID NO 127
<211> LENGTH: 20
<212> TYPE: PRT
<213> ORGANISM: Homo sapiens

<400> SEQUENCE: 127

Asp Asp Glu Ala Val Tyr Phe Cys Gly Asn Ala Asp Asn Ser Gly Ala
```

```
                1               5                   10                  15
Ala Phe Gly Ala
            20

<210> SEQ ID NO 128
<211> LENGTH: 114
<212> TYPE: PRT
<213> ORGANISM: Homo sapiens

<400> SEQUENCE: 128

Trp Gly Ala Gly Leu Leu Lys Pro Ser Glu Thr Leu Ser Leu Thr Cys
1               5                   10                  15

Gly Val Tyr Gly Gly Ser Phe Ser Gly Tyr Tyr Trp Ser Trp Ile Arg
            20                  25                  30

Gln Pro Pro Gly Lys Gly Leu Glu Trp Ile Gly Glu Ile Asn His Ser
        35                  40                  45

Gly Ser Thr Asn Tyr Asn Pro Ser Leu Lys Ser Arg Val Thr Ile Ser
    50                  55                  60

Val Asp Thr Ser Lys Lys Gln Leu Ser Leu Lys Leu Ser Ser Val Asn
65                  70                  75                  80

Ala Ala Asp Thr Ala Val Tyr Tyr Cys Ala Arg Val Ile Thr Arg Ala
                85                  90                  95

Ser Pro Gly Thr Asp Gly Arg Tyr Gly Met Asp Val Trp Gly Gln Gly
            100                 105                 110

Thr Thr

<210> SEQ ID NO 129
<211> LENGTH: 100
<212> TYPE: PRT
<213> ORGANISM: Homo sapiens

<400> SEQUENCE: 129

Pro Ala Ser Val Ser Gly Ser Pro Gly Gln Ser Ile Thr Ile Ser Cys
1               5                   10                  15

Thr Gly Thr Ser Ser Asp Val Gly Gly Tyr Asn Tyr Val Ser Trp Tyr
            20                  25                  30

Gln Gln Asn Pro Gly Lys Ala Pro Lys Leu Met Ile Tyr Asp Val Ser
        35                  40                  45

Asn Arg Pro Ser Gly Ile Ser Asn Arg Phe Gly Ser Ser Lys Ser Gly
    50                  55                  60

Asn Thr Ala Ser Leu Thr Ile Ser Gly Leu Gln Ala Asp Asp Glu Ala
65                  70                  75                  80

Asp Tyr Tyr Cys Thr Ser Tyr Thr Asn Asp Ser Asn Ser Gln Val Phe
                85                  90                  95

Gly Gly Gly Thr
            100

<210> SEQ ID NO 130
<211> LENGTH: 124
<212> TYPE: PRT
<213> ORGANISM: Homo sapiens

<400> SEQUENCE: 130

Val Gln Leu Val Glu Ser Gly Gly Gly Val Val Gln Pro Gly Gly Ser
1               5                   10                  15

Leu Arg Leu Ser Cys Ala Ala Ser Gly Phe Thr Val Ser Ser Asn Tyr
            20                  25                  30
```

```
-continued

Met Thr Trp Val Arg Gln Ala Pro Gly Lys Gly Leu Glu Trp Val Ser
        35                  40                  45

Leu Ile Tyr Ser Gly Gly Ser Thr Thr Tyr Tyr Ala Glu Ser Val Lys
    50              55                  60

Gly Arg Phe Thr Ile Ser Arg Asp Asn Ser Lys Asn Thr Leu Gln Met
65              70                  75                      80

Asn Ser Leu Arg Val Glu Asp Thr Met Asn Ser Val Arg Val Glu Asp
            85                  90                      95

Thr Ala Val Asn Ser Thr Ser Val Gly Thr Asn Asn Phe Tyr Met Asp
            100             105                 110

Val Trp Gly Lys Gly Thr Thr Val Thr Val Ser Ser
            115             120
```

The invention claimed is:

1. A method for preparing a cell line exhibiting directed constitutive hypermutation of a target nucleic acid region, comprising screening a cell population for ongoing target sequence diversification, wherein said screening comprises determining the mutation rate of the target nucleic acid region relative to the mutation rate of a non-target nucleic acid region, and selecting a cell in which the rate of target nucleic acid mutation exceeds the rate of non-target nucleic acid mutation by a factor of 100 or more, wherein the rate of mutation in the cell line is modulated by genetic manipulation of one or more DNA repair genes, and wherein said genetic manipulation is selected from the group consisting of gene deletion, conversion, and insertion.

2. A method according to claim 1, wherein the cell line is a lymphoid cell line.

3. A method according to claim 2, wherein the cell line is an immunoglobulin-expressing cell.

4. A method according to claim 1, wherein the cell line expresses the target nucleic acid region in a manner that facilitates selection of cells comprising mutants of said target nucleic acid region.

5. A method according to claim 4, wherein the cell line expresses a gene product encoded by the target nucleic acid region on the cell surface.

6. A method according to claim 1, wherein the cell line comprises a cell type which hypermutates in vivo.

7. A method according to claim 6, wherein the cell line is a Burkitt lymphoma, follicular lymphoma or diffuse large cell lymphoma cell line.

8. A method according to claim 1, further comprising the steps of isolating one or more cells which display target sequence diversification, and comparing the rate of accumulation of mutations in the target sequences with that in non-target sequences in the isolated cells.

9. A method according to claim 8, wherein the target sequence is an immunoglobulin V-gene sequence.

10. A method according to claim 9, wherein cells of said cell population are screened by assessing loss of an expressed immunoglobulin.

11. A method according to claim 1 or 8, wherein cells of said cell population are screened by assessment of mutation rates by direct sequencing of the target sequences.

12. A method according to claim 1 or 8, wherein cells of said cell population are screened by an immunofluorescence technique.

13. A method according to claim 1, wherein said one or more DNA repair genes are Rad51 analogues and/or paralogues.

14. A method according to claim 1, wherein the DNA repair genes are selected from the group consisting of Rad51b, Rad51c and analogues and/or paralogues thereof.

* * * * *